(12) United States Patent (10) Patent No.: US 11,701,107 B2
Wulc et al. (45) Date of Patent: Jul. 18, 2023

(54) SUTURING DEVICE AND CLAMP FOR USE WITH SAME

(71) Applicant: TSYMM INNOVATIONS LLC, Wynnewood, PA (US)

(72) Inventors: Allan Wulc, Bryn Mawr, PA (US); Joel Bernstein, Belle Mead, NJ (US); Douglas Hudson, Hopkinton, MA (US); Bruce Bernstein, Wynnewood, PA (US)

(73) Assignee: TSYMM INNOVATIONS LLC, Wynnewood, PA (US)

( * ) Notice: Subject to any disclaimer, the term of this patent is extended or adjusted under 35 U.S.C. 154(b) by 0 days.

(21) Appl. No.: 17/703,771

(22) Filed: Mar. 24, 2022

(65) Prior Publication Data

US 2022/0304677 A1 Sep. 29, 2022

Related U.S. Application Data

(60) Provisional application No. 63/166,864, filed on Mar. 26, 2021.

(51) Int. Cl.
*A61B 17/04* (2006.01)
*A61B 90/30* (2016.01)
*A61B 17/00* (2006.01)

(52) U.S. Cl.
CPC .......... *A61B 17/0491* (2013.01); *A61B 90/30* (2016.02); *A61B 2017/00477* (2013.01); *A61B 2017/00566* (2013.01)

(58) Field of Classification Search
CPC ...... A61B 17/0469; A61B 2017/00323; A61B 17/0625; A61B 2017/00314;
(Continued)

(56) References Cited

U.S. PATENT DOCUMENTS 3,946,740 A * 3/1976 Bassett .............. A61B 17/0469
606/145
4,747,358 A 5/1988 Moll et al.
(Continued)

FOREIGN PATENT DOCUMENTS

| AU | 2013245502 A1 | 11/2013 |
|---|---|---|
| EP | 1284658 B1 | 1/2013 |
| EP | 1631201 B1 | 11/2018 |

OTHER PUBLICATIONS

"Continuous Suture Device for Gastrointestinal Endoscope," Mechatronics Field Robotics Lab, Available at: http://163.152.126.15/Research_GI.htm (2017).
(Continued)

*Primary Examiner* — Sarah A Simpson
*Assistant Examiner* — Raihan R Khandker
(74) *Attorney, Agent, or Firm* — Volpe Koenig

(57) ABSTRACT

A suturing device comprising an elongated member including a cavity formed in a surface thereof, a needle passage, and a vacuum port. When the elongated member is inserted into a body including tissue and a vacuum is applied to the cavity, the tissue is captured by the cavity. A needle pusher is operable to move a needle having a sutured attached thereto through the tissue until a first end of the needle is captured by a needle capturing assembly. A clamp coupled to the elongated member is used to extract the needle from the needle capturing assembly and reposition the needle with suture attached to be re-engaged by the needle pusher. The cavity may include a plurality of cavity portions for capturing multiple contiguous portions of the tissue such that a single pass of the needle and the suture results in the suturing of the multiple portions of the tissue.

22 Claims, 81 Drawing Sheets

(58) Field of Classification Search
CPC .. A61B 2017/00243; A61B 2017/0472; A61B 2017/2908; A61B 18/1442; A61B 17/2909; A61B 17/282; A61B 17/0491; A61B 17/04; A61B 17/06; A61B 17/062; A61B 17/06061; A61B 17/0482; A61B 17/0483
See application file for complete search history.

(56) References Cited

U.S. PATENT DOCUMENTS

| | | | |
|---|---|---|---|
| 5,792,153 A | 8/1998 | Swain et al. | |
| 5,860,992 A * | 1/1999 | Daniel | A61B 17/0491 606/139 |
| 7,060,079 B2 | 6/2006 | Wulc et al. | |
| 7,399,304 B2 * | 7/2008 | Gambale | A61B 17/0401 606/41 |
| 8,172,857 B2 | 5/2012 | Fogel | |
| 8,465,471 B2 * | 6/2013 | Cucin | A61M 1/0058 600/109 |
| 8,641,729 B2 | 2/2014 | Filipi et al. | |
| 9,149,270 B2 | 10/2015 | Fogel | |
| 2004/0034371 A1 | 2/2004 | Lehman et al. | |
| 2004/0158125 A1 | 8/2004 | Aznoian et al. | |
| 2004/0236356 A1 | 11/2004 | Rioux et al. | |
| 2006/0085016 A1 | 4/2006 | Eremia | |
| 2008/0147096 A1 * | 6/2008 | Aznoian | A61B 17/0469 606/232 |
| 2009/0253998 A1 | 10/2009 | Chen | |
| 2010/0137888 A1 | 6/2010 | Wulc et al. | |
| 2012/0022560 A1 * | 1/2012 | Ferreira | A61B 1/00087 606/145 |
| 2018/0263619 A1 | 9/2018 | Steege | |
| 2021/0322004 A1 * | 10/2021 | Khanicheh | A61B 17/0469 |

OTHER PUBLICATIONS

"Endoscopic Suturing Plication," RR School of Nursing (2018).
Swain et al. "Bard EndoCinch: the device, the technique, and pre-clinical studies" Gastrointestinal endoscopy clinics of North America vol. 13,1, 75-88 (2003).

* cited by examiner

SUTURING DEVICE AND CLAMP FOR USE WITH SAME

CROSS REFERENCE TO RELATED APPLICATION

This application claims the benefit of U.S. Provisional Application No. 63/166,864, filed Mar. 26, 2021, the contents of which are incorporated herein by reference.

FIELD OF THE DISCLOSURE

The disclosed embodiments relate generally to medical devices used in surgical procedures and, more particularly, to suturing devices and clamps for facilitating multiple passes of a needle and suture through tissue.

BACKGROUND

Surgery has evolved such that many operations are being performed through incisions of ever-decreasing size. The greatest limitations in performing surgery through small incisions is the difficulty of engaging tissue and passing sutures at a location remote from the incision point. While some surgeons develop the manual dexterity and experience to effectively suture tissue remote from the incision point, very few techniques have been developed to deal with this problem effectively.

Often surgeons are forced to make additional, and potentially longer, incisions, simply because of the difficulty of passing the suture. For example, in performing an endoscopic facelift, the surgeon is often forced to place an incision inside the mouth for wide access to the suturing location. The surgeon may also need to create a large internal space within the patient body (oftentimes referred to as "undermining") to clear enough space to allow for the instrumentation required to pass the suture and subsequently retrieve the needle. With manual remote access techniques, often a significant amount of skin must be (lifted) undermined from the underlying fascia, fat and musculature to allow room to maneuver an endoscope, a needle holder, and the grasping forceps. The creation of this large internal space has the potential to damage internal nerves, blood vessels, and organs. It is also disruptive to the tissue, which can prolong and/or compromise healing. Furthermore, oftentimes four hands are necessary (the surgeon's and an assistant's) to hold the instrumentation, to grasp the needle, and to pass and retrieve the suture.

The limitations of currently available techniques as discussed above produce certain potential surgical risks including needle breakage within the face, needle loss within the face, injury to the facial nerve, its branches, sensory nerves, and blood vessels, dimpling in the skin, improper needle location, inability to pass the suture to obtain the desired lifting effect, as well as the need to open the area completely to retrieve a lost needle or for repair of nerves or vessels.

Passing a suture within the body demands the opening of a space created by subcutaneous undermining thereby allowing enough tissue to be opened to create a space in which to pass the suture and retrieve the needle. In procedures using minimally invasive approaches through a small incision remote from the incision point, wide undermining must be carried out in order to deliver the needle using forceps and to remove it from tissue under endoscopic visualization. This procedure is extremely difficult, if not impossible, without endoscopic visualization or a larger open-access incision to allow for direct visualization. Certain conventional suturing devices do not allow the surgeon to make multiple passes of a suture, and require that multiple sutures be used. Those conventional suturing devices that do allow for multiple passes of the suture, however, are mechanically complex. Hence, there exists a need for a device that facilitates easy passage of a suture in a remote location from the incision point with minimal undermining under either endoscopic or non-visualized means and that allows for multiple passes of the suture to secure tissues within the body.

SUMMARY

A suturing device according to the present disclosure is a device used in surgical procedures for sewing tissue. The suturing device can be controlled externally of the patient, for example under direct visualization by the surgeon, by endoscopic means, or without any visualization by the surgeon, and typically uses a needle attached to a length of suture. A clamp according to the present disclosure is a mechanical device having parts brought together for holding or compressing an object, such as a needle. As described herein, according to the present disclosure, a clamp in combination with a suturing device may be used to facilitate multiple passes of a needle and suture through tissue.

In an embodiment of the present disclosure, a suturing device is provided. The suturing device includes an elongated member dimensioned for insertion into a body including tissue. The elongated member including a first end and a second end opposite the first end, a cavity formed in a surface of the elongated member, a needle passage, and a vacuum port. The cavity includes a first end and a second end opposite the first end and wherein when the elongated member is inserted into the body and a vacuum is applied to the cavity by a vacuum source through the vacuum port, the tissue is captured by the cavity. The suturing device further includes a needle capturing assembly disposed between the second end of the cavity and the second end of the elongated member, a needle pusher including a first end for engaging a needle, wherein when the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly, and a clamp coupled to the elongated member and moveable in the second direction such that when the clamp clamps the second end of the needle and is moved in the second direction, the first end of the needle is extracted from the needle capturing assembly and the needle is repositioned to be engaged by the first end of the needle pusher.

In another embodiment of the present disclosure, an apparatus for use with a suturing device is provided, wherein the suturing device includes an elongated member dimensioned for insertion into a body including tissue. The elongated member includes a first end and a second end opposite the first end, a cavity formed in a surface thereof, a needle passage, and a vacuum port. The cavity includes a first end and a second end opposite the first end. When the elongated member is inserted into the body and a vacuum is applied to the cavity by a vacuum source through the vacuum port, the tissue is captured by the cavity. The suturing device further includes a needle capturing assembly disposed between the second end of the cavity and the second end of the elongated member and a needle pusher including a first end for engaging a needle. When the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly. The apparatus includes a base dimensioned to fit within the cavity. The apparatus further includes a clamp coupled to the base so as to be moveable in the second direction with respect to the base. The clamp is operable to clamp a second end of the needle opposite the first end of the needle such that when the clamp clamps the second end of the needle when the first end of the needle is captured by the needle capturing assembly and the clamp is moved in the second direction, the first end of the needle is extracted from the needle capturing assembly and the needle is repositioned to be engaged by the first end of the needle pusher.

In yet another embodiment of the present disclosure, a suturing device and an apparatus for use with the suturing device are provided. The suturing device includes a needle capturing assembly and a needle pusher. The apparatus includes a clamp that is configured to move with respect to the suturing device. The clamp is operable to clamp a second end of the needle opposite a first end of the needle when the first end of the needle is captured by the needle capturing assembly and the second end of the needle has been disengaged from the needle pusher. The clamp is operable to extract the first end of the needle from the needle capturing assembly and reposition the needle to be re-engaged by the needle pusher.

In yet another embodiment of the present disclosure, a suturing device is provided. The suturing device includes an elongated member dimensioned for insertion into a body including tissue, the elongated member including a first end and a second end opposite the first end, a cavity formed in a surface thereof, a needle passage, and a vacuum port, wherein the cavity includes a first end and a second end opposite the first end and wherein when the elongated member is inserted into the body and a vacuum is applied to the cavity by a vacuum source through the vacuum port, the tissue is captured by the cavity. The suturing device further includes a needle capturing assembly disposed between the second end of the cavity and the second end of the elongated member and a needle pusher including a first end for engaging a needle. When the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly. The needle pusher is further moveable in a second direction such that the needle is disengaged from the needle pusher while the first end of the needle remains captured by the needle capturing assembly. Application of the vacuum to the cavity is controlled by the movement of the needle pusher.

In yet another embodiment of the present disclosure, light from a light source may be used to illuminate tissue when the suturing device is inserted within the body to assist with placement of the suturing device within the body without having visual contact with the device. In addition, during operation of the suturing device, a user may be provided with audible and/or tactile feedback from the device to enable the user to ascertain a position of the needle pusher and needle without having visual contact with either the needle pusher or the needle.

BRIEF DESCRIPTION OF THE DRAWINGS

Various embodiments of the present disclosure are illustrated by way of example, and not limited by the appended figures, in which like references indicate similar elements, and in which.

Further areas of applicability of the present disclosure will become apparent from the detailed description provided hereinafter. It should be understood that the detailed description of exemplary embodiments is intended for illustration purposes only and is, therefore, not intended to necessarily limit the scope of the present disclosure.

DETAILED DESCRIPTION

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. In one example, the teachings presented and the needs of a particular application may yield multiple alternate and suitable approaches to implement the functionality of any detail described herein. Therefore, any approach may extend beyond the particular implementation choices in the following embodiments that are described and shown.

References to "an embodiment", "another embodiment", "yet another embodiment", "one example", "another example", "yet another example", "for example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Figure 1A:
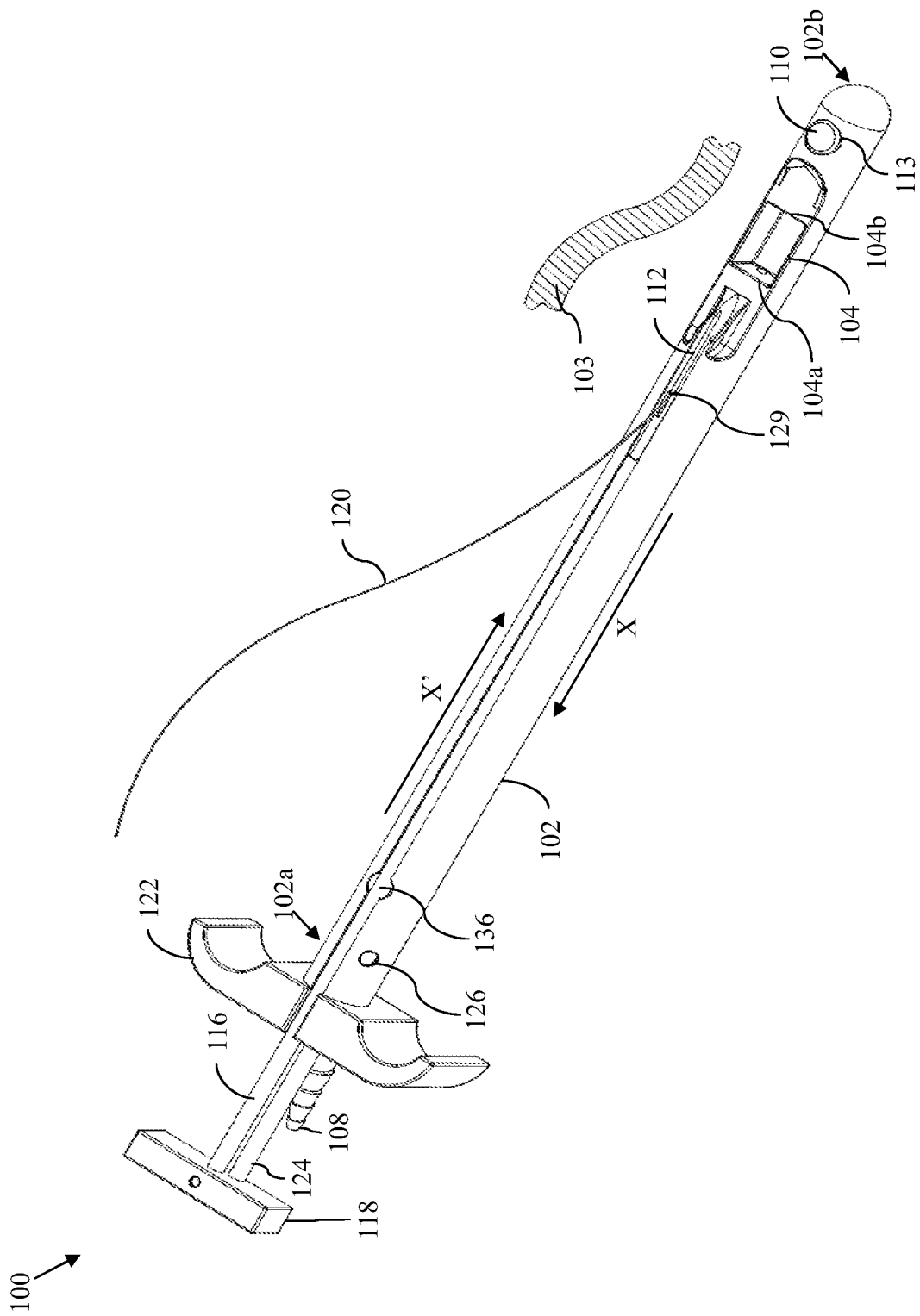
FIG. 1A illustrates a perspective view of a suturing device, in accordance with an exemplary embodiment of the present disclosure.
Figure 1B:
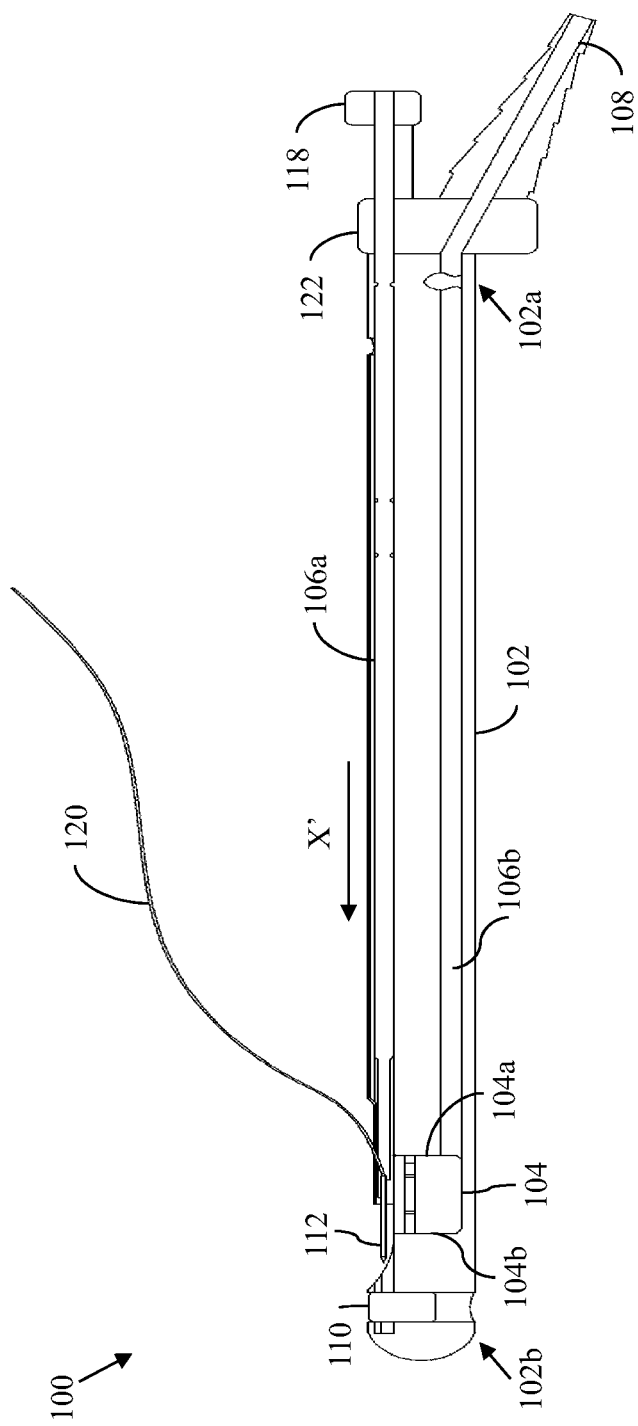
FIG. 1B illustrates a cross-sectional side view of the suturing device, in accordance with an exemplary embodiment of the present disclosure.
Figure 1C:
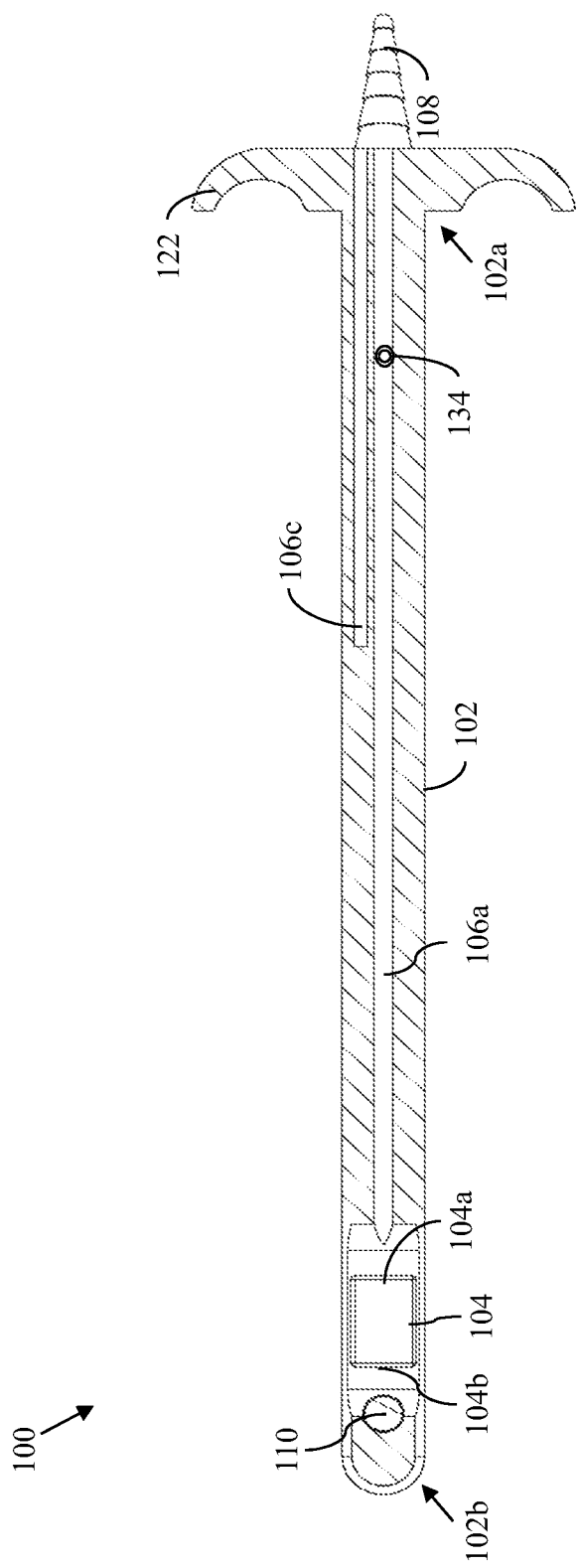
FIG. 1C illustrates a cross-sectional top view of the suturing device, in accordance with an exemplary embodiment of the present disclosure.

FIGS. 1A, 1B, and 1C illustrate a perspective view, a cross-sectional side view, and cross-sectional top view of a suturing device 100, in accordance with an exemplary embodiment of the disclosure. As shown in FIGS. 1A, 1B, and 1C, the suturing device 100 includes an elongated member 102. Preferably, the elongated member 102 is dimensioned for insertion into a body including tissue (e.g., tissue 103) to suit a particular application. For example, in situations where the suturing device 100 is to be used to perform endoscopic plastic surgery, such as described in U.S. Pat. No. 7,060,079, the elongated member 102 is dimensioned for insertion into an incision in the patient and for engaging subcutaneous tissue, fat, fascia, or muscle. The elongated member 102 further includes a proximal end 102a and a distal end 102b ("proximal" and "distal" being from the perspective of a user of the suturing device 100) and a cavity 104 is formed in a surface of the elongated member 102. The elongated member 102 is provided with a working channel 106a and a suction channel 106b, as shown in FIG. 1B. A first end of the suction channel 106b has a vacuum port 108 that may be coupled to a vacuum source (not shown). A second end of the suction channel 106b is coupled to the cavity 104 such that the cavity 104, the suction channel 106b, and the vacuum source are in fluidic communication. Thus, when the elongated member 102 is inserted into a body including the tissue 103 to be sutured and a vacuum (i.e., negative pressure) is applied to the cavity 104 by the vacuum source coupled to the vacuum port 108, the tissue 103 is suctioned into and captured by the cavity 104. Preferably, the cavity 104 is dimensioned to suit a particular application and to accommodate the type and amount of tissue that is to be captured. For example, the cavity 104 can be formed as a cuboid, as shown in FIG. 1A, to include a first wall 104a (i.e., a front wall from the perspective of the user of the suturing device 100) at a first end of the cavity 104 and a second wall 104b (i.e., a rear wall from the perspective of the user of the suturing device 100) at a second end of the cavity 104 parallel and opposite to the first wall 104a. The cavity 104 may have other shapes, such as an ovoid, cylindrical, cuboid, pyramidal, parabolic, conical, or free-form shape.

As further shown in FIGS. 1A, 1B, and 1C, a needle capturing assembly 110 is disposed between the second wall 104b of the cavity 104 and the distal end 102b of the elongated member 102 for capturing and allowing for the subsequent release of a needle 112 during operation of the suturing device 100 as described below. The needle capturing assembly 110 may be made of any material, such as but not limited to rubber, elastomer, or the like, that allows the needle capturing assembly 110 to capture the needle 112 during operation of the suturing device 100 and allows the needle 112 to be subsequently released as described below. The needle capturing assembly 110 may be permanently disposed within the elongated member 102 such that it is not intended for replacement. Alternatively, the needle capturing assembly 110 may be removably disposed within the elongated member 102 such that it may be replaced with a new needle capturing assembly, for example, should the original needle capturing assembly become unusable or be in need of repair. For example, the elongated member 102 may include an opening 113 for receiving the needle capturing assembly 110. The opening 113 is preferably dimensioned such that the needle capturing assembly 110 may be secured within the opening 113, but may also be removed and replaced with the new needle capturing assembly as needed. It should be appreciated that the needle capturing assembly 110 may take forms other than the form shown in FIGS. 1A, 1B, and 2C. For example, the needle capturing assembly 110 may take the form of the punch needle notch and key assembly described in U.S. Pat. No. 8,172,857, the contents of which are hereby incorporated by reference. Other assemblies know to those skilled in the art for capturing and allowing for the subsequent release of a needle during operation of the suturing device may also be used.

Figure 1D:
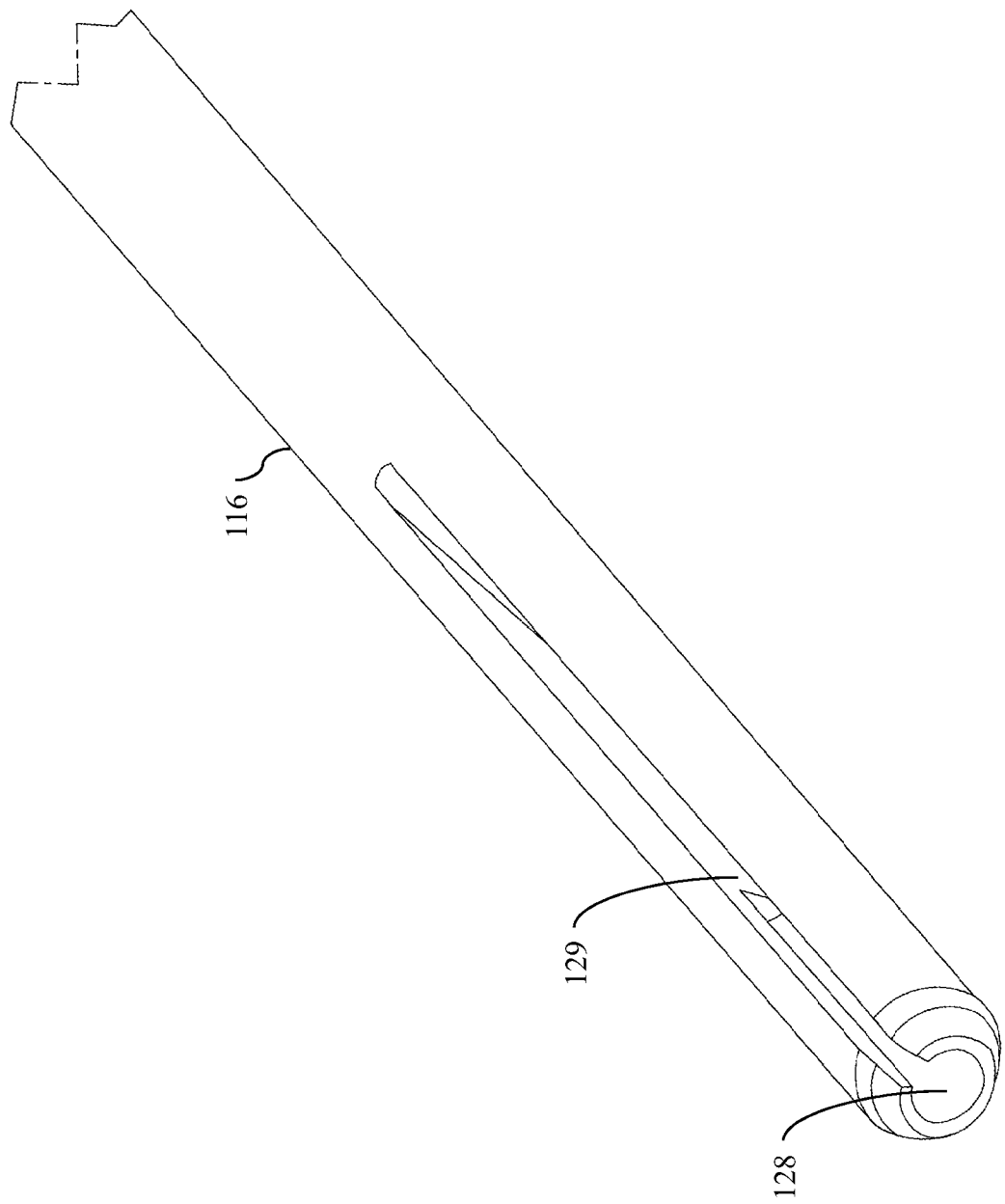
FIG. 1D illustrates an enlarged view of a portion of a needle pusher of the suturing device, in accordance with an exemplary embodiment of the present disclosure.
Figure 1E:
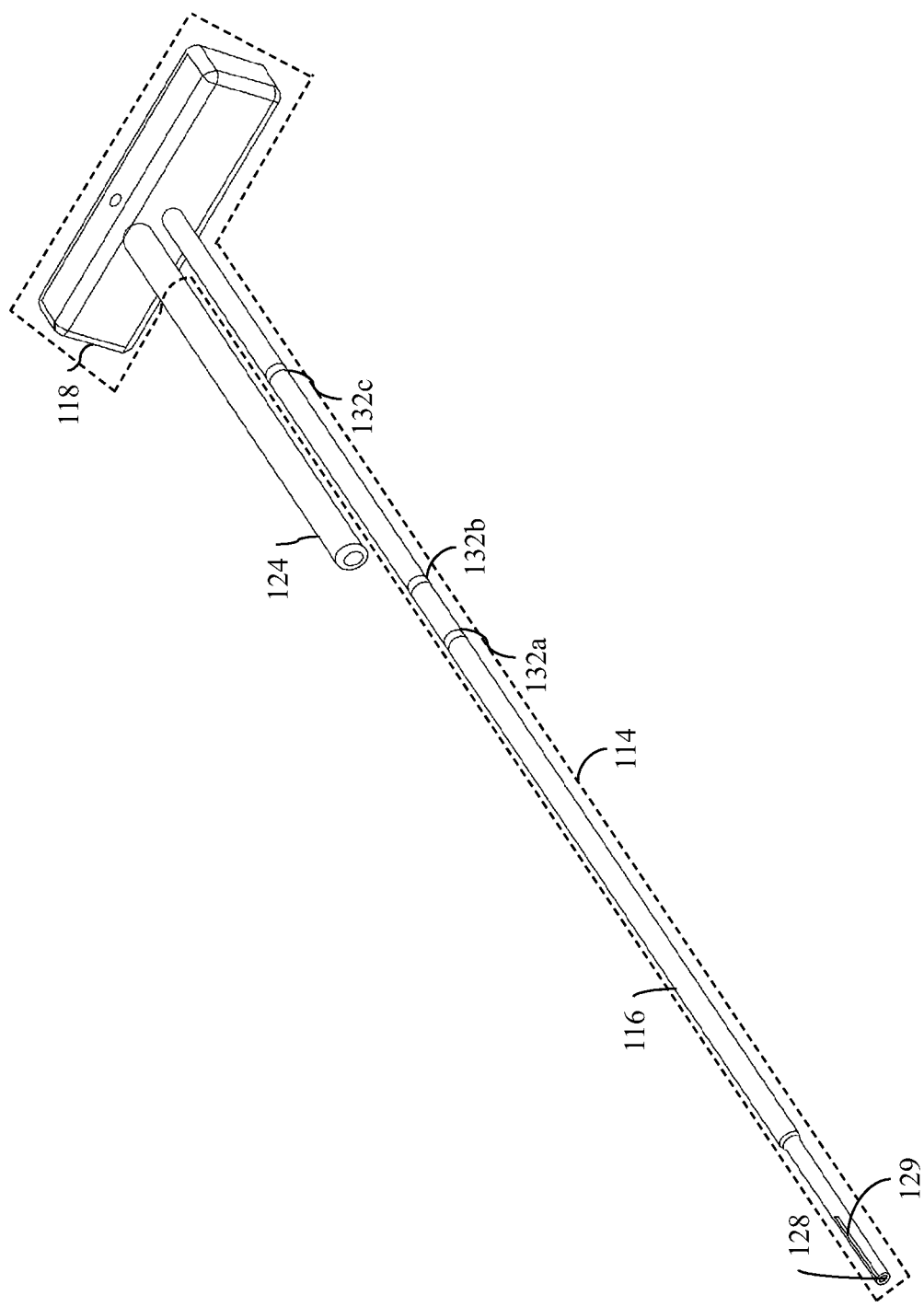
FIG. 1E illustrates a perspective view of a needle pusher assembly and a blocking member of the suturing device, in accordance with an exemplary embodiment of the present disclosure.

As shown in FIG. 1E, the suturing device 100 further includes a needle pusher assembly 114. The needle pusher assembly 114 includes a needle pusher 116 and an operating handle 118, both of which are also shown in FIGS. 1A and 1B. The needle pusher 116 is dimensioned such that it may be moved in directions X and X' (see FIG. 1A) within the working channel 106a of the elongated member 102 as described below. As further shown in FIG. 1A, the needle 112 having a suture 120 attached to a first end thereof may be engaged by a first end of the needle pusher 116. The suture 120 may be attached to the first end of the needle 112, for example, by use of shrink tubing, swaging, or other means known to those skilled in the art. The first end of the needle pusher 116 is configured to engage the needle 112 having the suture 120 attached thereto. In one embodiment, the needle pusher 116 may comprise a solid rod and the needle 112 may be engaged by the first end of the needle pusher 116, for example, by slip fitting the first end of the needle 112 into a hole or slot formed in the first end of the needle pusher 116, such as shown in FIG. 1E. In another embodiment, the needle pusher 116 may comprise a cylindrical tube and the needle 112 may be engaged by the first end of the needle pusher 116 by slip fitting the first end of the needle 112 into the first end of the needle pusher 116. Other configurations known to those skilled in the art may be used to cause the needle pusher 116 to engage the needle 112. Preferably, when the needle 112 is engaged by the needle pusher 116, the suture 120 may exit the suturing device 100, for example, through a slit or other opening formed in the elongated member 102 as shown in FIG. 1A. The needle pusher 116 is explained in detail in conjunction with FIG. 1D.

Figure 1F:
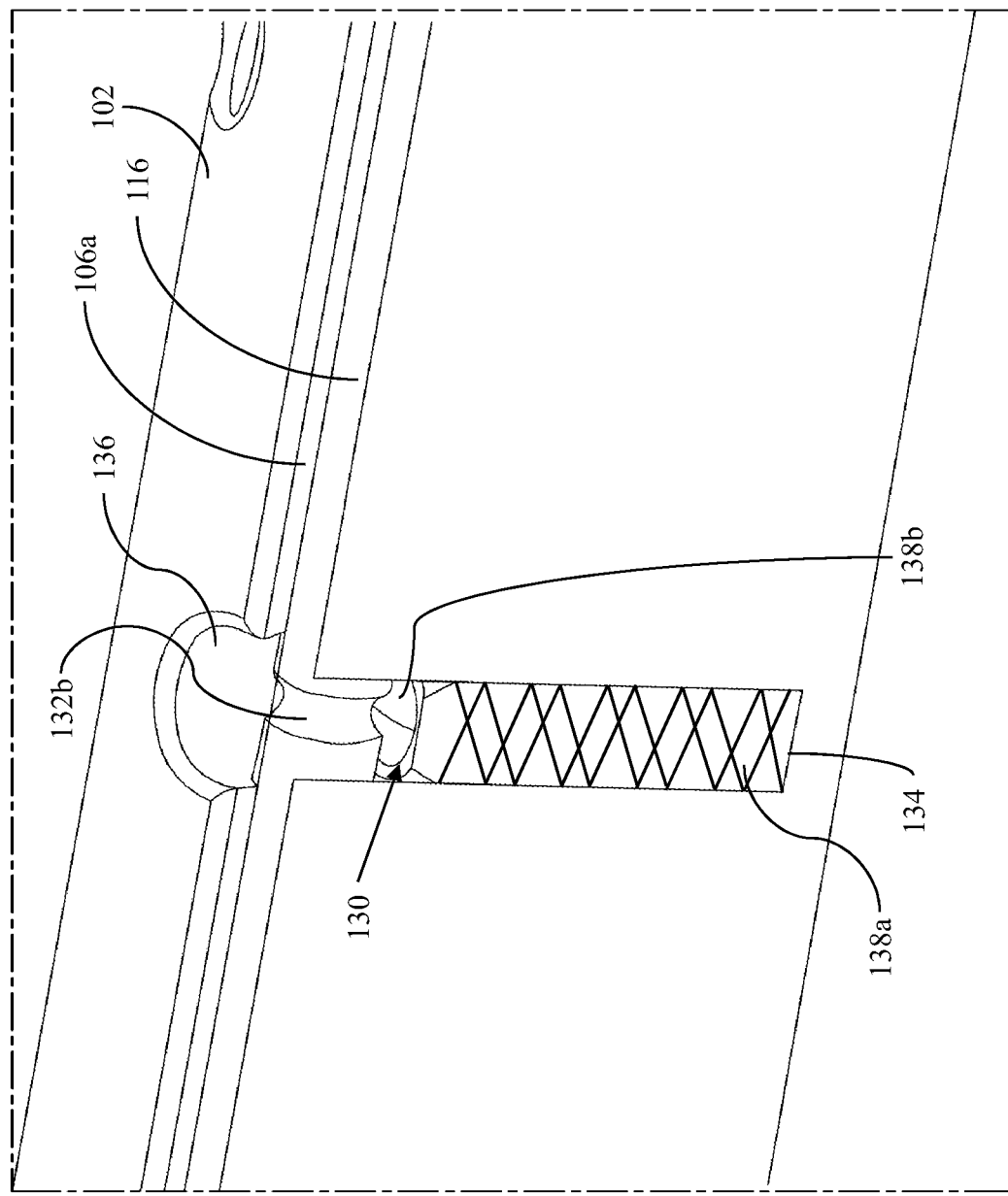
FIG. 1F illustrates an enlarged cross-sectional side view of a ball-spring detent mechanism of the suturing device, in accordance with an exemplary embodiment of the present disclosure.
Figure 1G:
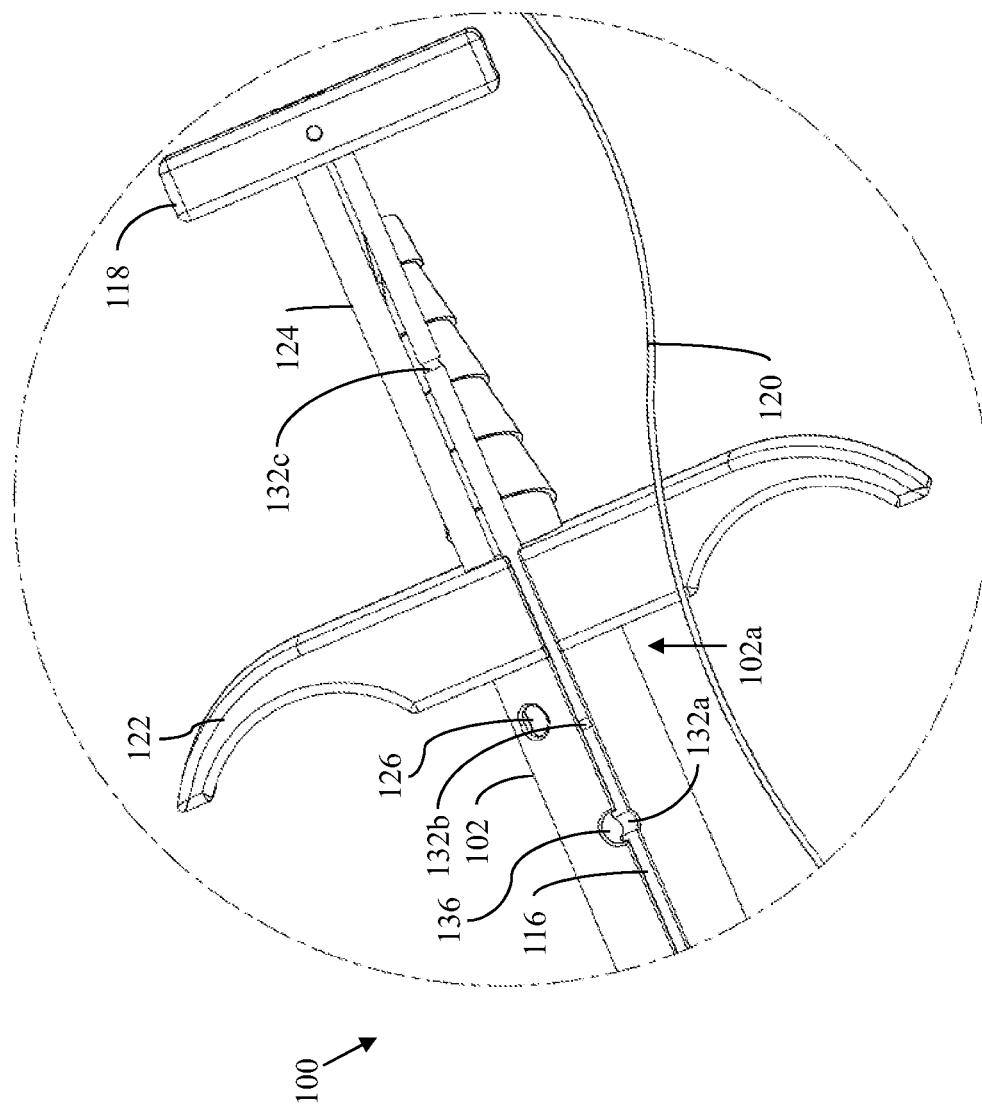
FIGS. 1G-1I illustrate enlarged views of operation of the ball-spring detent mechanism of the suturing device, in accordance with an exemplary embodiment of the present disclosure.
Figure 1H:
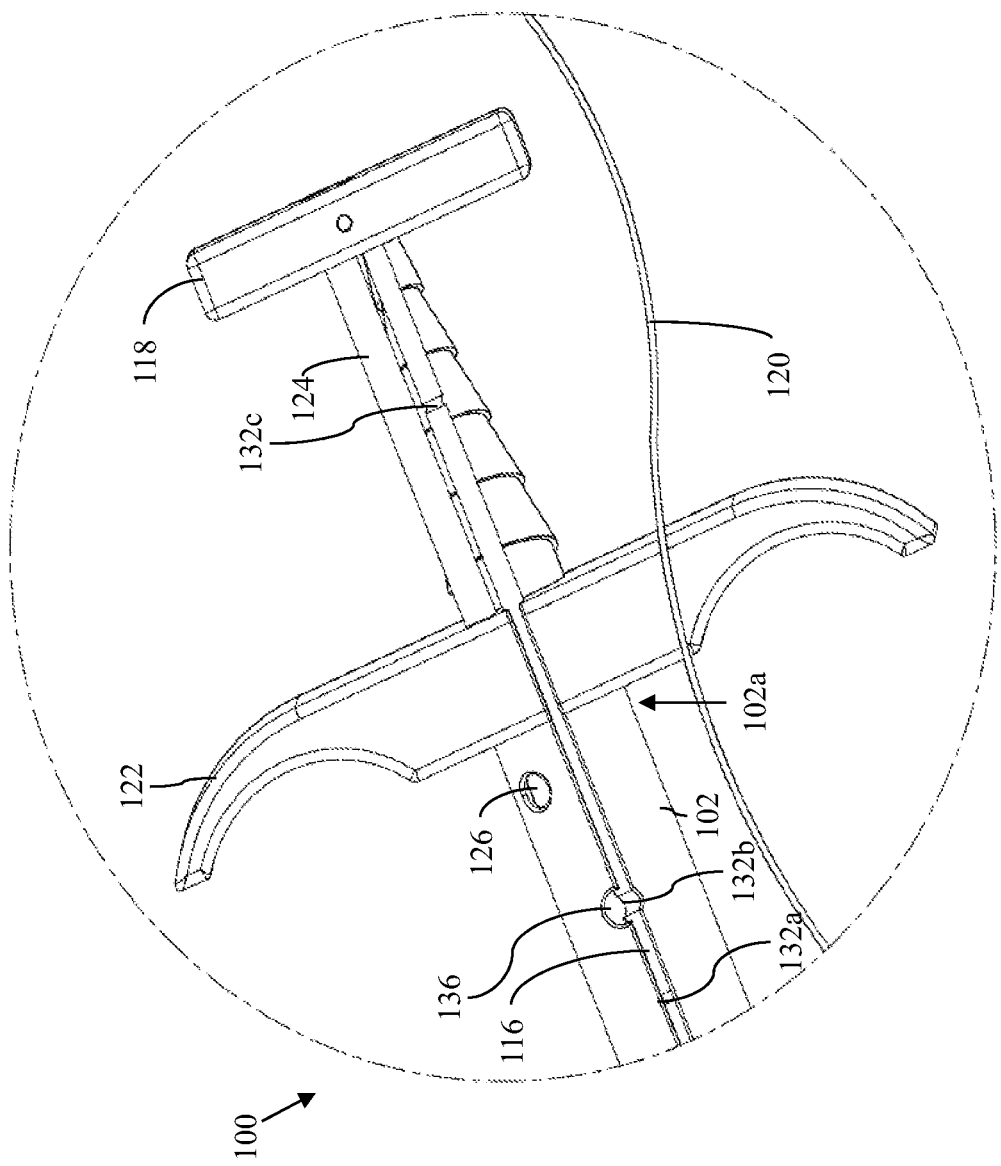

During operation of the suturing device 100, a user may push and/or pull the operating handle 118, using a fixed handle 122 as leverage, to control movement of the needle pusher 116 within the working channel 106a. For example, advancement or retraction of the operating handle 118 translates to a corresponding advancement or retraction of the needle pusher 116 (and the needle 112 and the suture 120 when the needle 112 is engaged by the needle pusher 116) within the working channel 106a. A user operating the suturing device 100 may move the operating handle 118 from a retracted position towards the fixed handle 122 of the suturing device 100, until the operating handle 118 reaches its fully advanced position. In the fully advanced position, the operating handle 118 is preferably in contact with the fixed handle 122. The longitudinal advancement of the operating handle 118 towards the fixed handle 122 forces the needle pusher 116, and, consequently, the needle 112 and the suture 120, to advance longitudinally from a current position towards the distal end 102b of the elongated member 102. As the needle pusher 116, the needle 112, and the suture 120 are advanced, at least the needle 112 and the suture 120 (and, preferably, also the needle pusher 116) pass over the cavity 104 and, in doing so, may penetrate the tissue 103 that has been suctioned into the cavity 104 by a vacuum applied to the suction channel 106b. Preferably, during operation of the suturing device 100, the operating handle 118 is sufficiently advanced towards the fixed handle 122 such that the entirety of the needle 112 passes through the captured tissue 103 and a second end of the needle 112, i.e., the end opposite to the first end at which the suture 120 is attached, is captured by the needle capturing assembly 110, thereby suturing the captured tissue 103 (as shown in FIGS. 1K and 1L).

It should be appreciated that during operation of the suturing device 100, application of a vacuum to the cavity 104 should be coordinated with the passing of the needle 112 and the suture 120 through the tissue 103 such that the tissue 103 is suctioned into and released from the cavity 104 at the appropriate times. Control of the vacuum can be accomplished by manually turning the vacuum source on and off Alternatively, a blocking member 124 attached to the needle pusher assembly 114, in combination with a first aperture 126 and a vacuum control channel 106c formed in the elongated member 102, may be provided to control application of the vacuum to the cavity 104 through normal operation of the suturing device 100 without having to manually turn the vacuum source on and off As shown in FIGS. 1A, and 1E the blocking member 124 may comprise an elongated member coupled to the operating handle 118 and arranged parallel and adjacent to the needle pusher 116. The blocking member 124 is dimensioned to fit within the vacuum control channel 106c (shown in FIG. 1C), which is in fluidic communication with the suction channel 106b. As shown in FIG. 1C, the length of the vacuum control channel 106c is preferably shorter than the length of the working channel 106a. During operation of the suturing device 100, advancement or retraction of the operating handle 118 translates to a corresponding movement of the blocking member 124 through the vacuum control channel 106c, and such movement of the blocking member 124 within the vacuum control channel 106c, in turn, opens or blocks the first aperture 126. Because the first aperture 126 is in fluidic communication with the vacuum control channel 106c, which is further in fluidic communication with the suction channel 106b, opening of the first aperture 126 releases any vacuum pressure created within the cavity 104. Similarly, blocking the first aperture 126 maintains any vacuum pressure created within the cavity 104. Thus, retracting the operating handle 118 results in retraction of the blocking member 124 such that the blocking member 124 does not block the first aperture 126 and air from the environment enters the suction channel 106b via the vacuum control channel 106c through the first aperture 126, thereby negating any vacuum created at the cavity 104 and releasing any captured tissue from the cavity 104. Similarly, advancing the operating handle 118 results in advancement of the blocking member 124 such that the blocking member 124 blocks the first aperture 126, thereby maintaining a vacuum at the cavity 104 such that the tissue 103 may be captured. It should be appreciated that provision of the blocking member 124, the first aperture 126, and the vacuum control channel 106c avoids the need to manually turn the vacuum source on/off. It also enables synchronization of the application of the vacuum to the cavity 104 with the passage of the needle 112 and the suture 120 through the tissue 103 during normal operation of the suturing device 100. As an alternative to the blocking member 124, the user of the suturing device 100 may manually cover/uncover the first aperture 126, for example, with his/her finger, to control the application of the vacuum to the cavity 104. However, in that situation, the user must be aware of the timing of covering/uncovering the first aperture 126 such that application of the vacuum to the cavity 104 is properly synchronized with the movement of the needle 112 and the suture 120.

FIG. 1D illustrates an enlarged view of a portion of the needle pusher 116, in accordance to an exemplary embodiment of the invention. As shown in FIG. 1D, the needle pusher 116 comprises a cylindrical tube or rod. A first end of the needle pusher 116 includes an opening 128 that is configured to engage the first end of the needle 112, as described earlier. The opening 128 is preferably dimensioned to engage the needle 112 by slip fitting. The needle pusher 116 further includes a slit 129 (or other opening) that allows the suture 120 to exit the suturing device 100 and prevent the suture 120 from being in the path of the needle pusher 116 during operation of the suturing device 100. In one embodiment, as shown in FIG. 1D, the slit 129 extends from the end of the needle pusher 116 at which the needle 112 is engaged towards the opposite end of the needle pusher 116. Preferably, the slit 129 slopes towards the outer surface of the needle pusher 116 as shown to help guide and protect the suture 120 as it exits the needle pusher 116 during operation of the suturing device 100.

FIG. 1E illustrates a perspective view of the needle pusher assembly 114 and the blocking member 124 attached to the needle pusher assembly 114, in accordance to an exemplary embodiment of the invention. The needle pusher assembly 114 includes the needle pusher 116 and the operating handle 118. Attached to the operating handle 118 is the blocking member 124. The length of the blocking member 124 is preferably shorter than the length of the needle pusher 116. The needle pusher 116 and the blocking member 124 are configured to slide within the working channel 106a and the vacuum control channel 106c, respectively. The needle pusher 116 may include one or more detents. Each of the one or more detents may engage with a ball-spring pair of a ball-spring detent mechanism of the suturing device 100 for providing the user of the suturing device 100 with audible and/or tactile feedback on a position of the needle pusher 116 relative to the elongated member 102. For example, the number of detents used may vary depending on number of positions that the user requires feedback. In a non-limiting example, each detent may be an indentation, a notch, or a slot formed on a peripheral surface of the needle pusher 116. Preferably, the size of the notch or the indentation or the slot is less than or equal to size or diameter of a ball included in the ball-spring detent mechanism. As an example, the needle pusher 116 in FIG. 1E is shown to include first through third detents 132a-132c and the ball-spring detent mechanism 130 is shown in FIG. 1F. Functionality and working of the ball-spring detent mechanism 130 is explained in detail in conjunction with the FIGS. 1F-1I.

FIG. 1F illustrates an enlarged cross-sectional view of the suturing device 100, in accordance with an exemplary embodiment of the present disclosure. As shown in FIG. 1F, the suturing device 100 includes the ball-spring detent mechanism 130 seated below the needle pusher 116 in a bore 134 (e.g., a cylindrical bore) formed under the working channel 106a through the elongated member 102 of the suturing device 100. The bore 134 is preferably in alignment with a second aperture 136 formed on the elongated member 102 (see, e.g., FIG. 1A). The second aperture 136 may allow the user to visually identify the position of the needle pusher 116 with respect to the elongated member 102. The second aperture 136 also provides a passage through which the ball-spring detent mechanism 130 may be positioned in the bore 134 during assembly of the suturing device 100. The ball-spring detent mechanism 130 includes a spring 138a and a ball 138b loaded over the spring 138a. The spring 138a is dimensioned to be installed in the bore 134. The spring 138a is preferably loaded such that it pushes the ball 138b against the needle pusher 116 as the needle pusher 116 traverses through the working channel 106a (via the advancement and/or retraction of the operating handle 118 by the user). During the traversal of the needle pusher 116 through the working channel 106a, if any of the first through third detents 132a-132c aligns with the second aperture 136, the ball 138b being pushed by the loaded spring 138a engages with a corresponding one of the detents (e.g., the second detent 132b as shown in FIG. 1F). When the ball 138b engages with one of the first through third detents 132a-132c, the ball-spring detent mechanism 130 preferably generates an audible feedback (e.g., a "click" sound) and/or tactile feedback (e.g., a stopping force) for the user of the suturing device 100. The pressure of the ball 138b against one of the first through third detents 132a-132c holds the needle pusher 116 in position until a requisite level of force is applied by the user to the operating handle 118 for advancement or retraction of the needle pusher 116. When the requisite level of force is applied by the user, the ball 138b is pushed back into the bore 134 towards the spring 138a, enabling the advancement or the retraction of the needle pusher 116 across the working channel 106a. In a non-limiting example, the ball-spring detent mechanism 130 may use an object of any shape in place of the ball 138b shown and any type of spring in place of the spring 138a shown, in order to provide the foregoing functions.

It should be appreciated that the audible and/or tactile feedback generated by the engagement and disengagement of the ball 138b and the first through third detents 132a-132c enables the user of the suturing device 100 to ascertain a relative position of the needle pusher 116 and needle 112 within the working channel 106a without having visual contact with either the needle pusher 116 or the needle 112. The audible and/or tactile feedback may also inform the user of the status of the vacuum applied to the cavity 104 when the blocking member 124 is provided as discussed above given that the position of the needle pusher 116 within the working channel 106a corresponds to the position of the blocking member 124 relative to the first aperture 126.

For example, in order to prepare the suturing device 100 for use, the needle pusher 116 (with the needle 112 and the suture 120 engaged) is inserted into the proximal end 102a of the elongated member 102 and pushed towards the fixed handle 122 until the first detent 132a aligns with the second aperture 136, causing the ball 138b to engage with the first detent 132a. As shown in FIG. 1G, when the ball 138b is engaged with the first detent 132a, the ball-spring detent mechanism 130 generates a first audible click sound and holds the needle pusher 116 in position. The first audible click and/or the tactile feedback caused by the engagement of the ball 138b with the first detent 132a indicate that the needle pusher 116 is in the fully retracted position and that the suturing device 100 is ready for use. Moreover, because the blocking member 124 does not block the first aperture 126 when the needle pusher 116 is in the fully retracted position, the first audible click and/or the tactile feedback caused by the engagement of the ball 138b with the first detent 132a also indicate that no vacuum is being applied to the cavity 104.

Upon application of a requisite force to the operating handle 118 pushing it towards the fixed handle 122, the ball 138b is disengaged from the first detent 132a and pushed back into the bore 134 towards the spring 138a. If the user continues to push on the operating handle 118, the needle pusher 116 continues to advance through the working channel 106a until the second detent 132b aligns with the second aperture 136 and engages with the ball 138b generating a second audible click sound and holding the needle pusher 116 in an intermediate position (as shown in FIG. 1H). The second audible click and/or the tactile feedback caused by the engagement of the ball 138b with the second detent 132b indicate that the needle pusher 116 is in an intermediate position and that needle 112 is in a preparatory position to be passed through the tissue 103. Moreover, because the blocking member 124 blocks the first aperture 126 when the needle pusher 116 is in the intermediate position, the second audible click and/or the tactile feedback caused by the engagement of the ball 138b with the second detent 132b also indicate that the vacuum is being applied to the cavity 104 (via the suction channel 106b).

Figure 1I:
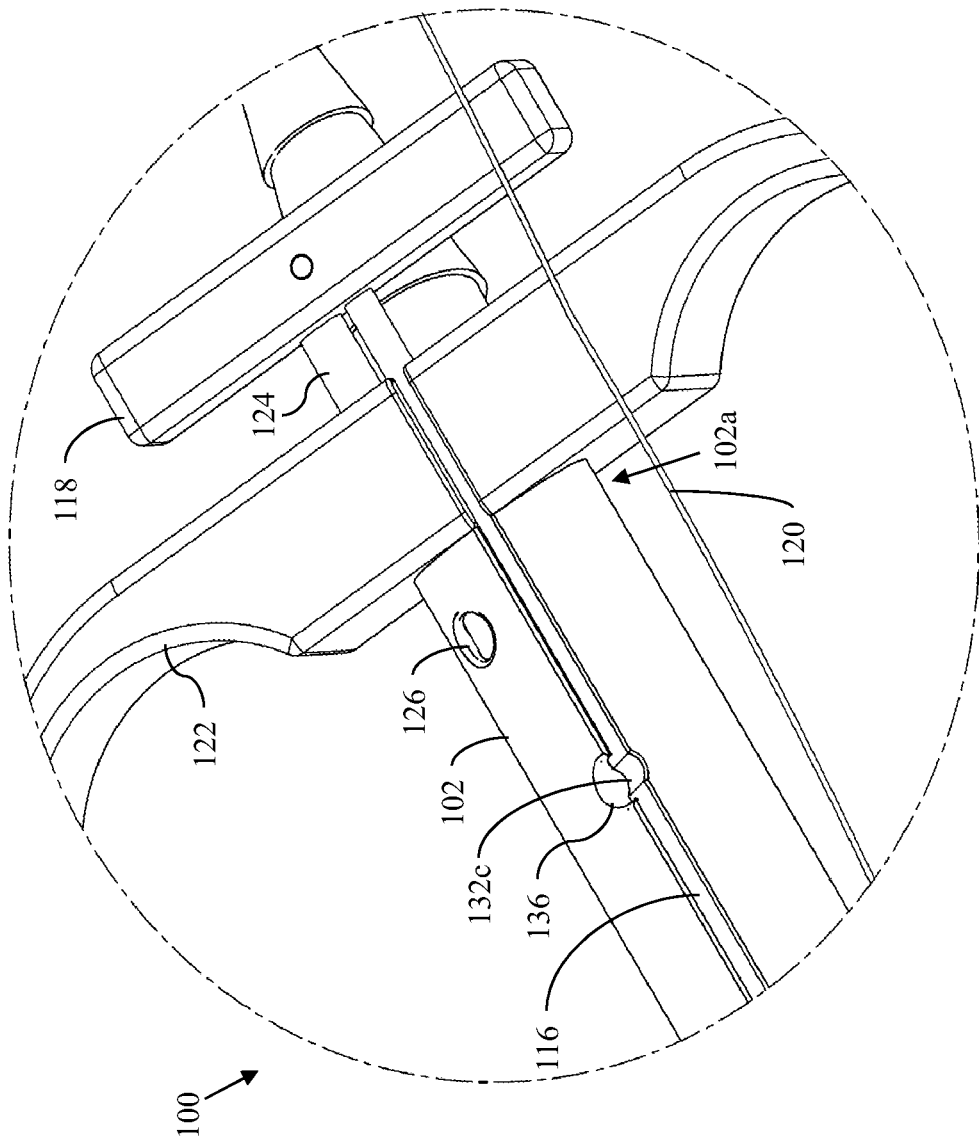

When the operating handle 118 is further advanced by the user to the fully advanced position, the third detent 132c eventually becomes aligned with the second aperture 136 and engaged with the ball 138b, generating a third audible click sound and holding the needle pusher 116 in position (as shown in FIG. 1I). The third audible click and/or the tactile feedback caused by the engagement of the ball 138b with the third detent 132c indicate that the needle pusher 116 is in the fully advanced position, i.e., that the needle pusher 116 has advanced past the second wall 104b of the cavity 104 towards the distal end 102b such that the entirety of the needle 112 has passed through the tissue 103, the suture 120 has passed through the tissue 103, and the needle 112 has been captured by the needle capturing assembly 110.

Figure 1J:
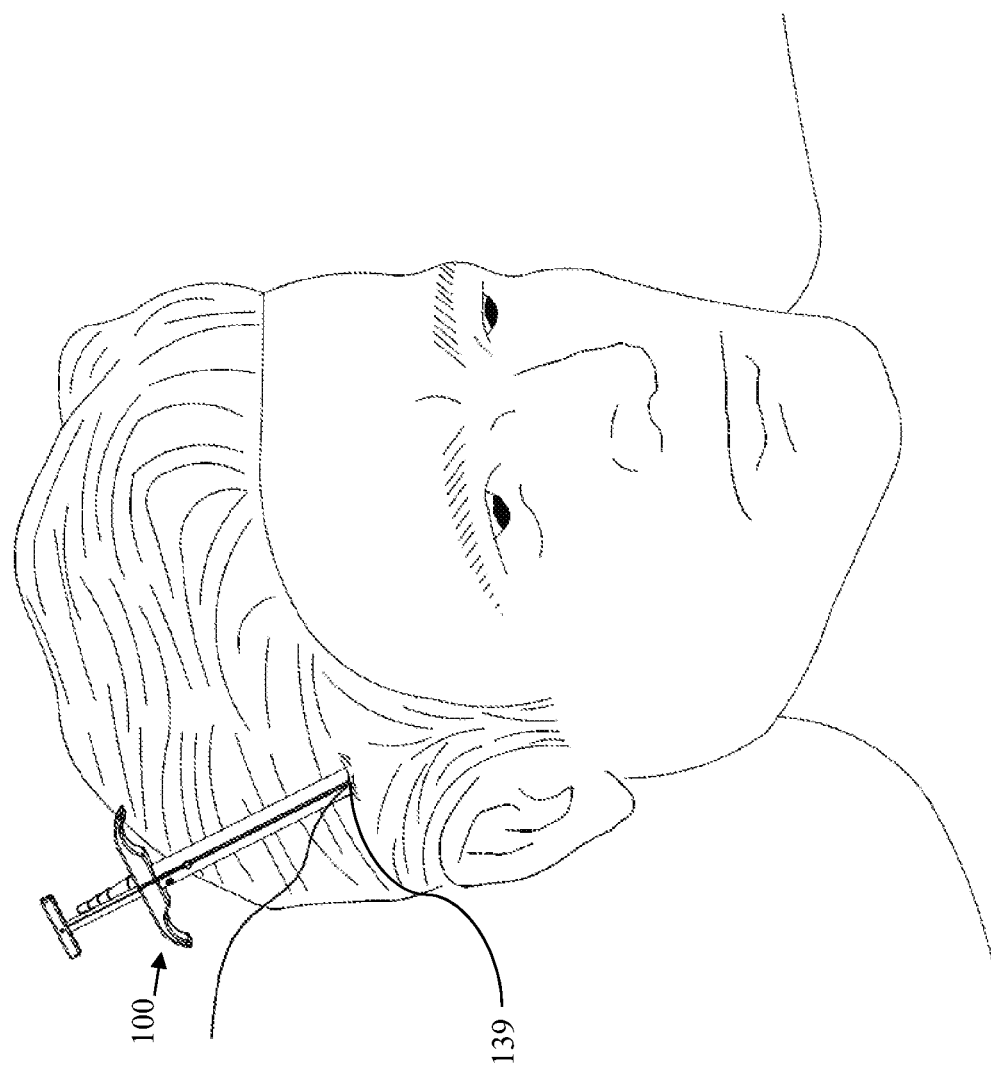
FIG. 1J illustrates a representative view of a face of a patient, with a slit incision shown therein, through which the suturing device is inserted, in accordance with an exemplary embodiment of the present disclosure.
Figure 1K:
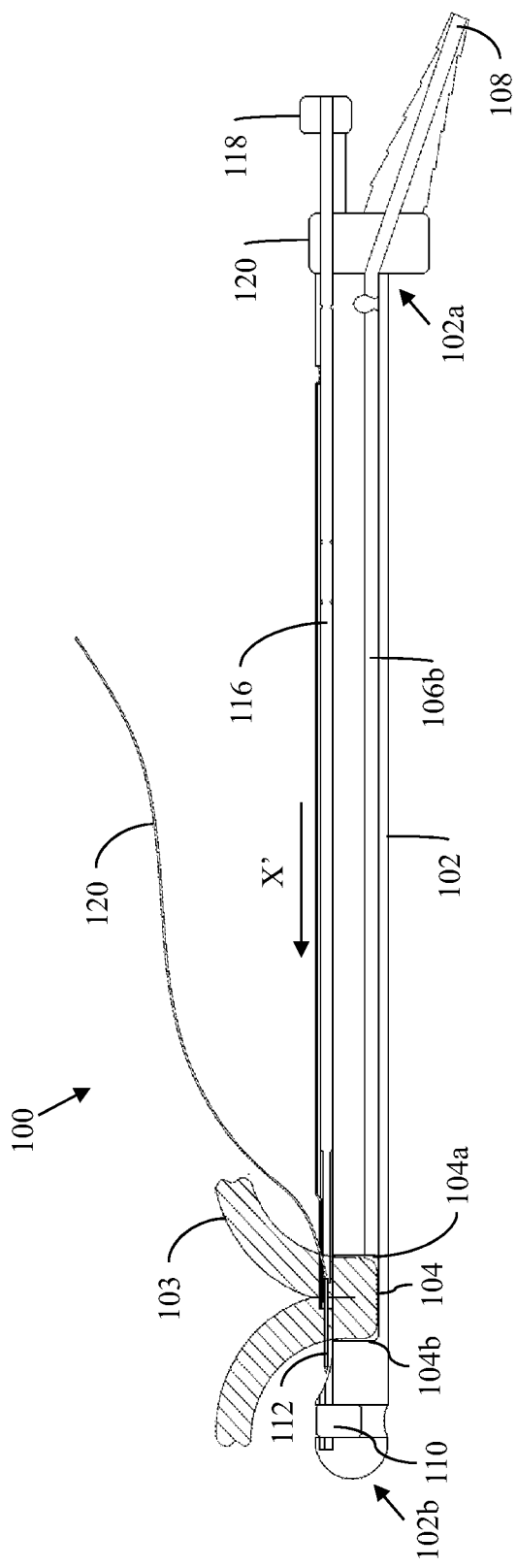
FIG. 1K illustrates a cross-sectional side view of the suturing device when the operating handle is in an advancing position, in accordance with an exemplary embodiment of the present disclosure.
Figure 1L:
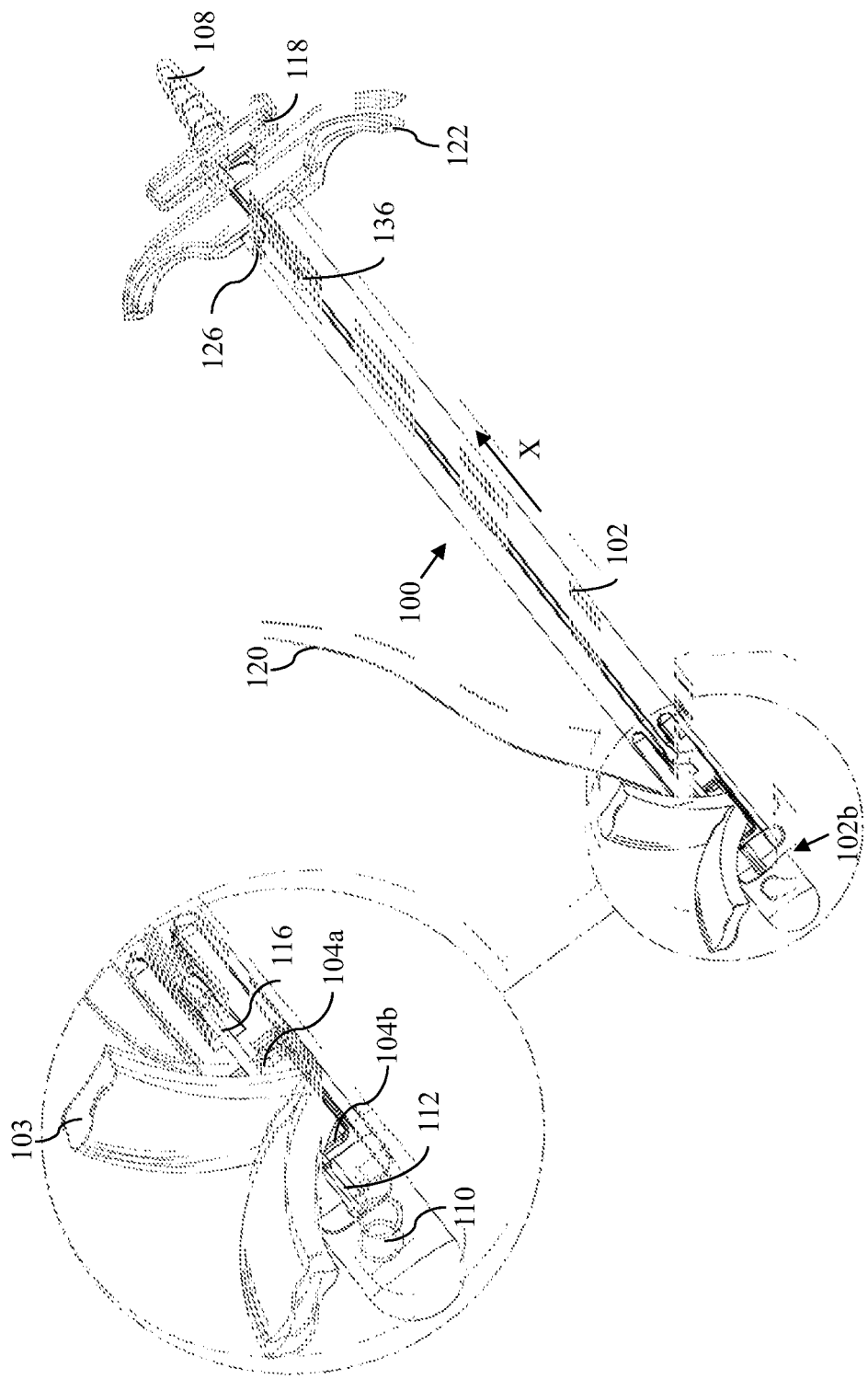
FIG. 1L illustrates a perspective view and an enlarged view of a distal end of the suturing device when an operating handle is in a fully advanced position, in accordance with an exemplary embodiment of the present disclosure.

A preferred operation of the suturing device 100 is explained in conjunction with FIGS. 1A through 1M. By way of example only, the operation of the suturing device 100 will be described in connection with a mid-face lift procedure. As explained above, the operating handle 118 is initially in the fully retracted position as shown in FIG. 1A, i.e., the ball 138b is engaged with the first detent 132a of the needle pusher 116. While in the fully retracted position, a vacuum source (not shown) coupled to the vacuum port 108 is turned on. As explained above, however, no vacuum is applied to the cavity 104 because the first aperture 126 is not blocked by the blocking member 124. A user then inserts the elongated member 102 into a patient's body. For example, when forming a mid-face lift procedure, the elongated member 102 is inserted into a slit incision 139 that has been cut through the skin of the face of the patient, generally above the temporal hairline of the patient, e.g., as shown in FIG. 1J. Once the cavity 104 is positioned at a desired location within the body, the user pushes on the operating handle 118, using the fixed handle 122 as leverage, to move the operating handle 118 towards the fixed handle 122. Eventually, the operating handle 118 is sufficiently moved such that the needle pusher 116 is at the intermediate position, i.e., the ball 138b is engaged with the second detent 132b of the needle pusher 116 as discussed above. In this position, the blocking member 124 blocks the first aperture 126 resulting in a vacuum from the vacuum source (not shown) being applied to the suction channel 106b via the vacuum port 108, and to the cavity 104, via the suction channel 106b. As a result, the tissue 103 from the body is suctioned into and thereby captured by the cavity 104. Subsequent, further advancement of the operating handle 118 causes the needle pusher 116, and therefore the needle 112 and the suture 120, to be pushed through the captured tissue 103 as shown in FIG. 1K creating a stitch. Following full advancement of the operating handle 118 such the needle pusher 116 is at the fully advanced position, i.e., the ball 138b is engaged with the third detent 132c of the needle pusher 116 as discussed above, the entirety of the needle 112 (with the suture 120 attached thereto) passes through the suctioned tissue 103 captured within the cavity 104 and a second end of the needle 112 is captured by the needle capturing assembly 110 as shown in FIG. 1L.

Figure 1M:
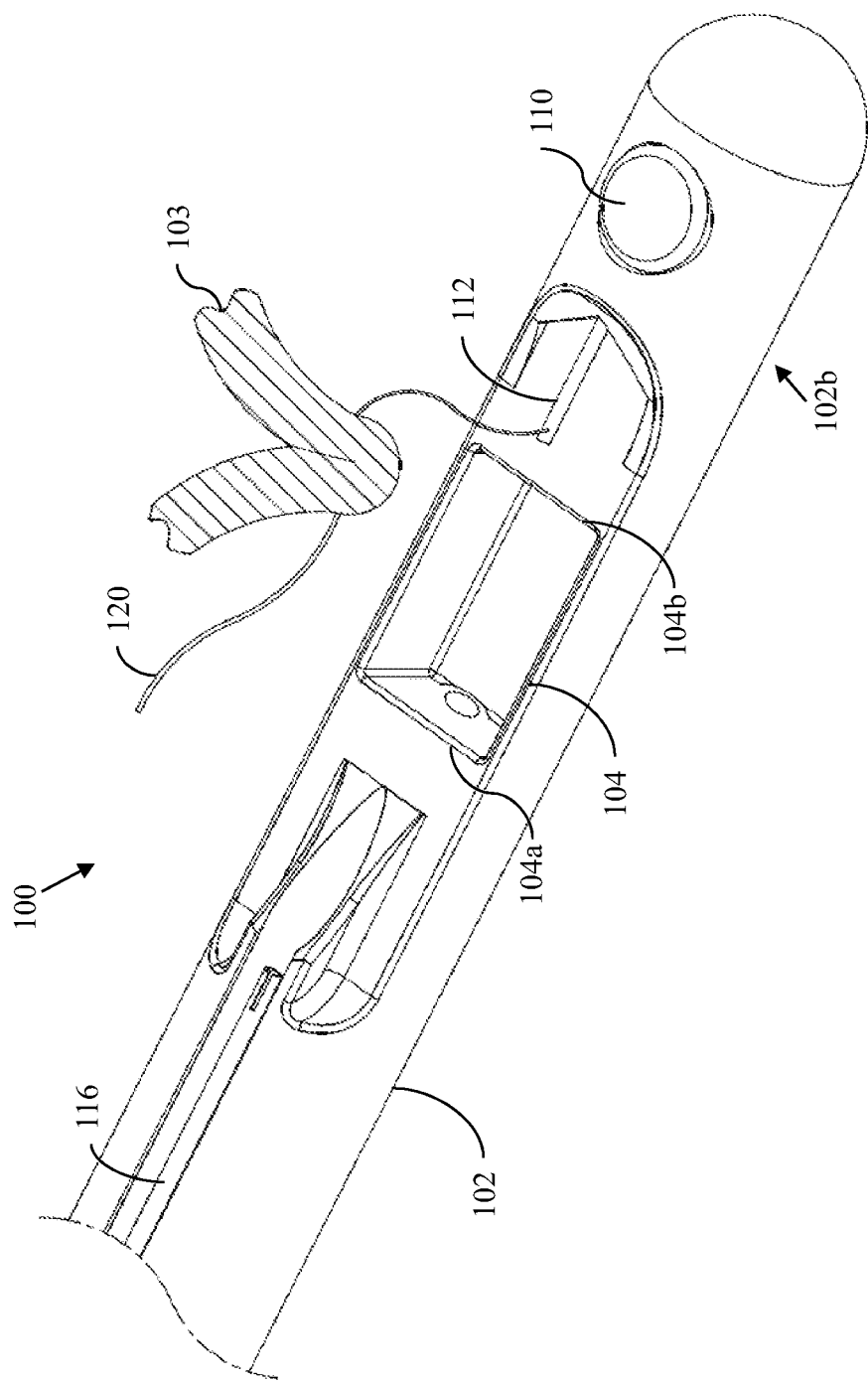
FIG. 1M illustrates an enlarged view of the distal end of the suturing device when the operating handle is in a fully retracted position, in accordance with an exemplary embodiment of the present disclosure.
Figure 1N:
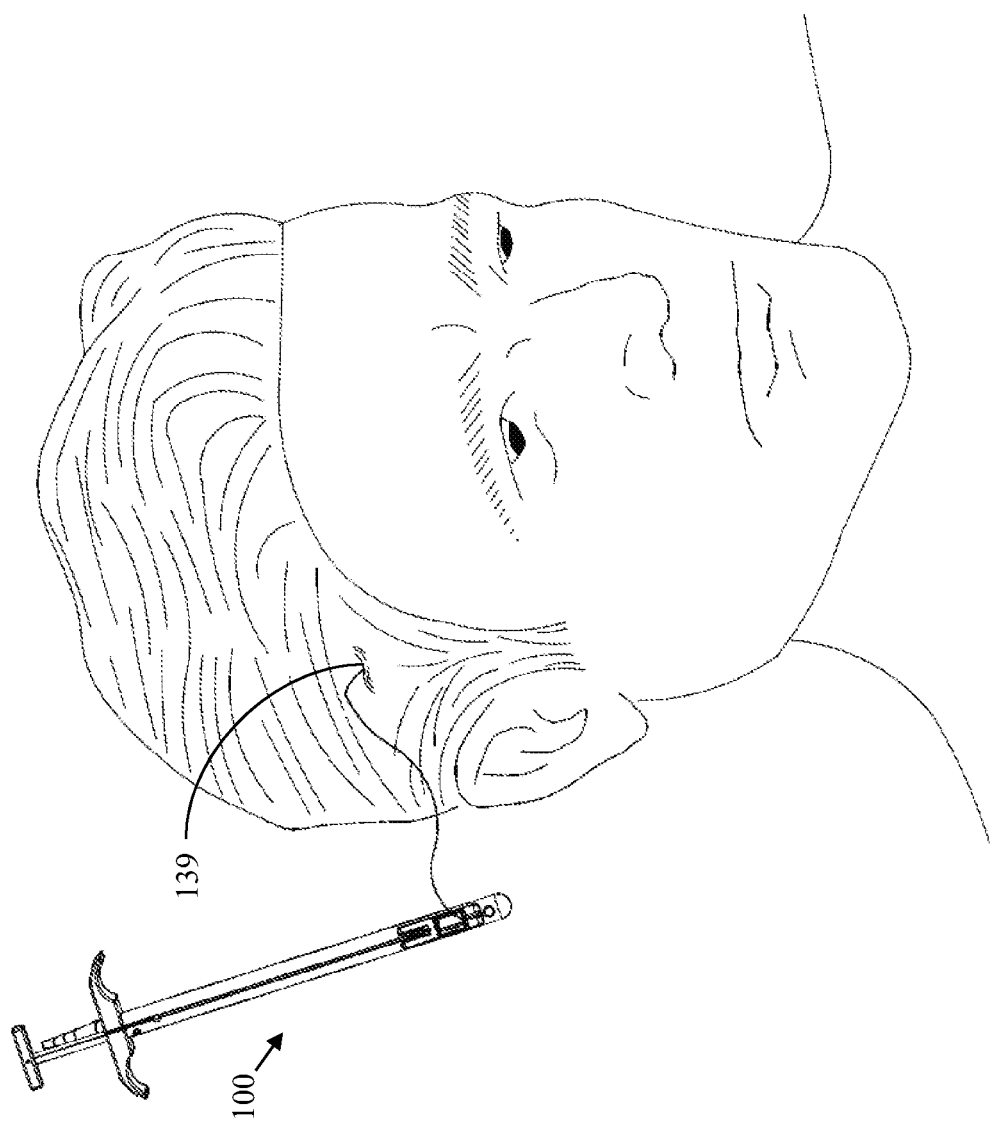
FIG. 1N illustrates a representative view of the face of the patient, with the slit incision shown therein, through which the suturing device is removed, in accordance with an exemplary embodiment of the present disclosure.

Once the needle 112 and the suture 120 have been passed through the tissue 103 and the stitch has been made, the operating handle 118 is retracted such that the needle pusher 116 moves from the fully advanced position to the intermediate position while the needle 112 remains captured by the needle capturing assembly 110 and the tissue 103 remains captured by the cavity 104. As a result, the needle 112 disengages from the needle pusher 116. Full retraction of the operating handle 118 such that the needle pusher 116 moves from the intermediate position to the fully retracted position causes the blocking member 124 to also retract such that it no longer blocks the first aperture 126. As a result, the vacuum is no longer applied to the cavity 104 and the suctioned tissue 103 is released from the cavity 104 while the suture 120 remains passed through the tissue 103 (as shown in FIG. 1M). At this point, the suturing device 100 (with the suture still passed through the tissue 103) is removed from the slit incision 139 of the patient as shown in FIG. 1N. The user may then remove the needle 112 from the needle capturing assembly 110, for example using a hemostat or forceps or another device known to those skilled in the art, and perform a second suture pass without the suturing device 100, again, for example, using a conventional needle holder or another device known to those skilled in the art, in order to make one or more additional passes through the tissue 103 and/or another tissue. Alternatively, the user may remove the needle 112 from the needle capturing assembly 110 and reposition the needle 112 in the needle pusher 116, again, for example, using forceps, and use the suturing device 100 in order to make one or more additional passes through the tissue 103 and/or another tissue as described above.

Figure 1O:
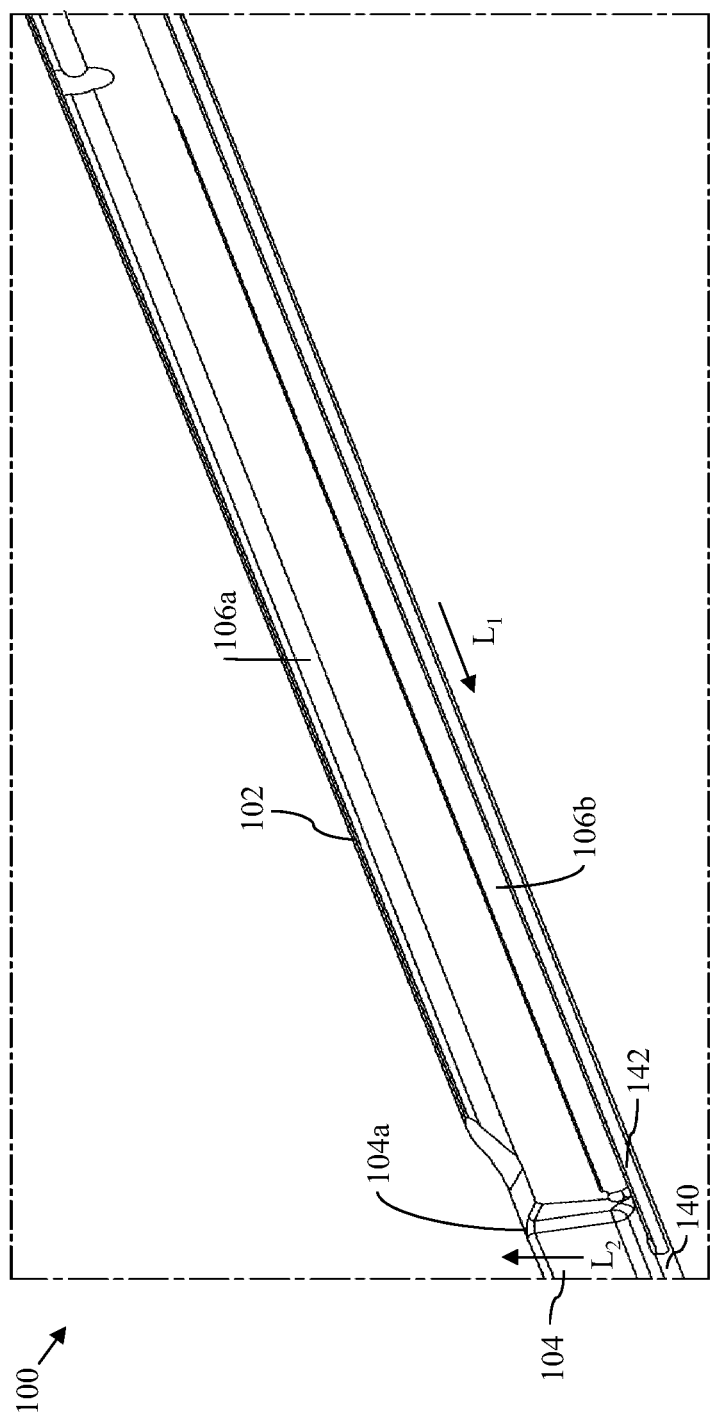
FIG. 1O illustrates a cross-sectional side view of the suturing device with a light channel, in accordance with an exemplary embodiment of the present disclosure.

FIG. 1O illustrates an enlarged cross-sectional side view of the suturing device 100, in accordance with an exemplary embodiment of the present disclosure. In a preferred embodiment, light from a light source (not shown) may be used to illuminate tissue (e.g., the tissue 103) when the suturing device 100 is inserted within a body. Such illumination can help the user guide the suturing device 100 within the body and ensure that the cavity 104 is in a desired position, for example, prior to application of a vacuum to the cavity 104. For example, illumination of tissue may be desired/required in non-endoscopic procedures where the surgeon has limited or no visual contact with the area(s) at or near the desired suturing site. Preferably, a light channel 140 is included within the elongated member 102 and runs parallel to the suction channel 106b and along the length of the suturing device 100, for example from the proximal end 102a to midway of the cavity 104. In one embodiment, the light channel 140 is dimensioned to accommodate a light source within the light channel 140. For example, a laser-emitting fiber optic cable running along a direction Li through the length of the light channel 140 from a laser source (not shown) external to the suturing device 100 may be used. Alternatively, an LED may be positioned beneath the bottom surface of the cavity 104 (opposite the open side of the cavity 104) with electrical connections running through the length of the light channel 140 to a power source (not shown) external to the suturing device 100. Light from the light source is preferably directed in a direction L2 towards the open side of the cavity 104 such that the light exits the cavity 104 towards the tissue to be illuminated. Preferably, the properties (e.g., wavelength and/or power) of the emitted light are such that the light may be seen by the user of the suturing device 100 through the subject's skin indicating the location of the cavity 104 within the subject's body. In order to allow for the light from the light source to pass through the bottom surface of the cavity 104 (opposite the open side), at least the portion of the elongated member 102 forming the bottom surface of the cavity 104 should be constructed using a translucent or transparent material, such as a translucent or transparent glass, polymer, plastic, or the like. The material used could also be a light amplifying material or a lens. In a non-limiting example, as shown in FIG. 1O, a right-angled fiber optic cable 142 may be used as the light source to shine light along the direction $L_2$. The right-angled fiber optic cable 142 running along the direction $L_1$ through the length of the light channel 140 shines light along the direction $L_2$. In another non-limiting example, a lens/mirror arrangement may be installed below the bottom surface of the cavity 104 at a suitable angle so as to enable incident light to be reflected along the direction $L_2$. Alternatively, the light channel 140 itself can be constructed as an optical waveguide to guide to carry light from an external light source (e.g., an LED) coupled to the end of the light channel 140 and direct the light along the direction $L_2$.

FIGS. 2A-2D illustrate perspective, exploded, front perspective, and an enlarged rear perspective views, respectively, of an apparatus 200 for use with the suturing device 100 (with modifications to the suturing device 100 to accommodate the apparatus 200 as described below), in accordance with an exemplary embodiment of the present disclosure. The apparatus 200 may be used to release the needle 112 from the needle capturing assembly 110 of the suturing device 100 and reposition the needle 112 so as to be reengaged by the needle pusher 116 of the suturing device 100. The apparatus 200 and its various parts may be made of a material or materials designed to ensure proper functioning of the apparatus 200 and clamping of the needle 112. Such materials may include polymers, composites, metals or the like.

The apparatus 200 includes a base 202 dimensioned to fit within the cavity 104 of the suturing device 100, and a clamp 204 coupled to the base 202 so as to be moveable in directions X and X'. As described in more detail below, the clamp 204 is operable to clamp the end of the needle 112 extending from the needle capturing assembly 110 when the needle 112 is captured by the needle capturing assembly 110. The base 202 may include a locking mechanism that facilitates secure lodging of the base 202 within the cavity 104. In a non-limiting example, the base 202 is shown to include first and second locking members 206a and 206b. The first and second locking members 206a and 206b may be dimensioned to mate with corresponding structures formed on or carved into the surface of inside walls of the cavity 104 (for example, as described below in connection with FIG. 3A), thereby locking the base 202 in the cavity 104 in a "snap-fit" fashion when the base 202 is pressed into the cavity 104. Alternatively, the base 202 can be securely lodged in the cavity 104 using, for example, a pin and groove arrangement other structure(s) known to those skilled in the art.

The clamp 204 includes a first lever 208a and a second lever 208b. The first lever 208a includes a jaw portion 210a and a handle portion 212a and the second lever 208b includes a jaw portion 210b and a handle portion 212b. The second lever 208b is secured to the first lever 208a by a pivot pin 214 such that the jaw portion 210b of the second lever 208b is rotatable about the axis of the pivot pin 214 enabling relative motion between the first and second levers 208a and 208b. By squeezing on the handle portions 212a and 212b of the first and second levers 208a and 208b, the jaw portions 210a and 210b may be operated to clamp the end of the needle 112.

Figure 2A:
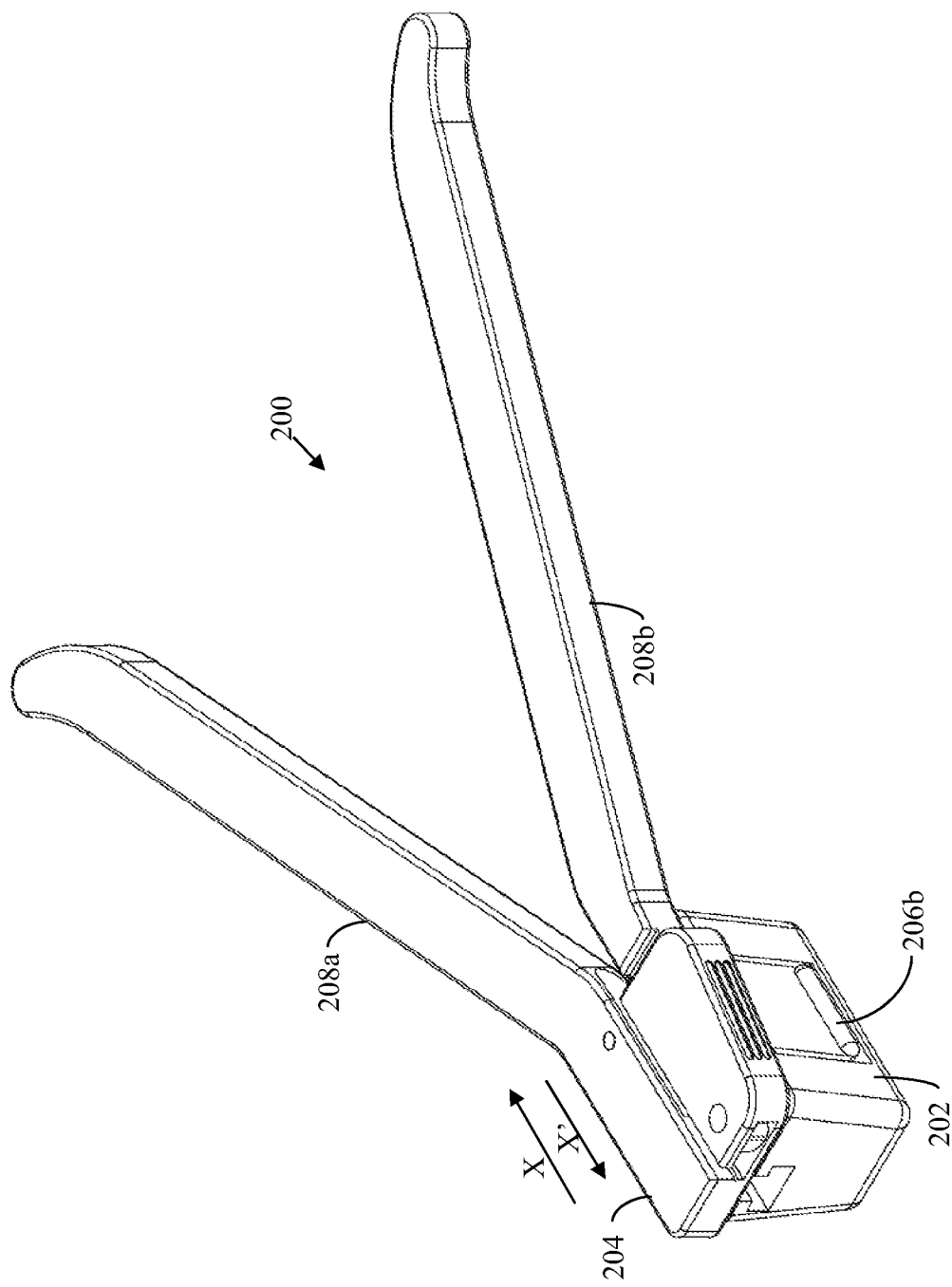
FIG. 2A illustrates a perspective side view of an apparatus for use with the suturing device, in accordance with an exemplary embodiment of the present disclosure
Figure 2B:
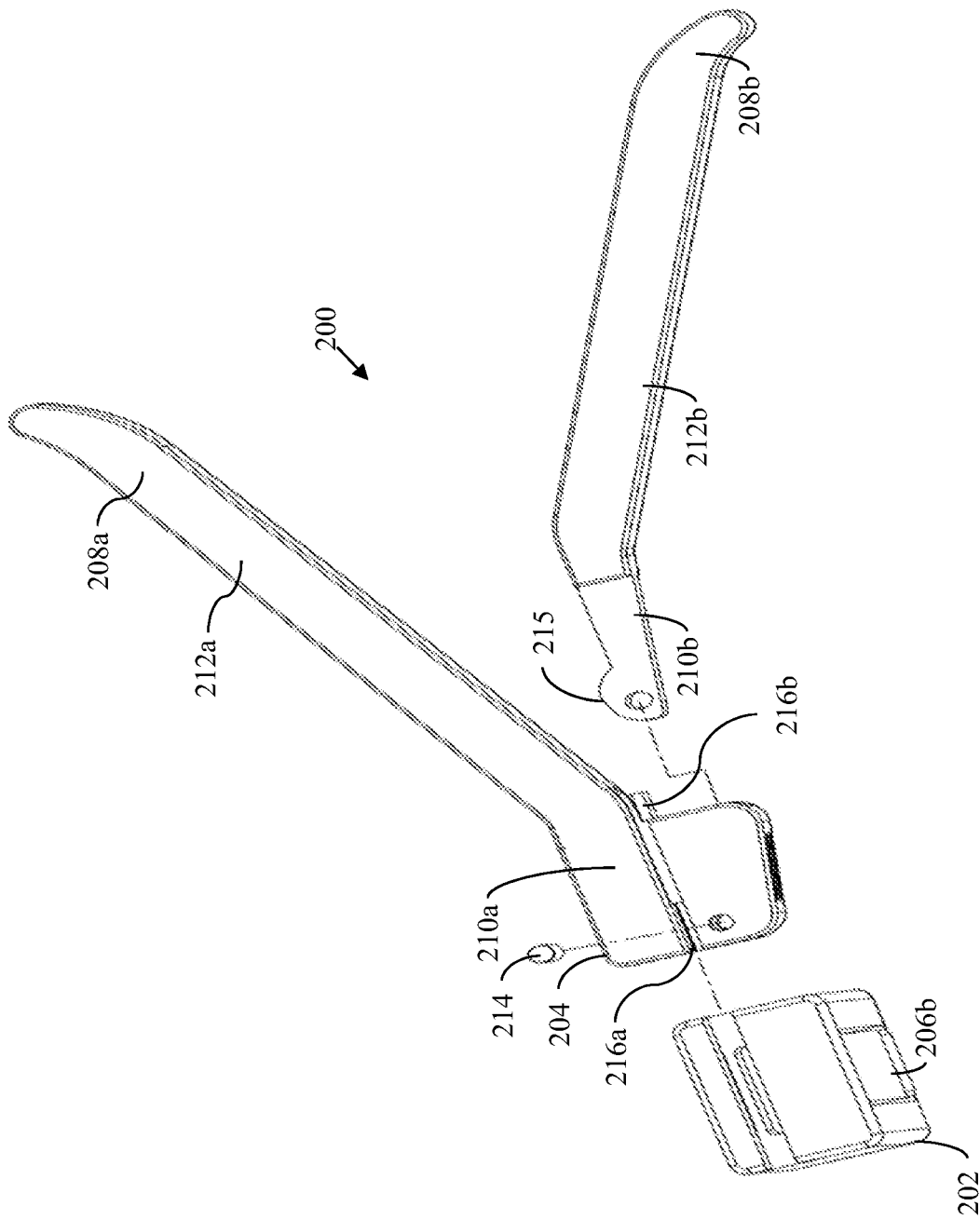
FIG. 2B illustrates an exploded view of the apparatus, in accordance with an exemplary embodiment of the present disclosure.

In one embodiment, the jaw portion 210a of the first lever 208a and/or the jaw portion 210b of the second lever 208b has a profile that facilitates clamping of the needle 112 between the jaw portions 210a and 210b. For example, a profile 215 of the jaw portion 210b may be of curve shape as shown in FIG. 2B. Alternatively, the profile 215 may be of any other shape that facilitates clamping of the end of the needle 112 by the jaw portions 210a and 210b. One or both of the jaw portion 210a and the jaw portion 210b may also include ridges or other surface textures and/or be made of certain materials, e.g., rubber, to facilitate clamping of the needle 112. The first lever 208a is preferably designed to include a first channel 216a and a second channel 216b. The second channel 216b is preferably wider than the first channel 216a and is preferably aligned with the first channel 216a (as shown in FIG. 2D). The first channel 216a is dimensioned and positioned to receive the needle 112 when the apparatus 200 is in use. The second channel 216b is dimensioned and positioned to receive the needle pusher 116 when the apparatus 200 is in use.

Figure 2C:
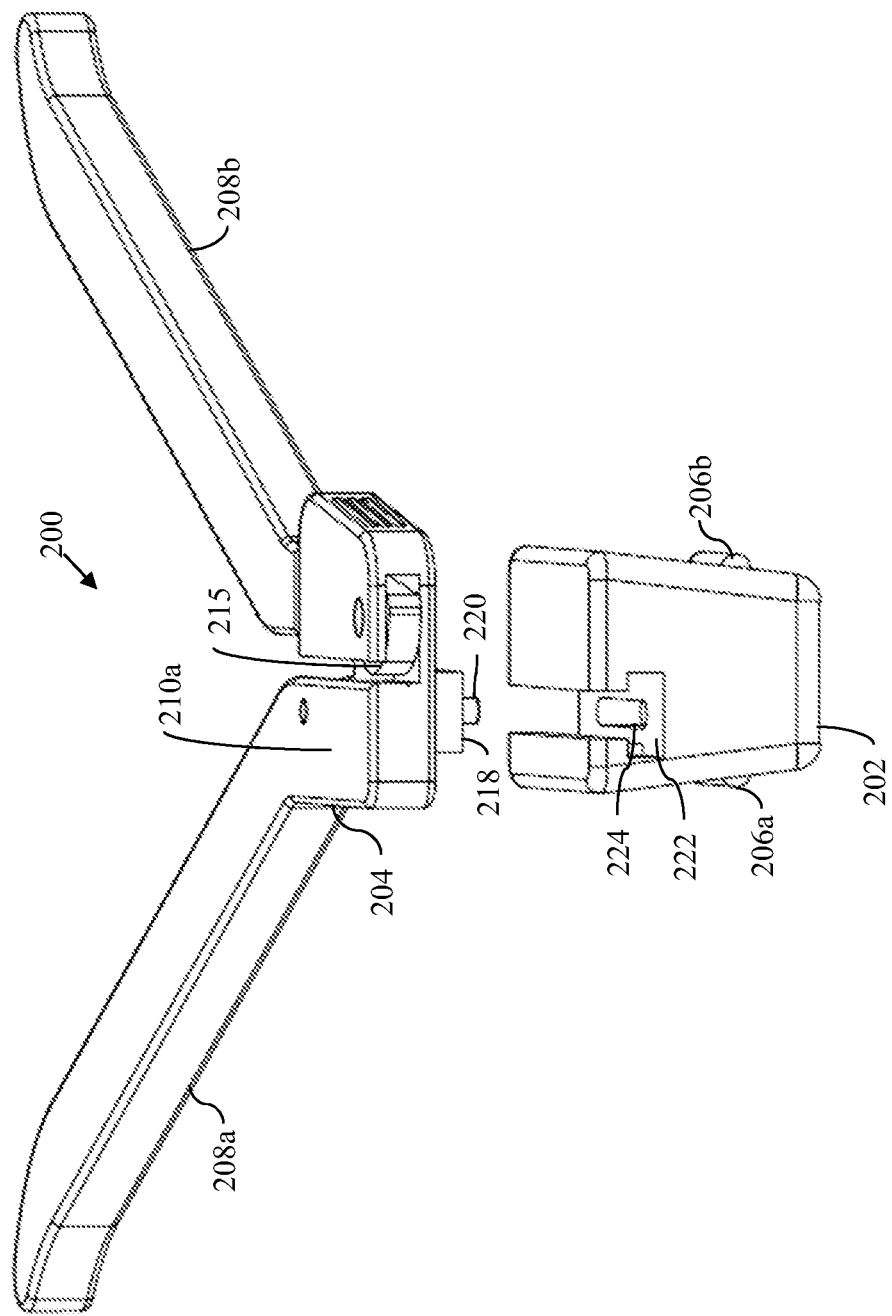
FIG. 2C illustrates a perspective front view of the apparatus, in accordance with an exemplary embodiment of the present disclosure.
Figure 2D:
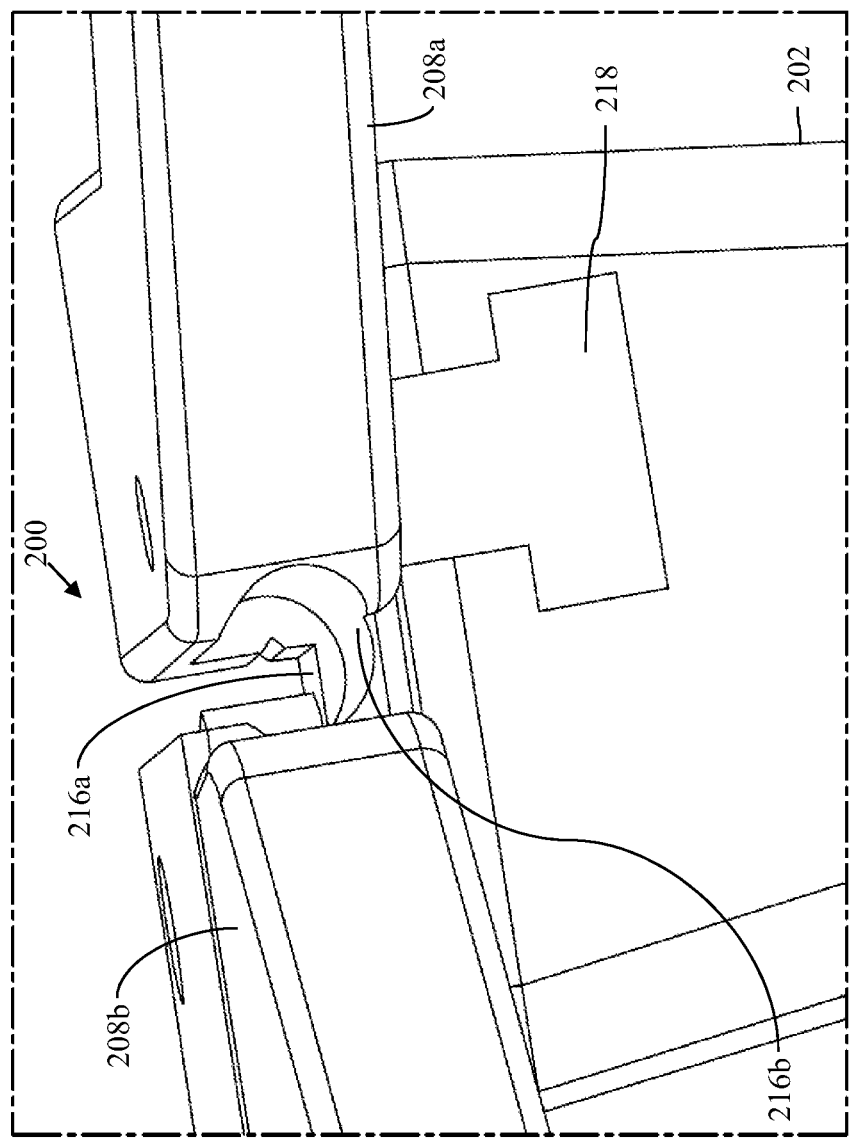
FIG. 2D illustrates an enlarged rear perspective view of the apparatus, in accordance with an exemplary embodiment of the present disclosure.

As shown in FIG. 2C, the first lever 208a includes a protrusion 218 that extends outwardly from a bottom surface of the first lever 208a. The protrusion 218 has a cross section that generally looks like the letter "T" (as shown in FIG. 2D) and is provided with an extended pin 220. The protrusion 218 is slidably positioned into a groove 222, having a cross section that generally looks like the inverted letter "T", formed on a top surface of the base 202. Formed within the groove 222 is a guide channel 224 to accommodate the extended pin 220. The guide channel 224 is dimensioned and positioned to allow the extended pin 220 to horizontally slide within the guide channel 224. Although the protrusion 218 and the groove 222 are shown to have a "T" shaped cross-section, they may have a variety of other cross-sectional shapes to allow the clamp 204 to slide with respect to and remained engaged with the base 202.

The length of the guide channel 224 is selected to define a range of positions that the clamp 204 can occupy with respect to the base 202. For example, the length of the guide channel 224 may be such that it allows the clamp 204 to be slid from a first position to a second position and vice-versa with respect to the base 202. In the first position, the clamp 204 is positioned to be operable to clamp the end of the needle 112 extending from the needle capturing assembly 110. The clamp 204, while clamping the needle 112, may be moved from the first position to the second position to disengage the needle 112 from the needle capturing assembly 110.

Operation of the apparatus 200 is explained in greater detail in conjunction with FIGS. 3A-3E.

Figure 3A:
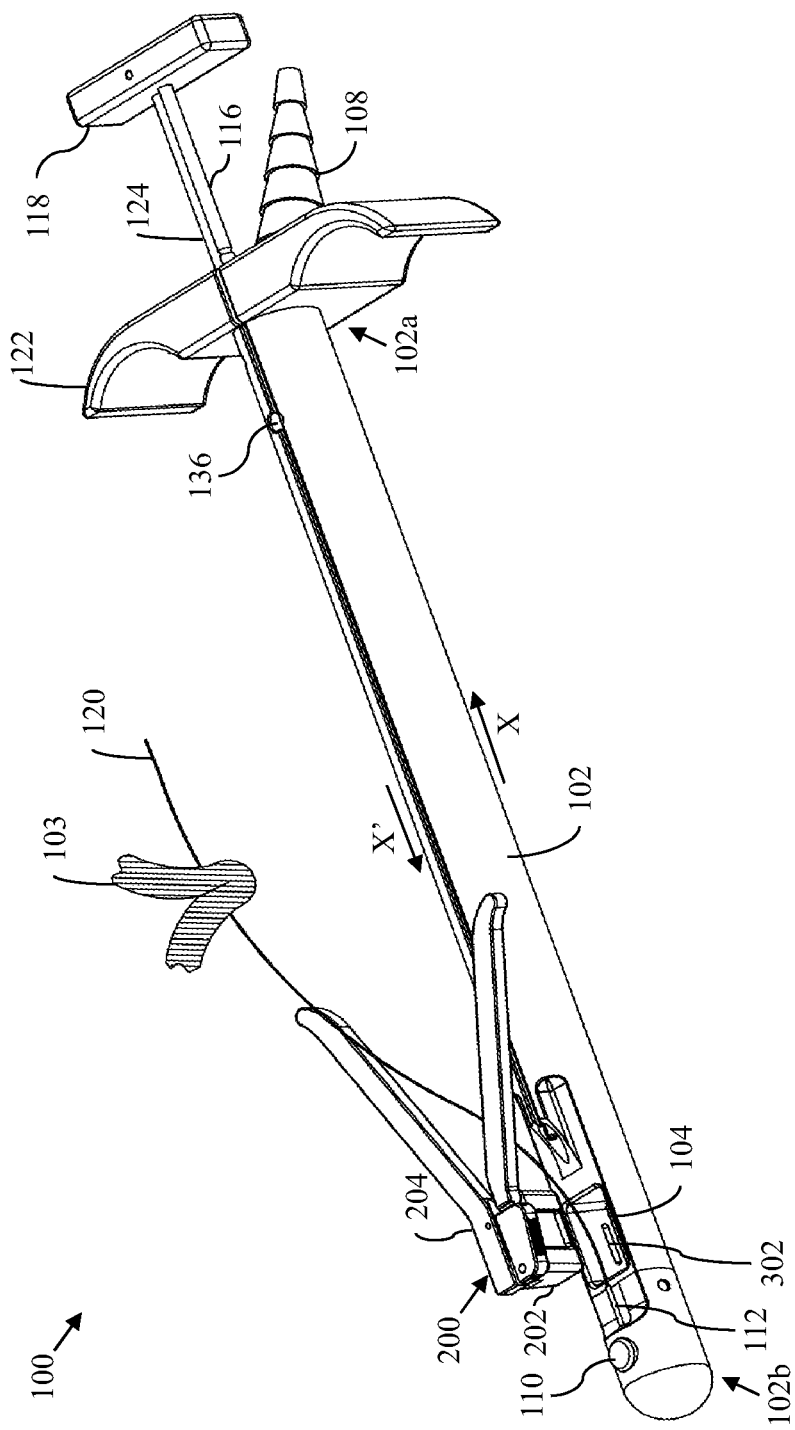
FIG. 3A illustrates a perspective view of the suturing device and the apparatus, in accordance with an exemplary embodiment of the present disclosure.
Figure 3B:
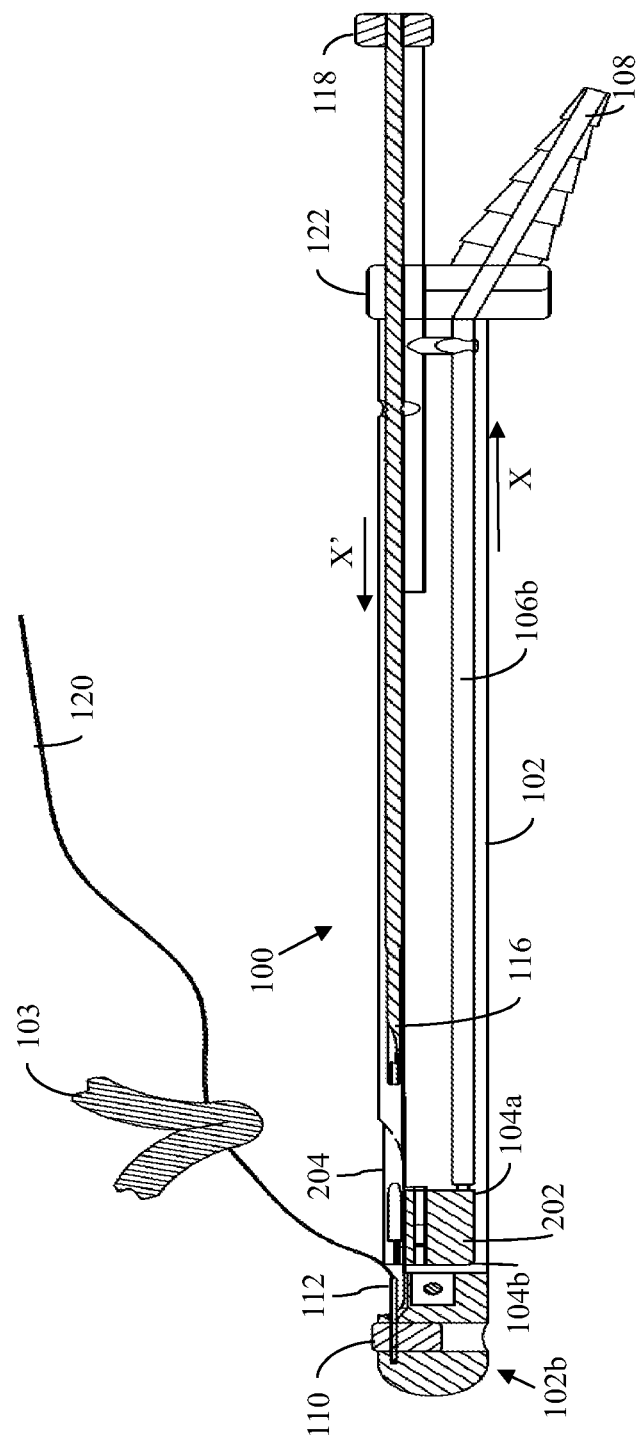
FIG. 3B illustrates a cross-sectional side view of the suturing device coupled with the apparatus, in accordance with an exemplary embodiment of the present disclosure.
Figure 3C:
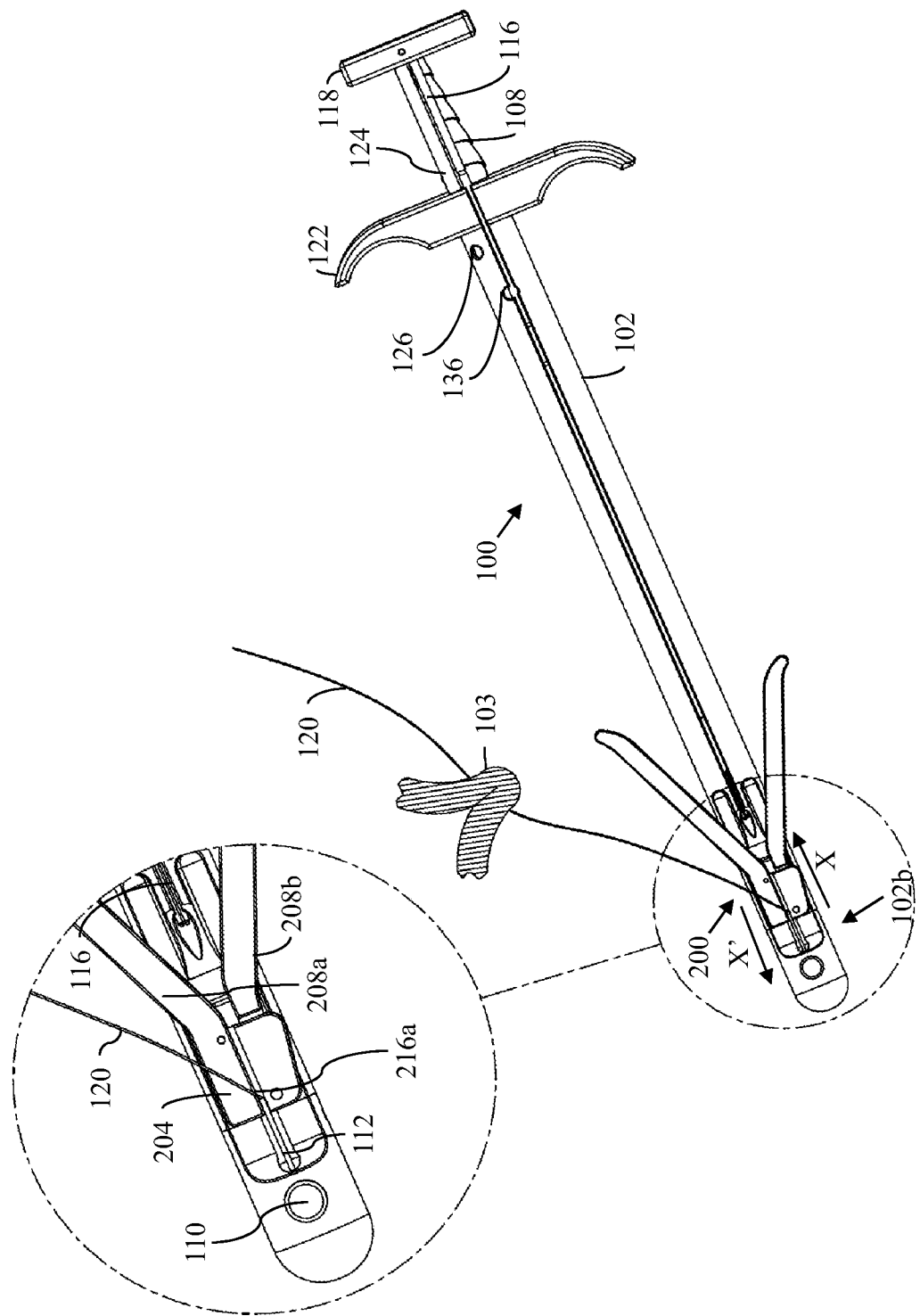
FIG. 3C illustrates a perspective view and an enlarged perspective view of the distal end of the suturing device coupled with the apparatus when the apparatus is engaged with a needle, in accordance with an exemplary embodiment of the present disclosure.

As shown in FIG. 3A, the needle 112 and suture 120 have been passed through the tissue 103 and the operating handle 118 has been retracted from the fully advanced position to the fully retracted position, thereby retracting the needle pusher 116 such that it disengages from the needle 112 while the needle 112 remains captured by the needle capturing assembly 110 and also thereby retracting the blocking member 124 such that it no longer blocks the first aperture 126. As a result, the vacuum is no longer applied to the cavity 104 and the suctioned tissue 103 is released from the cavity 104 while the suture 120 remains passed through the tissue 103. At this point, the suturing device 100 is removed from the body and the base 202 of the apparatus 200 is placed within the cavity 104. It should be appreciated that, in the fully retracted position, the needle pusher 116 is sufficiently retracted so as to prevent the needle pusher 116 from interfering with the coupling between the apparatus 200 and the cavity 104 when the base 202 of the apparatus 200 is inserted into the cavity 104. Further, because the entirety of the needle 112 has passed across the second wall 104b of the cavity 104, the needle 112 does not interfere with the coupling between the apparatus 200 and the cavity 104 when the base 202 of the apparatus 200 is inserted into the cavity 104. When the base 202 of the apparatus 200 is placed in the cavity 104, the first and second locking members 206a and 206b may interface with corresponding structures on and/or formed in walls of the cavity to securely lock the base 202 within the cavity 104 as described above. For example, the corresponding structures may be a first slot (not shown) and a second slot 302 formed in the side walls of the cavity 104 and dimensioned and positioned to engage with the first and second locking members 206a and 206b, respectively. FIG. 3B illustrates a cross-sectional side view of the suturing device 100 when the base 202 of the apparatus 200 is placed in the cavity 104 and secured by the engagement of the first and second locking members 206a and 206b with the first slot and the second slot 302, respectively FIG. 3C illustrates an enlarged perspective view of the distal end 102b of the apparatus 200 coupled with the suturing device 100, in accordance with an exemplary embodiment of the present disclosure. Once the base 202 is secured in the cavity 104, a user of the suturing device 100 slides the clamp 204 with respect to the base 202 in the direction X', for example by pushing on the first and second levers 208a and 208b. As the clamp 204 is moved in the direction X', the end of the needle 112 extending from the needle capturing assembly 110 is received in the first channel 216a of the clamp 204 as shown in the enlarged diagram of FIG. 3C. Once the end of the needle 112 extending from the needle capturing assembly 110 is positioned in the first channel 216a of the clamp 204, the second lever 208b is moved relative to the first lever 208a such that the jaw portion 210b of the second lever 208b is moved relative to the jaw portion 210a of the first lever 208a to clamp the needle 112. Once the needle 112 is clamped by the jaw portion 210a and the jaw portion 210b with sufficient clamping force, the clamp 204 may be moved with respect to the base 202 in the direction X, for example, by pulling on the first and second levers 208a and 208b, while maintaining the clamping force on the needle 112. In this manner, the needle 112 may be extracted from the needle capturing assembly 110.

Figure 3D:
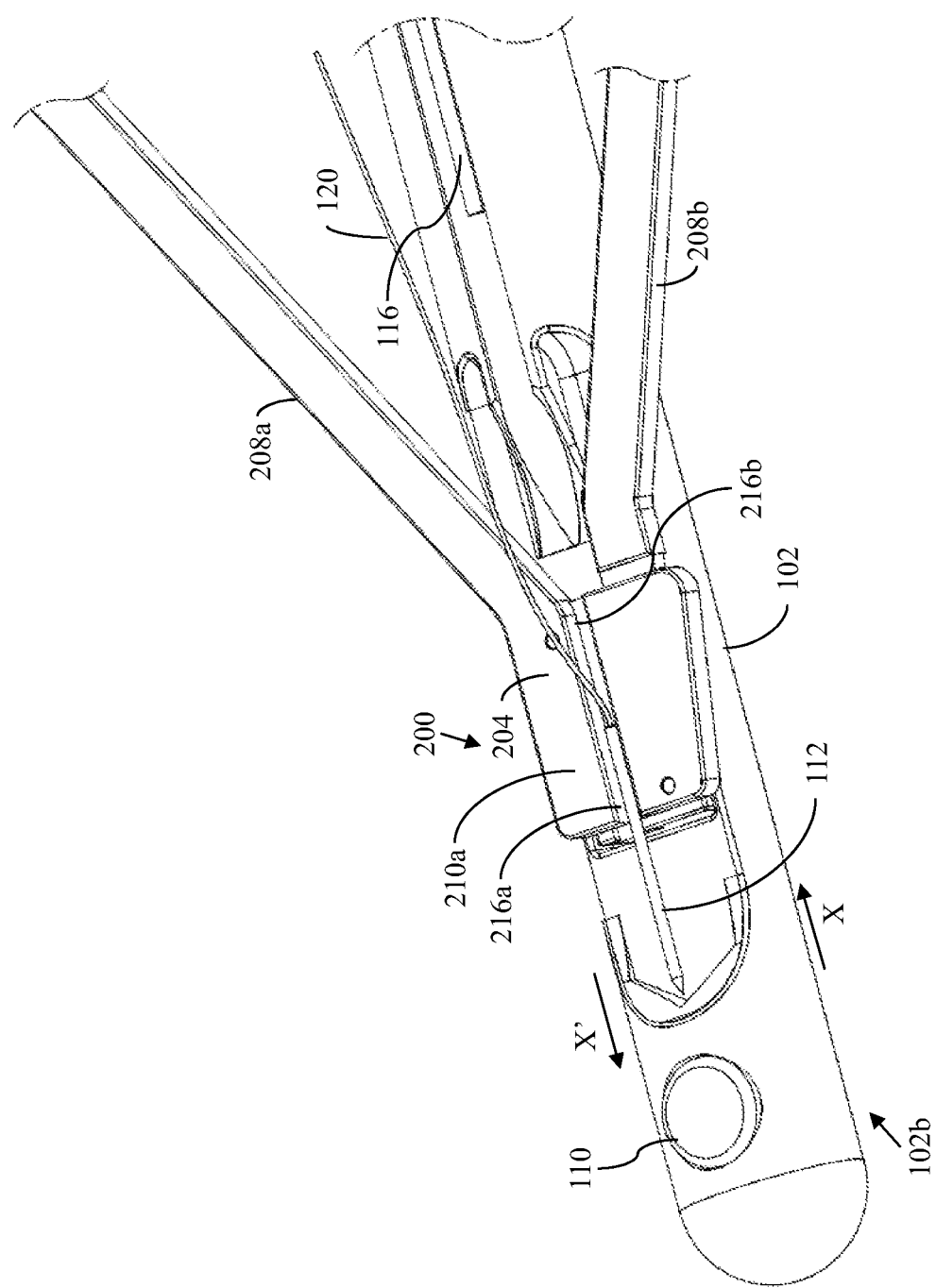
FIG. 3D illustrates an enlarged perspective view of suturing device coupled with the apparatus when the needle is released from a needle capturing member, in accordance with an exemplary embodiment of the present disclosure.

FIG. 3D illustrates an enlarged view of the distal end 102b of the suturing device 100 coupled with the apparatus 200, in accordance with an exemplary embodiment of the present disclosure. As shown in FIG. 3D, the clamp 204 has been moved with respect to the base 202 in the direction X, for example, by pulling on the first and second levers 208a and 208b to extract the needle 112 from the needle capturing assembly 110. The clamp 204 may then be further moved in the direction X to the second position to allow the needle pusher 116 to re-engage with the needle 112.

Figure 3E:
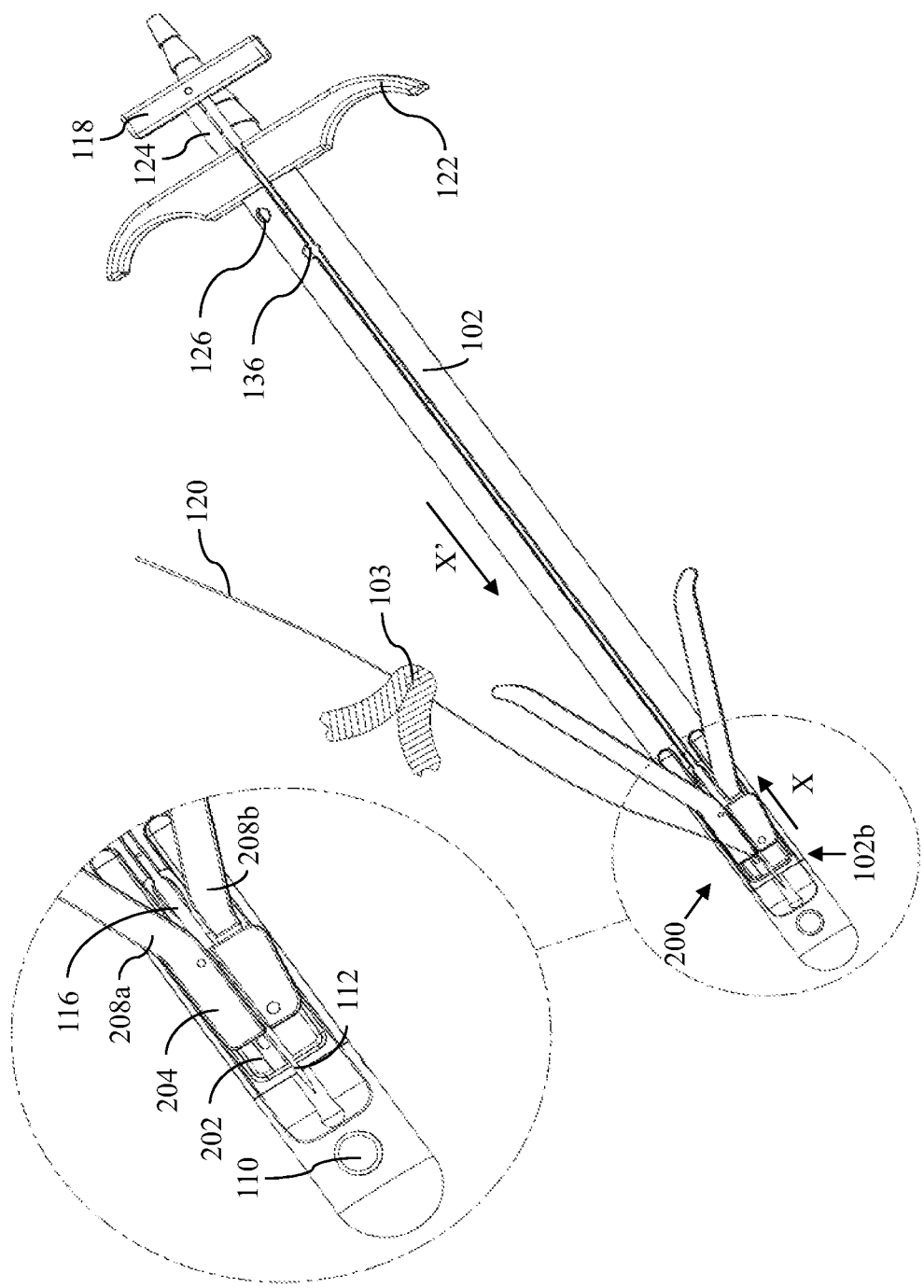
FIG. 3E illustrates a perspective view and an enlarged perspective view of the distal end of the suturing device coupled with the apparatus when the operating handle is in a partially advanced position, in accordance with an exemplary embodiment of the present disclosure.

FIG. 3E illustrates an enlarged perspective view of the distal end 102b of the apparatus 200 coupled with the suturing device 100 when the operating handle 118 has been moved to a partially advanced position subsequent to the extraction of the needle 112 from the needle capturing assembly 110 as described above in connection with FIGS. 3C and 3D. As shown in FIG. 3E, once the needle 112 has been extracted from the needle capturing assembly 110, the operating handle 118 may be progressively advanced from the fully retracted position towards the fixed handle 122 in the direction X, thereby advancing the needle pusher 116 until the needle pusher 116 is positioned with the second channel 216b and re-engages with the end of the needle 112 with the suture 120 attached thereto. Preferably, the needle pusher 116 is advanced until the second detent 132b of the needle pusher 116 engages with the ball 138b of the ball-spring detent mechanism 130 to create the audible and/or tactile feedback described above, such that the user is made aware that the needle pusher 116 has re-engaged the end of the needle 112. Following re-engagement of the needle 112 with the needle pusher 116, the operating handle 118 may be retracted towards the fully retracted position such that the needle 112 is returned to the position shown in FIG. 1A. Once the needle 112 is in the position shown in FIG. 1A, the user of the suturing device 100 may de-couple the apparatus 200 from the cavity 104, reposition the suturing device 100 within the subject's body through, for example, the same incision or another incision, and re-pass the needle 112 and the suture 120 through the tissue 103 previously sutured (or another tissue) and create a second stitch. It should be appreciated that by repeating the foregoing procedure, the suturing device 100 may be operated to make multiple passes of the needle 112 and the suture 120 through tissue 103 (or another tissue) and thereby make multiple stitches using the needle 112 and the suture 120.

Figure 4A:
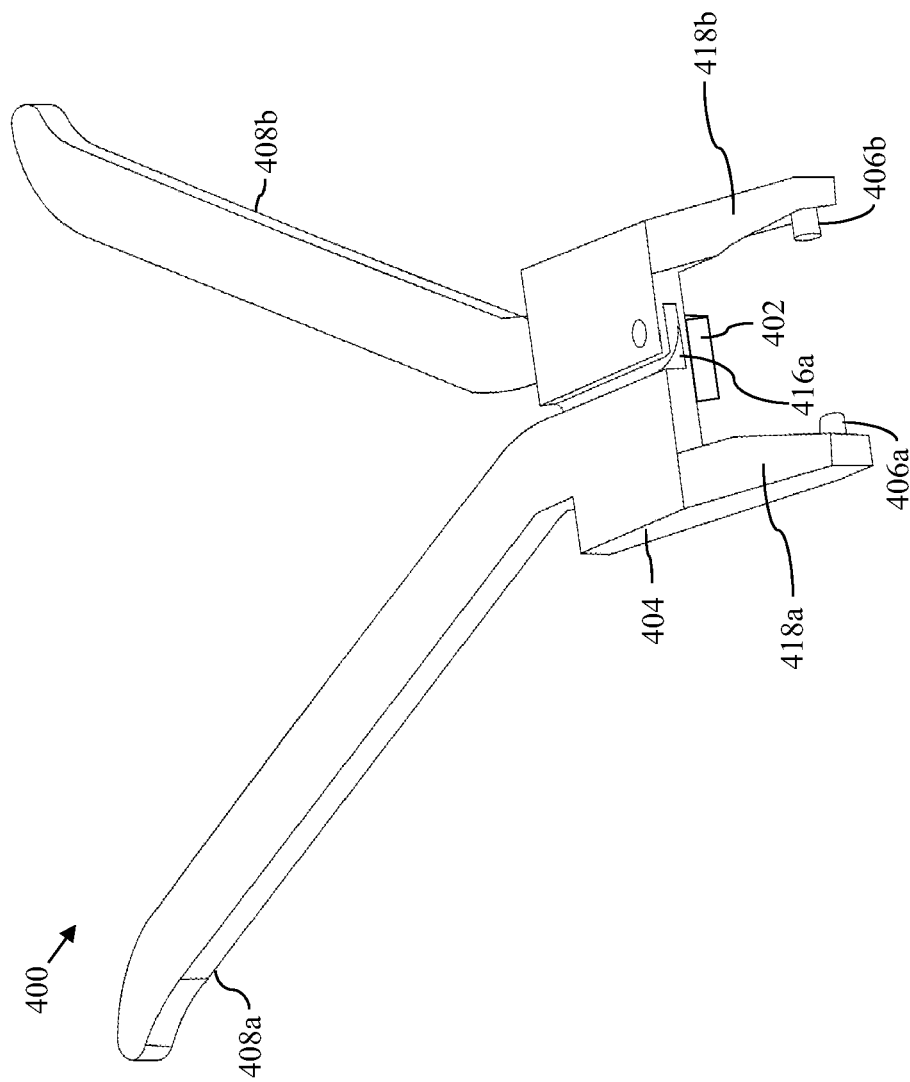
FIG. 4A illustrates a perspective view of an apparatus for use with a suturing device, in accordance with an exemplary embodiment of the present disclosure.
Figure 4B:
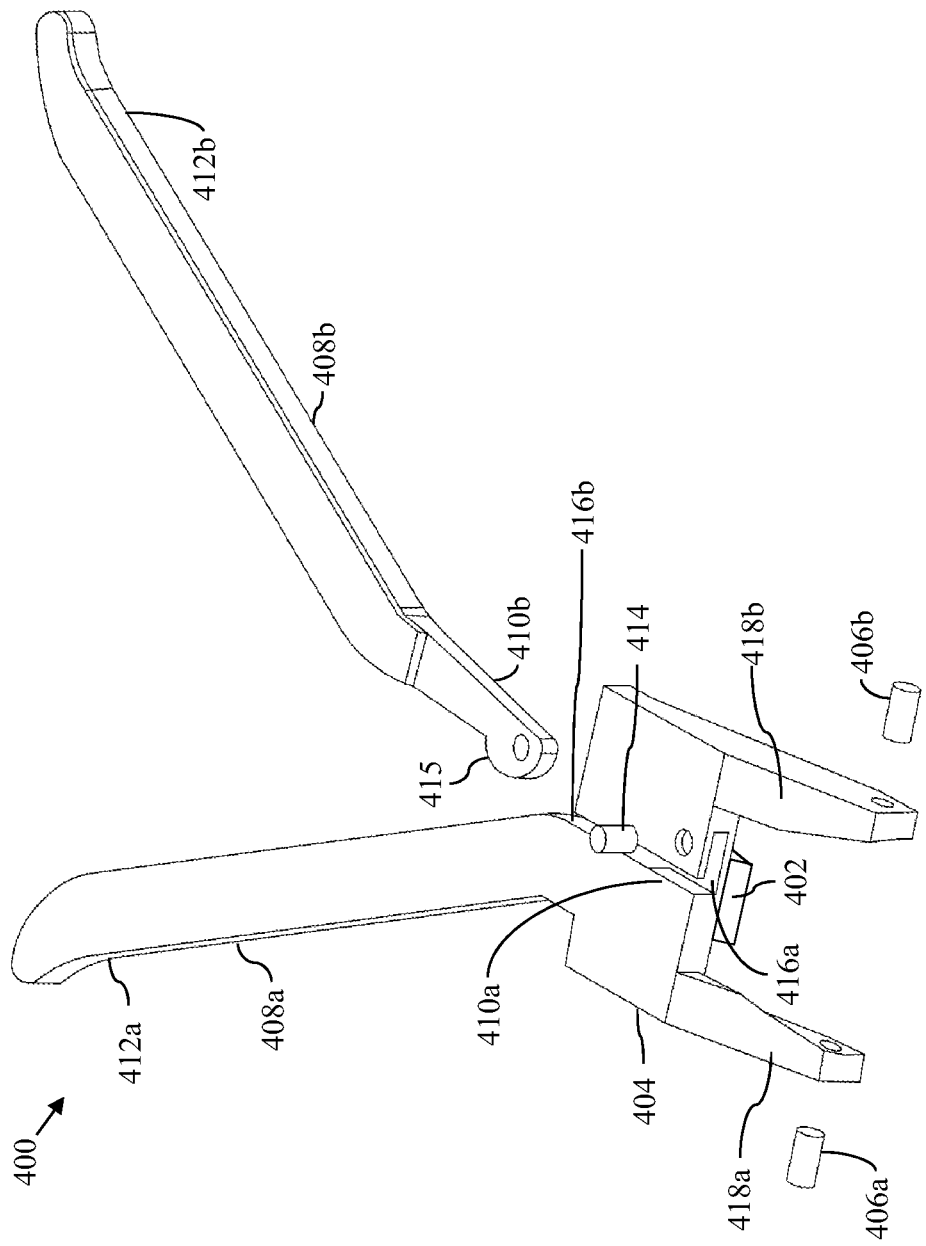
FIG. 4B illustrates an exploded view of the apparatus, in accordance with an exemplary embodiment of the present disclosure.
Figure 4C:
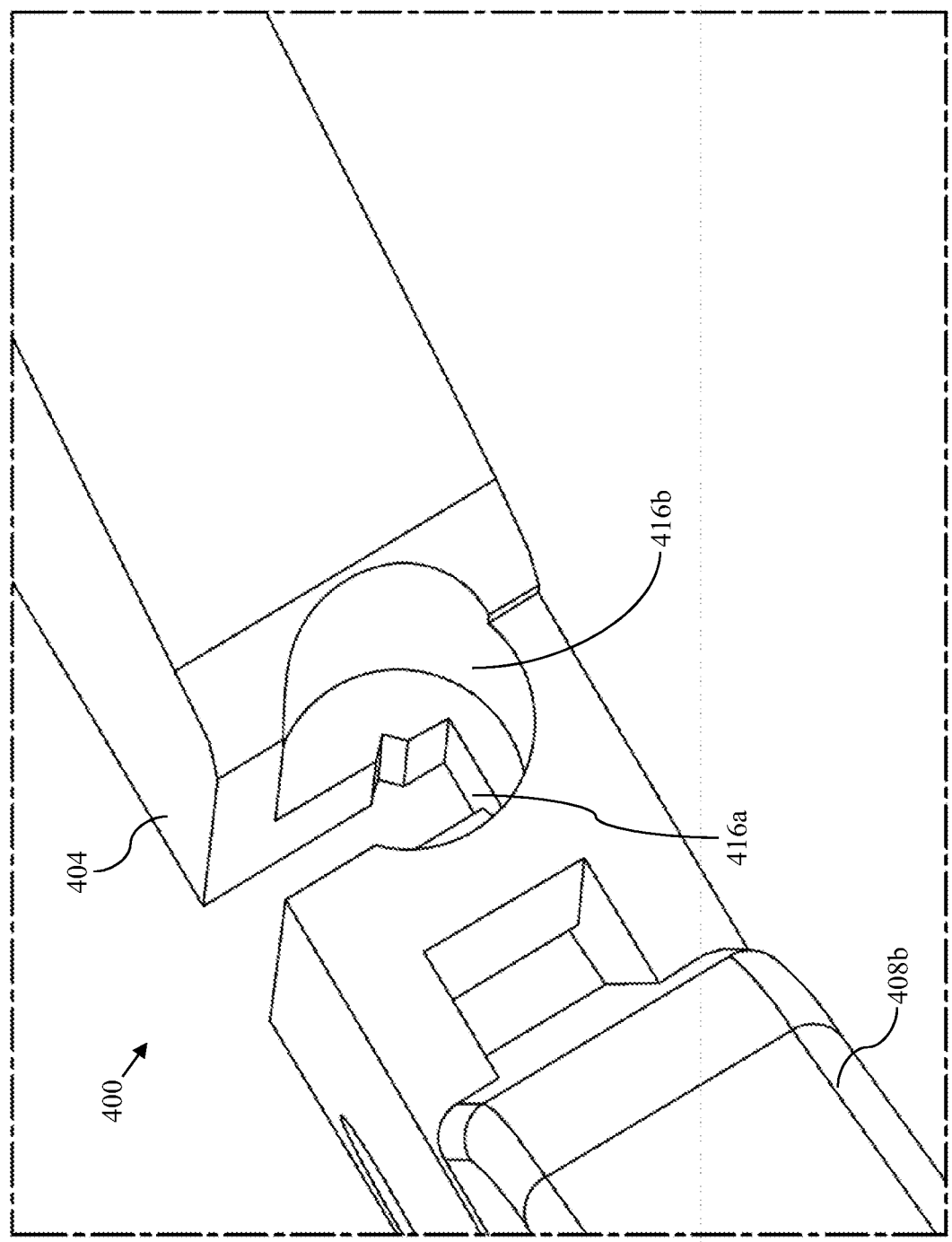
FIG. 4C illustrates an enlarged rear perspective view of the apparatus, in accordance with an exemplary embodiment of the present disclosure.

FIGS. 4A-4C illustrate top perspective, exploded, and rear perspective views, respectively, of an apparatus 400 for use with a suturing device 500 (see FIGS. 5A and 5B) to release the needle 112 from the needle capturing assembly 110 of the suturing device 500 and reposition the needle 112 so as to be reengaged by the needle pusher 116 of the suturing device 500 in accordance with an exemplary embodiment of the present disclosure. It should be appreciated that the suturing device 500 is structurally and functionally similar to the suturing device 100 of FIG. 1A, only modified to accommodate the apparatus 400 as described below. The apparatus 400 comprises a base 402 and a clamp 404. The clamp 404 is functionally similar to the clamp 204 of the apparatus 200, but is structurally modified with respect to the clamp 204, for example, in order to operate with the suturing device 500.

As shown in FIGS. 4A and 4B, the clamp 404 includes a first lever 408a and a second lever 408b. The first lever 408a includes a jaw portion 410a and a handle portion 412a and the second lever 408b includes a jaw portion 410b and a handle portion 412b. The second lever 408b is secured to the first lever 408a by a pivot pin 414 such that the jaw portion 410b of the second lever 408b is rotatable about the axis of the pivot pin 414 enabling relative motion between the first and second levers 408a and 408b. By squeezing on the handle portions 412a and 412b of the first and second levers 408a and 408b, the jaw portions 410a and 410b may be operated to clamp the end of the needle 112 as will be described in more detail below. In one embodiment, the jaw portion 410a of the first lever 408a and/or the jaw portion 410b of the second lever 408b has a profile that facilitates clamping of the end of the needle 112 between the jaw portions 410a and 410b. For example, a profile 415 of the jaw portion 410b may be of curve shape as shown in FIG. 4B. Alternatively, the profile 415 may be of any other shape that facilitates clamping of the end of the needle 112 by the jaw portions 410a and 410b. One or both of the jaw portion 410a and the jaw portion 410b may also include ridges or other surface textures and/or be made of certain materials, e.g., rubber, to facilitate clamping of the needle 112. The first lever 408a is preferably designed to include a first channel 416a and a second channel 416b. The second channel 416b is preferably wider than the first channel 416a and is preferably aligned with the first channel 416a (as shown in FIG. 4C). The first channel 416a is dimensioned and positioned to receive the needle 112 when the clamp 404 is in use. The second channel 416b is dimensioned and positioned to receive the needle pusher 116 when the apparatus 400 is in use.

As shown in FIG. 4A, the first lever 408a further includes first and second arms 418a and 418b having first and second guide pins 406a and 406b, respectively, extending therefrom. As further shown in FIG. 4A, the base 402 extends from a bottom surface of the first lever 408a. The base 402 is preferably dimensioned to fit within the cavity 104 of the suturing device 500 to allow sufficient room for the base 402 to slide within the cavity 104, for example, between first wall 104a (as shown in FIG. 5E) and second wall 104b (as shown in FIG. 5G). The movement of the base 402 within the cavity 104 defines movement of the apparatus 400 for removing the needle 112 from the needle capturing assembly 110 and re-engaging the needle 112 with the needle pusher 116 as will be described in more detail below in connection with FIGS. 5A-5H.

Figure 5A:
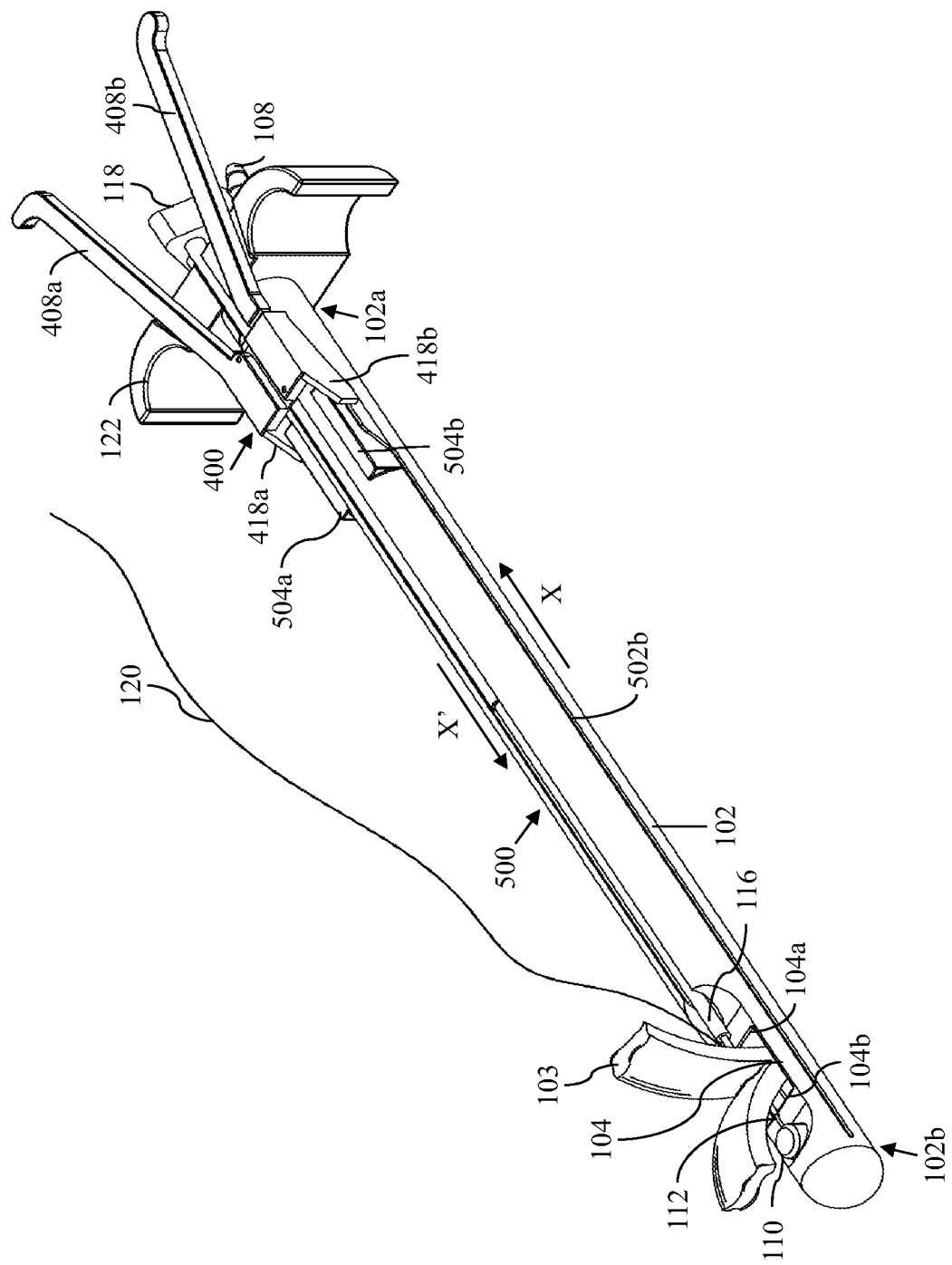
FIG. 5A illustrates a perspective view of the suturing device and the apparatus, in accordance with an exemplary embodiment of the present disclosure.
Figure 5B:
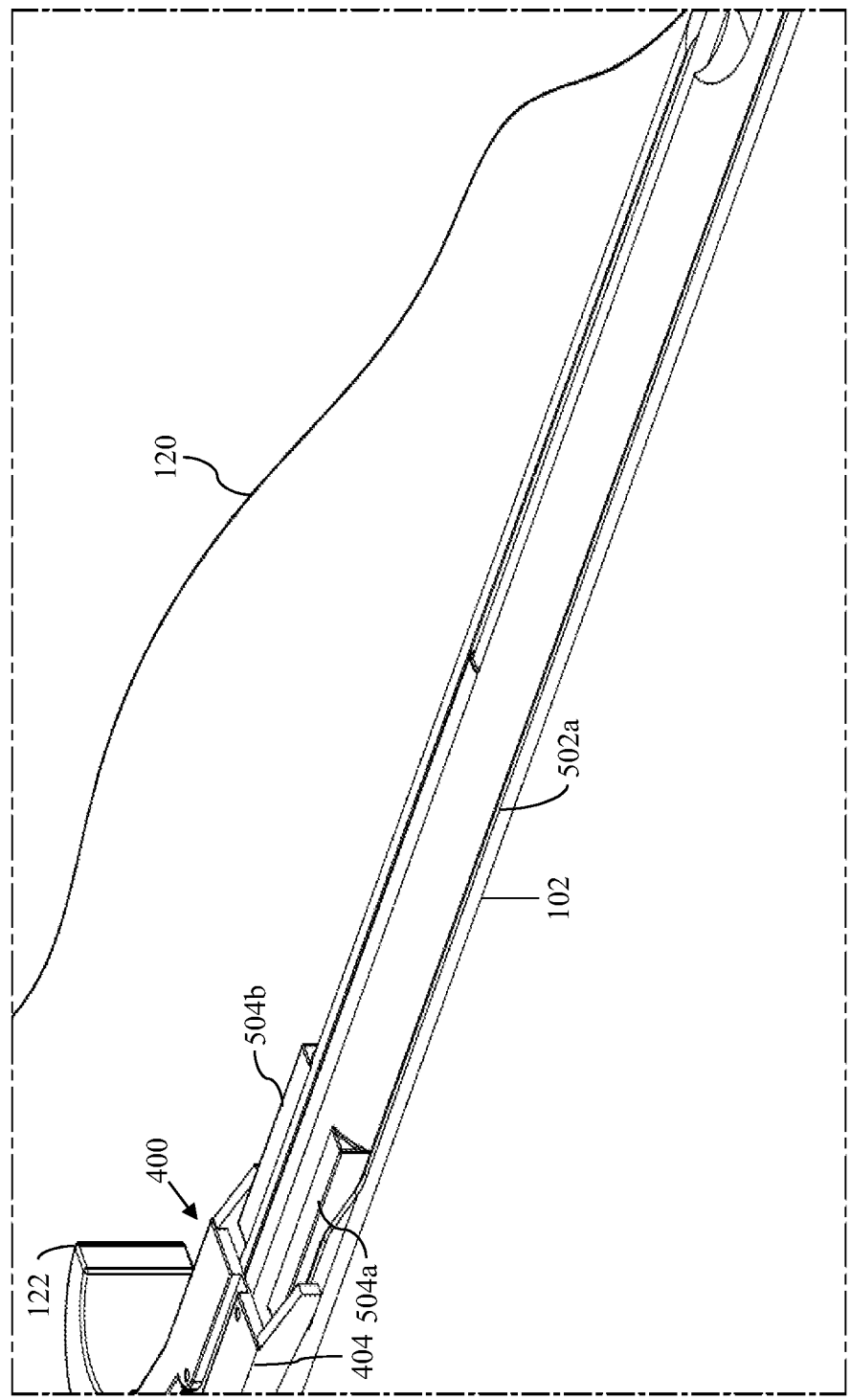
FIG. 5B illustrates an enlarged perspective view of the suturing device and the apparatus, in accordance with an exemplary embodiment of the present disclosure
Figure 5C:
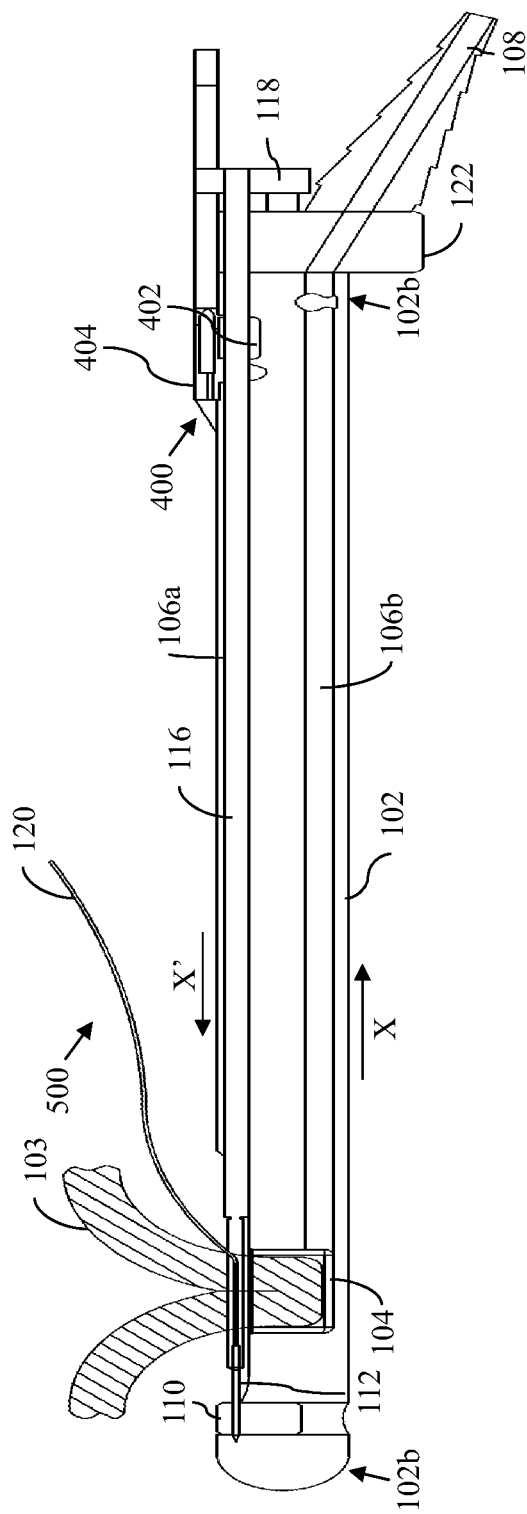
FIG. 5C illustrates a cross-sectional side view of the suturing device and the apparatus, in accordance with an exemplary embodiment of the present disclosure.
Figure 5D:
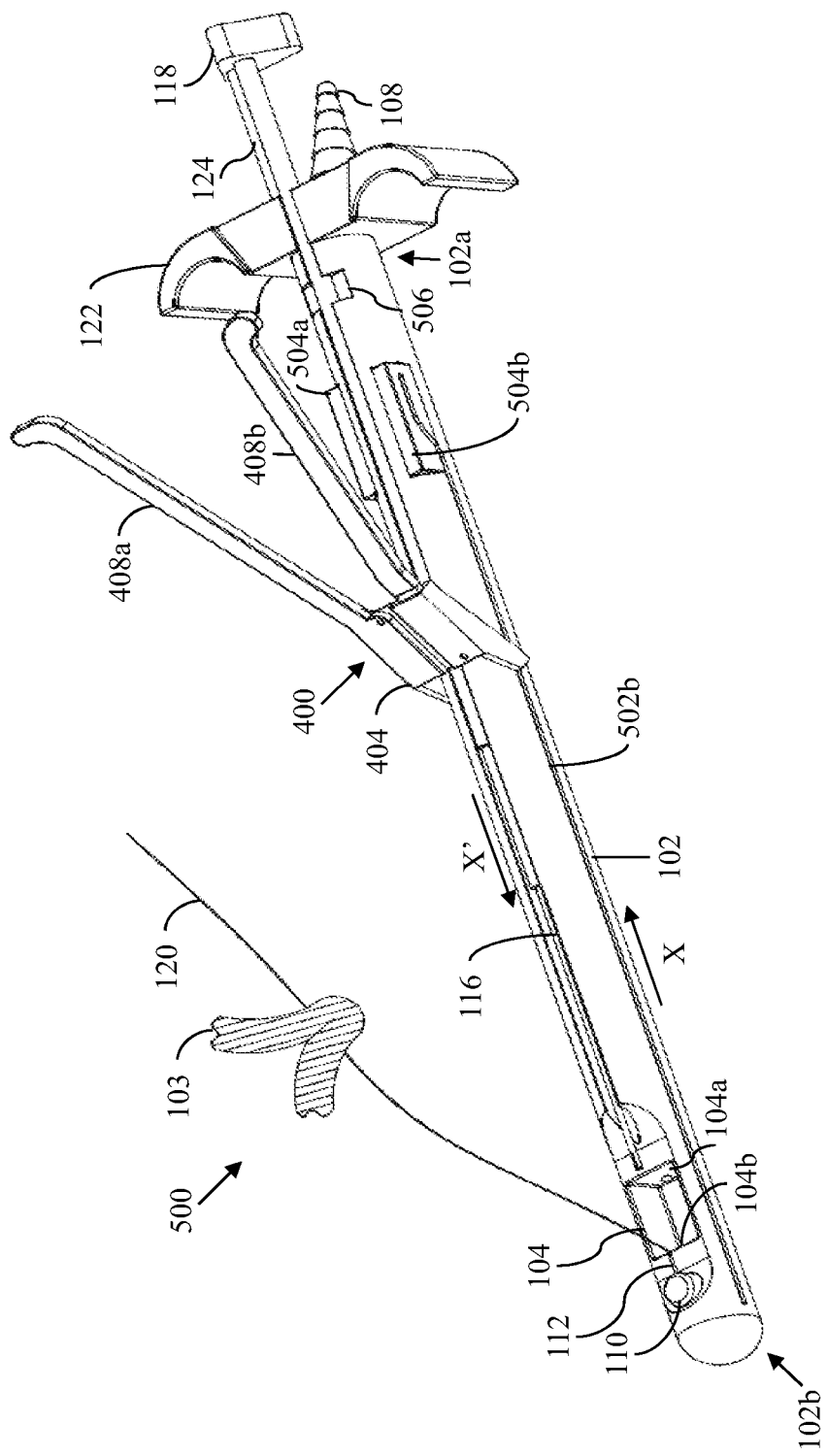
FIG. 5D illustrates a perspective view of the suturing device and the clamp when the apparatus is in a moving position, in accordance with an exemplary embodiment of the present disclosure.
Figure 5E:
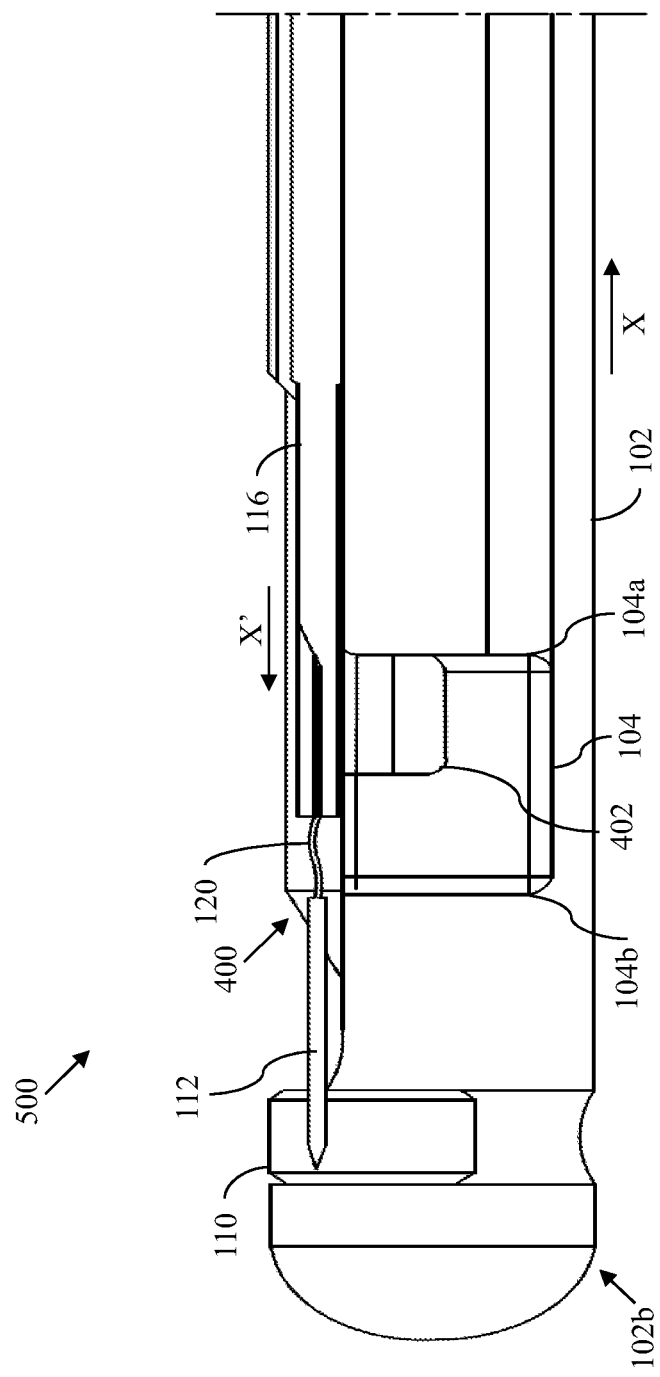
FIG. 5E illustrates an enlarged side sectional view of the apparatus positioned at a distal end of the suturing device, in accordance with an exemplary embodiment of the present disclosure.

FIGS. 5A-5C illustrate a first perspective view, a second perspective view, and a cross-sectional side view, respectively, of the suturing device 500 with the apparatus 400 mounted thereto, in accordance with an exemplary embodiment of the present disclosure. As shown in FIGS. 5A and 5B, the apparatus 400 is in a resting position. The suturing device 500 is functionally and structurally similar to the suturing device 100 of the previous embodiments. Unlike the suturing device 100, however, the suturing device 500 includes a first groove 502a and a second groove 502b both of which extend longitudinally along a peripheral surface of the elongated member 102. The first groove 502a and the second groove 502b are preferably positioned parallel and diametrically opposite to each other. The suturing device 500 further includes first and second protuberances 504a and 504b that are positioned in proximity to the proximal end 102a of the elongated member 102, and a bore 506 (as shown in FIG. 5D) that is formed in the elongated member 102 in proximity to the first and second protuberances 504a and 504b. The first and second grooves 502a and 502b also extend longitudinally over the first and second protuberances 504a and 504b, respectively. The first and second protuberances 504a and 504b are dimensioned to allow the clamp 404 to securely rest on the elongated member 102 at the proximal end 102a of the suturing device 500 as shown in FIG. 5A when the clamp 404 is not in use (i.e., when the clamp 404 is in the resting position). While in the resting position, the base 402 of the apparatus 400 sits within the bore 506 to further help secure the apparatus 400 in position. As shown in FIG. 5A, the first and second guide pins 406a and 406b (shown in FIG. 4B) of the clamp 404 extend inwardly into the first groove 502a and the second groove 502b, respectively, such that the clamp 404 may slide along the length of the elongated member 102 while the first and second guide pins 406a and 406b track respective ones of the first groove and the second groove 502a and 502b.

Operation of the apparatus 400 will now be explained in greater detail in conjunction with FIGS. 5D-5H.

As shown in FIG. 5D, the needle 112 and suture 120 have been passed through the tissue 103 and the operating handle 118 has been retracted from the fully advanced position to the fully retracted position, thereby retracting the needle pusher 116 such that it disengages from the needle 112 while the needle 112 remains captured by the needle capturing assembly 110 and also thereby retracting the blocking member 124 such that it no longer blocks the first aperture 126 (not shown). As a result, the vacuum is no longer applied to the cavity 104 and the suctioned tissue 103 is released from the cavity 104 while the suture 120 remains passed through the tissue 103. At this point, the suturing device 500 is removed from the body and the apparatus 400 is lifted from its resting position and slid along towards the distal end 102b of the suturing device 500 in the direction X' until the base 402 is aligned above the cavity, upon which the apparatus 400 is lowered such that the base 402 is positioned within the cavity. It should be appreciated that, in the fully retracted position, the needle pusher 116 is sufficiently retracted so as to prevent the needle pusher 116 from interfering with the coupling between the apparatus 400 and the cavity 104 when the base 402 of the apparatus 400 is inserted into the cavity 104. Further, because the entirety of the needle 112 has passed across the second wall 104b of the cavity 104, the needle 112 does not interfere with the coupling between the apparatus 400 and the cavity 104 when the base 402 of the apparatus 400 is inserted into the cavity 104. As described below, when the apparatus 400 is in this position, the apparatus 400 may be operated to release the needle 112 from the needle capturing assembly 110 and repositioned the needle 112 so as to be reengaged by the needle pusher 116 to perform one or more successive suturing operations as described above.

Figure 5F:
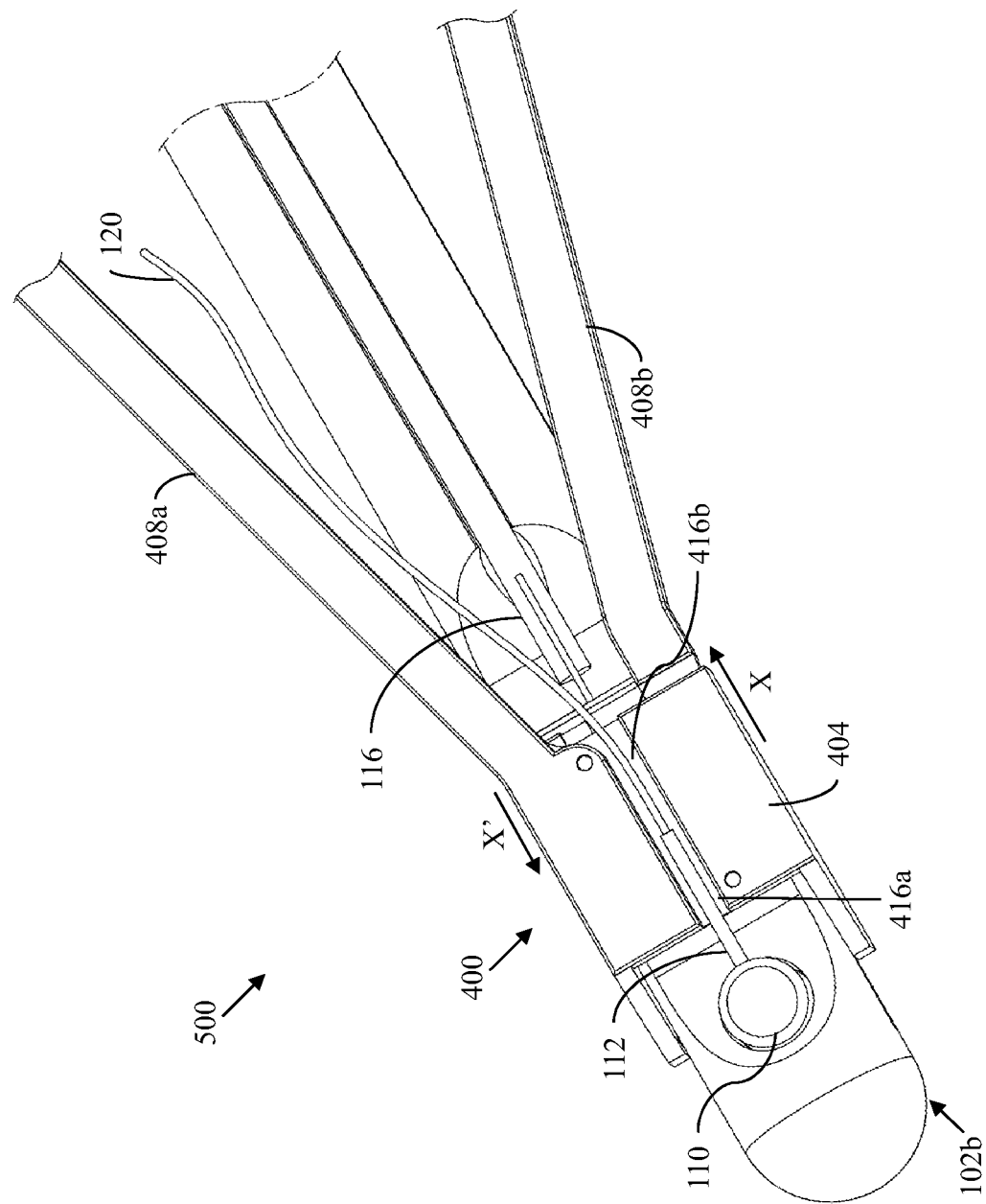
FIGS. 5F and 5G illustrate an enlarged perspective view and a side sectional view, respectively, of the apparatus positioned at the distal end of the suturing device when an operating handle is at a partially advanced position, in accordance with an exemplary embodiment of the present disclosure.
Figure 5G:
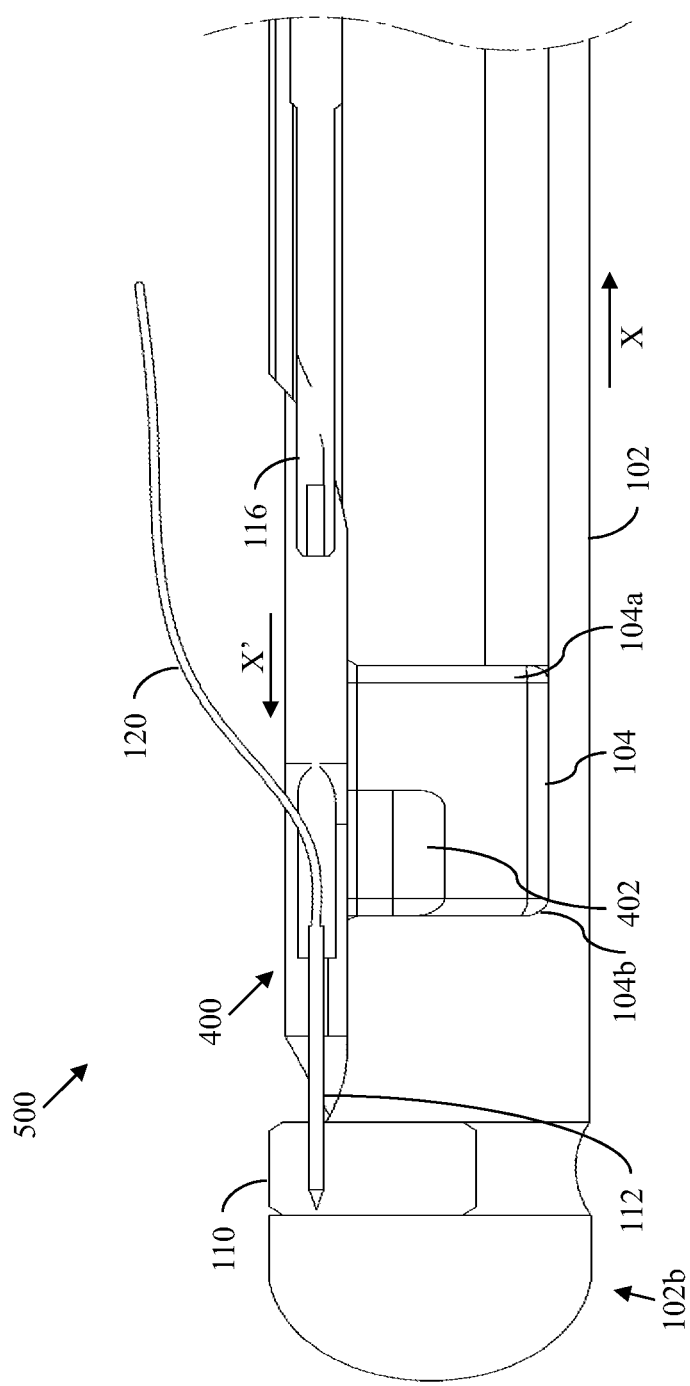
Figure 5H:
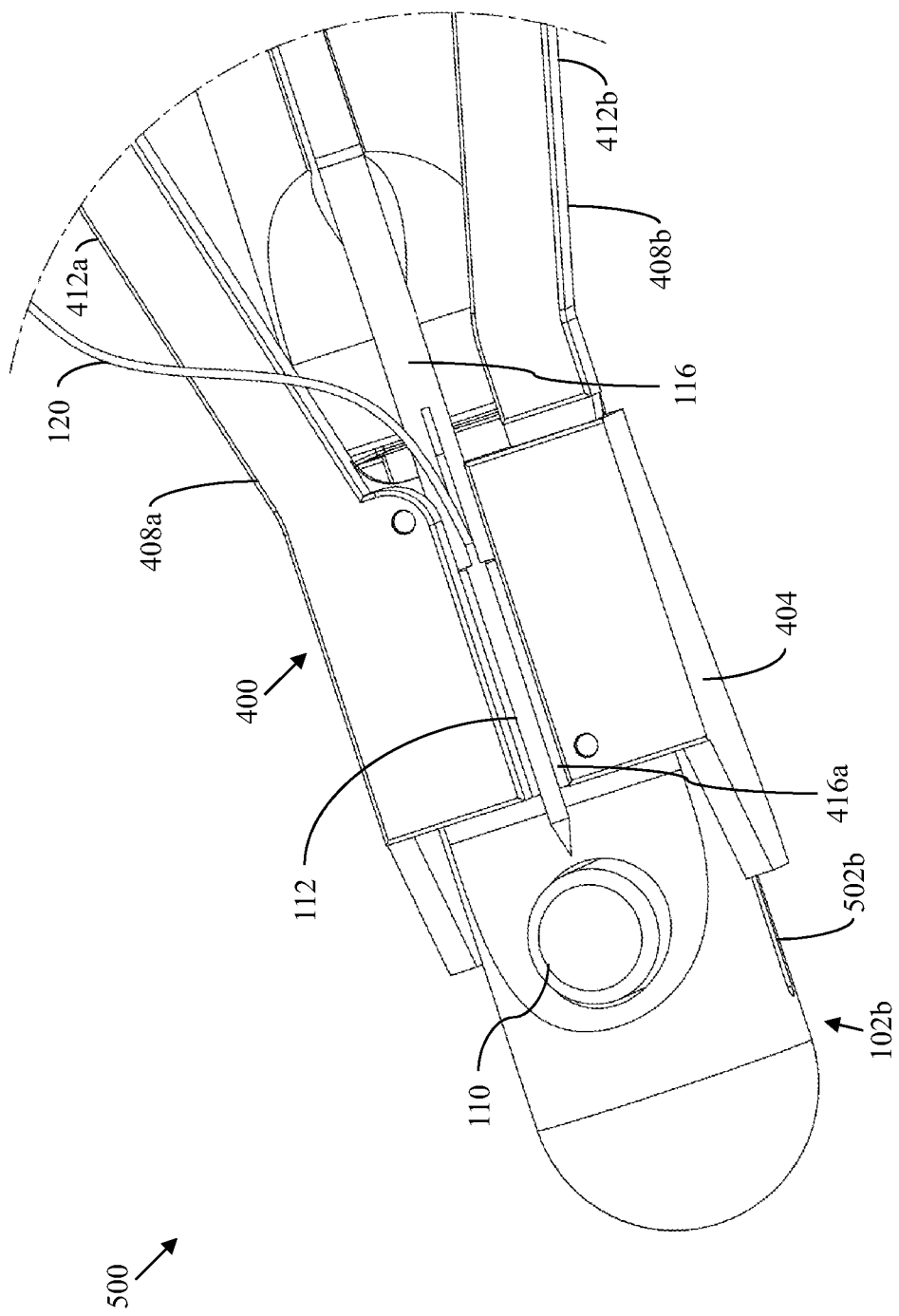
FIGS. 5H and 5I illustrate an enlarged perspective view and a side sectional view, respectively, of the apparatus positioned at the distal end of the suturing device when an operating handle is at a partially advanced position, in accordance with an exemplary embodiment of the present disclosure.
Figure 5I:
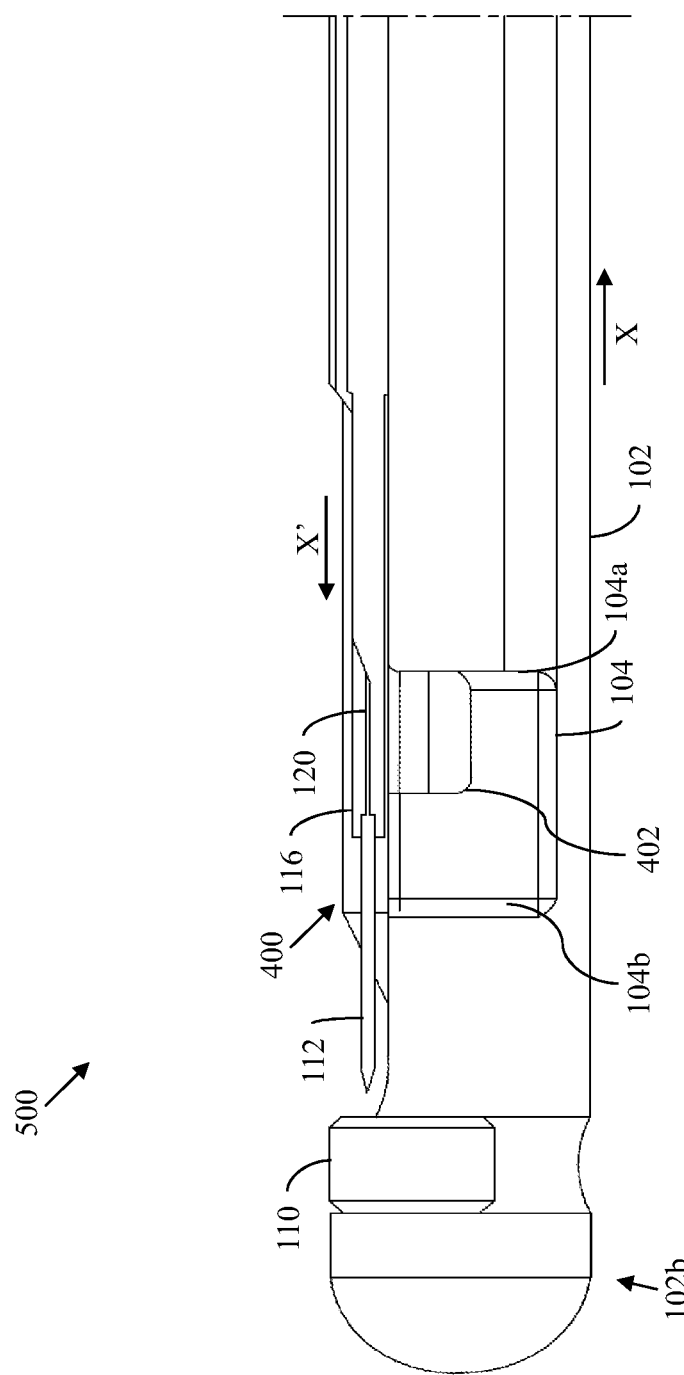

As shown in FIG. 5E, when the base 402 of the apparatus 400 is initially positioned within the cavity 104, the base 402 is against the first wall 104a of the cavity 104. Thereafter, the apparatus 400 is further moved in the direction X' towards the distal end 102b of the suturing device 500 until the base 402 is against the second wall 104b of the cavity 104. In this position, the end of the needle 112 extending from the needle capturing assembly 110 is received by in the first channel 416a of the first lever 408a as shown in FIGS. 5F and 5G. Once the needle 112 is positioned within the first channel 416a, the user of the suturing device 500 may squeeze the first handle 412a and the second handle 412b to clamp the needle 112 as shown in FIG. 5H. Once the needle 112 is clamped with a sufficient clamping force, the user of the suturing device 500 may slide the apparatus 400 in the direction X towards the proximal end 102a of the suturing device 500 until the base 402 of the apparatus 400 meets the first wall 104a of the cavity 104, for example, by pulling on the first and second handles 412a and 412b, thereby extracting the needle 112 from the needle capturing assembly 110 as shown in FIGS. 5H and 5I Once the needle 112 has been extracted from the needle capturing assembly 110, the operating handle 118 may be progressively advanced from the fully retracted position towards the fixed handle 122 in the direction X', thereby advancing the needle pusher 116 until the needle pusher 116 is positioned with the second channel 416b and re-engages with the end of the needle 112. Preferably, the needle pusher 116 is advanced until the second detent 132b of the needle pusher 116 engages with the ball 138b of the ball-spring detent mechanism 130 to create the audible and/or tactile feedback described above, such that the user is made aware that the needle pusher 116 has re-engaged the end of the needle 112. Following re-engagement of the needle 112 with the needle pusher 116, the operating handle 118 may be retracted towards the fully retracted position such that the needle 112 is returned to the position shown in FIG. 1A. Once the needle 112 is in the position shown in FIG. 1A, the user of the suturing device 500 may slide the apparatus 400 back to the resting position, reposition the suturing device 500 within the subject's body via the same incision or another incision, and re-pass the needle 112 and the suture 120 through the tissue 103 previously sutured or pass the needle 112 and the suture 120 through another tissue. It should be appreciated that by repeating the foregoing procedure, the suturing device 500 may be operated to make multiple passes of the needle 112 and the suture 120 through tissue 103 (or another tissue) and thereby make multiple stitches without having to replace the needle 112 or the suture 120.

Figure 6A:
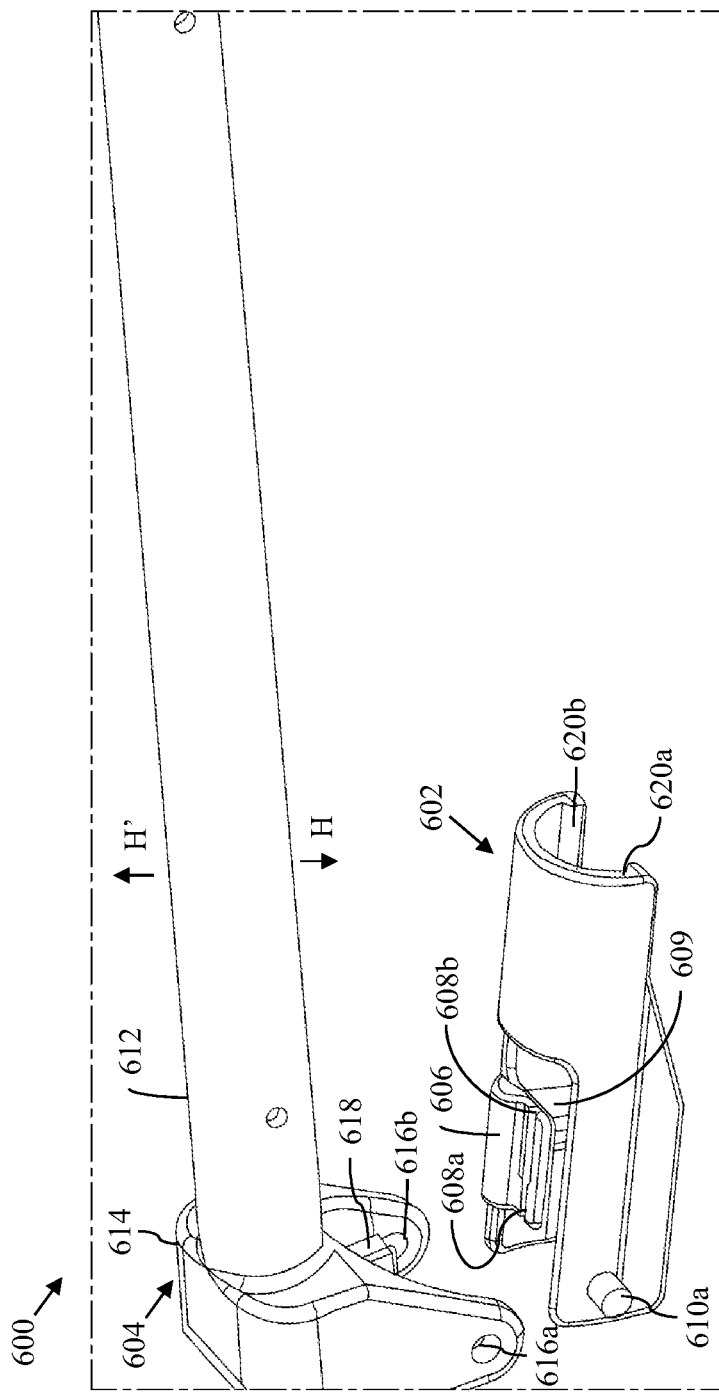
FIG. 6A illustrates an exploded view of an apparatus for use with a suturing device, in accordance with an exemplary embodiment of the present disclosure.

FIG. 6A illustrates perspective view of an apparatus 600 for use with a suturing device 700 (shown in FIG. 7A), in accordance with an exemplary embodiment of the present disclosure. It should be appreciated that the suturing device 700 is structurally and functionally similar to the suturing device 100 of FIG. 1A, only modified to accommodate the apparatus 600 as described below. The apparatus 600 may be used to release the needle 112 from the needle capturing assembly 110 of the suturing device 700 and reposition the needle 112 so as to be reengaged by the needle pusher 116 of the suturing device 700.

As shown in FIG. 6A in accordance with an exemplary embodiment of the present disclosure, the apparatus 600 includes a sliding member 602 and a support handle 604. The sliding member 602 is dimensioned to fit over the elongated member 102 of the suturing device 700. For example, the sliding member 602 is shown in FIG. 6A as an arc-shaped or semi-circular structure. In a non-limiting example, the sliding member 602 may be suitably configured to fit (as shown in FIGS. 7A-7E) over the elongated member 102 in a "press-fit" or "snap-fit" fashion. The sliding member 602 further includes a clamping platform 606 that includes, therein, a channel 608a and a channel 608b (as shown in FIG. 7B). The channel 608b is preferably wider than the channel 608a and is preferably aligned and overlapped with the channel 608a. The channel 608a is sized and positioned to receive the needle 112. The channel 608b is sized and positioned to receive the needle pusher 116. The clamping platform 606 is attached to a base 609. The base 609 is preferably dimensioned to fit within the cavity 104 of the suturing device 700 to allow sufficient room for the base 609 to slide from one end of the cavity 104 to the other end of the cavity 104 as shown in FIGS. 7C, 7D, and 7E. The sliding member 602 further includes a first pivot pin 610a (see FIG. 6A) and a second pivot pin 610b (not shown, but on the opposite side of the sliding member 602) that protrude from a peripheral surface of the sliding member 602.

Figure 6B:
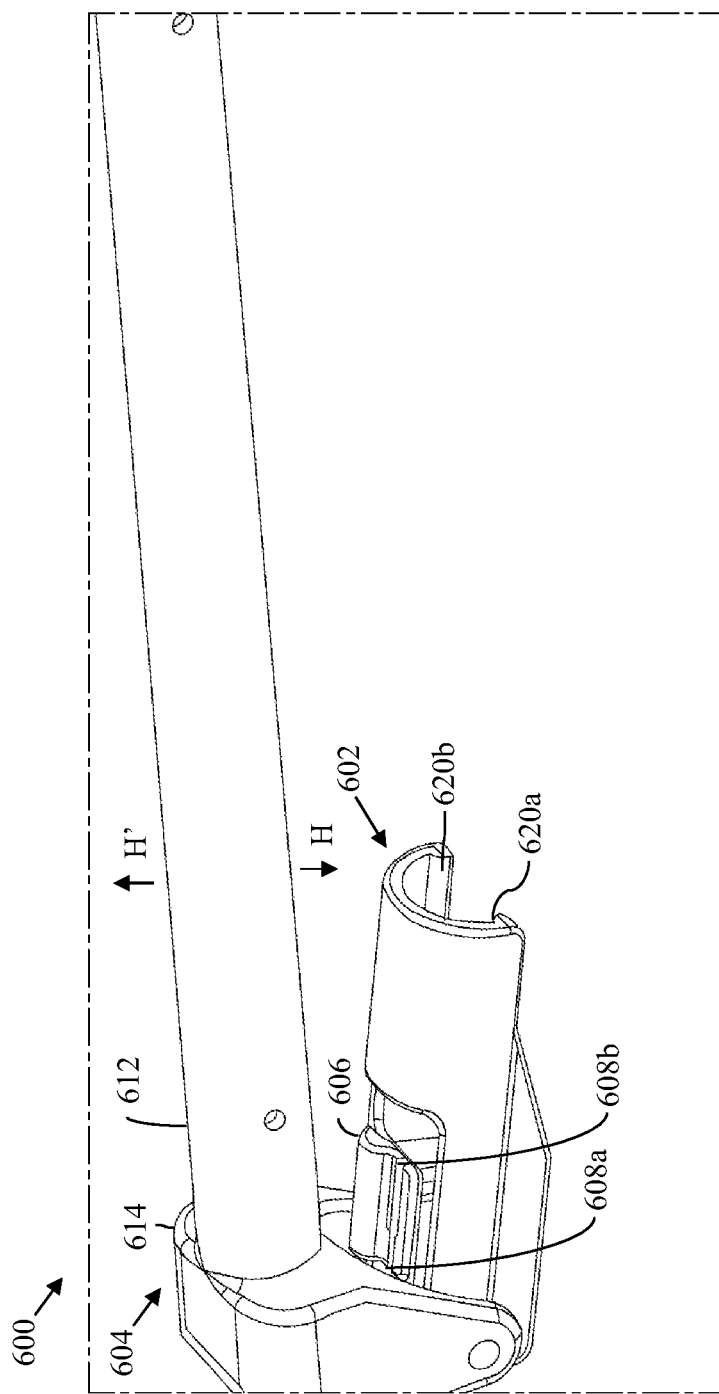
FIG. 6B illustrates a perspective view of the apparatus, in accordance with an exemplary embodiment of the present disclosure.

The support handle 604 includes a handle bar 612 and a coupling member 614 that is attached to the handle bar 612. The coupling member 614 includes first and second pivot holes 616a and 616b. The first and second pivot holes 616a and 616b are suitably configured to engage with the first and second pivot pins 610a and 610b, for coupling the support handle 604 to the sliding member 602 as shown in FIG. 6B. The support handle 604 can be rotated about the first and second pivot pins 610. In other words, the coupling between the support handle 604 and the sliding member 602 enables rotation of the support handle 604 along directions H and H' relative to the sliding member 602.

The coupling member 614 further includes a first protruding member 618 that is configured to clamp the needle 112 to the clamping platform 606 when the user rotates the support handle 604 along the direction H, while attempting to reposition the needle 112 in the channel 608a of the clamping platform 606. The clamping platform 606 is designed to engage with the first protruding member 618 in order to clamp the needle 112 for removing the needle 112 from the needle capturing assembly 110. The sliding member 602 further includes a first rail 620a and a second rail 620b that are positioned parallel and opposite to each other. The first and second rails 620a and 620b are protruded internally from bottom edges of the sliding member 602. In one embodiment, the apparatus 600 and its various parts may be made of a material or materials designed to ensure proper functioning of the apparatus 600 and clamping of the needle 112. Such materials may include polymers, composites, metals or the like.

Figure 7A:
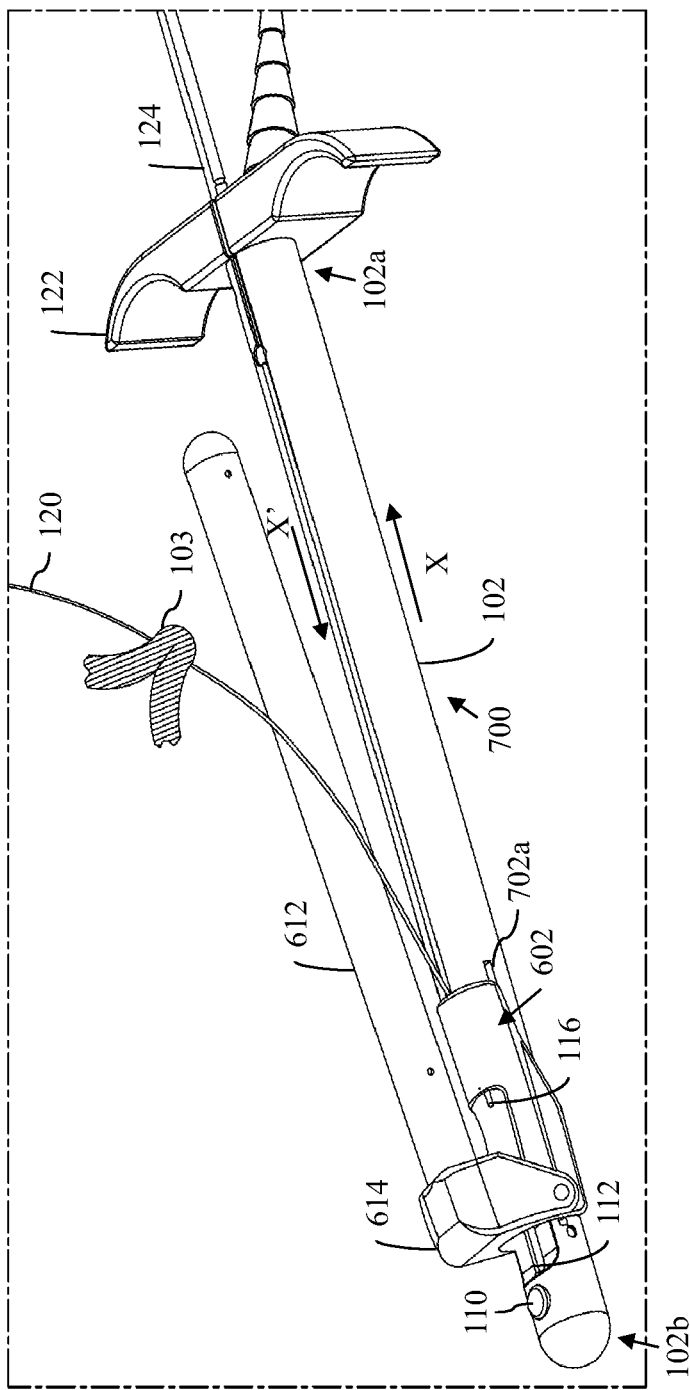
FIG. 7A illustrates a perspective view of the suturing device and the apparatus, in accordance with an exemplary embodiment of the present disclosure.
Figure 7B:
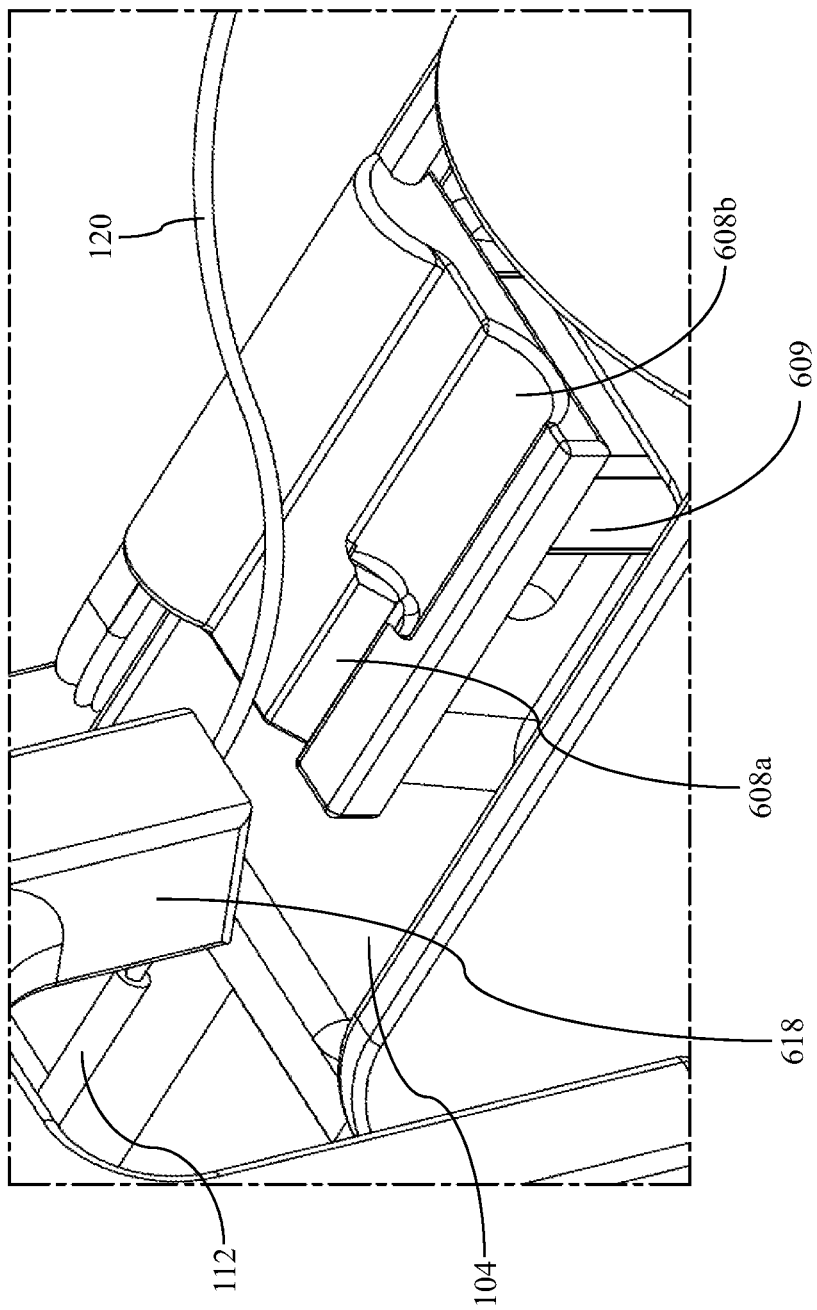
FIG. 7B illustrates an enlarged top view of the apparatus and the suturing device, in accordance with an exemplary embodiment of the present disclosure.
Figure 7C:
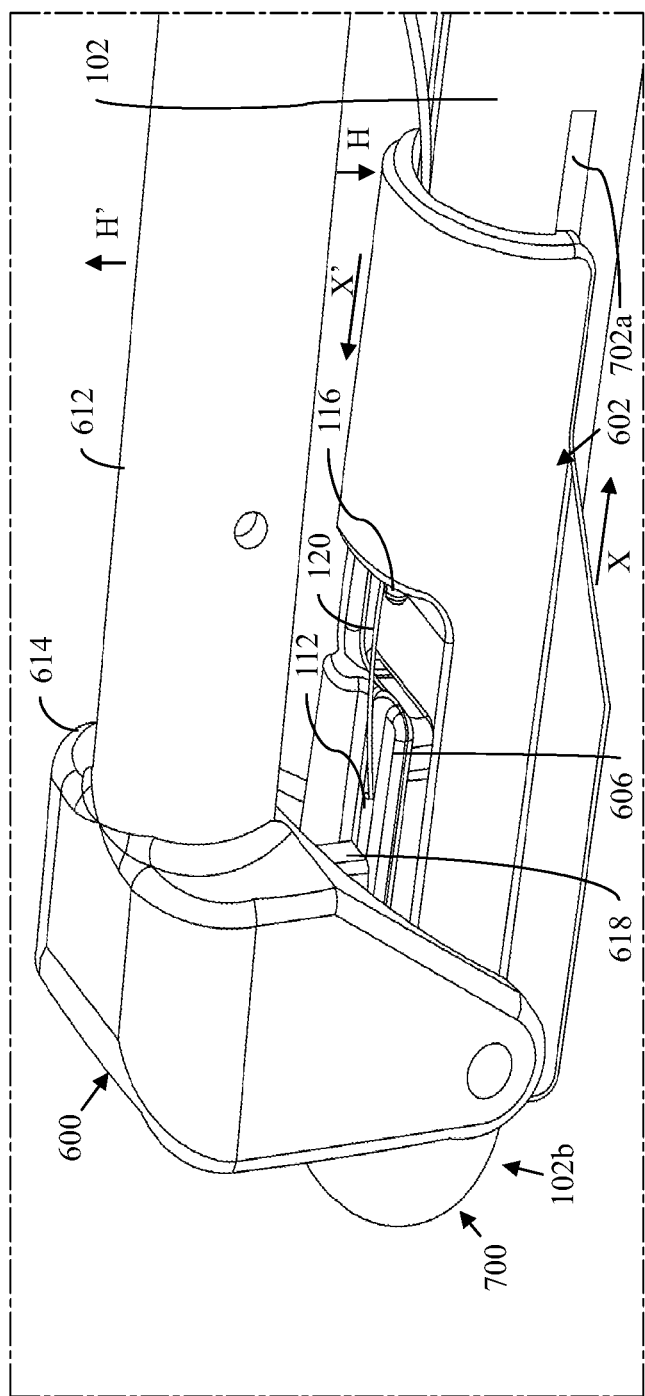
FIG. 7C illustrates an enlarged view of the apparatus at a distal end of the suturing device when the apparatus is moved towards the distal end, in accordance with an exemplary embodiment of the present disclosure.
Figure 7D:
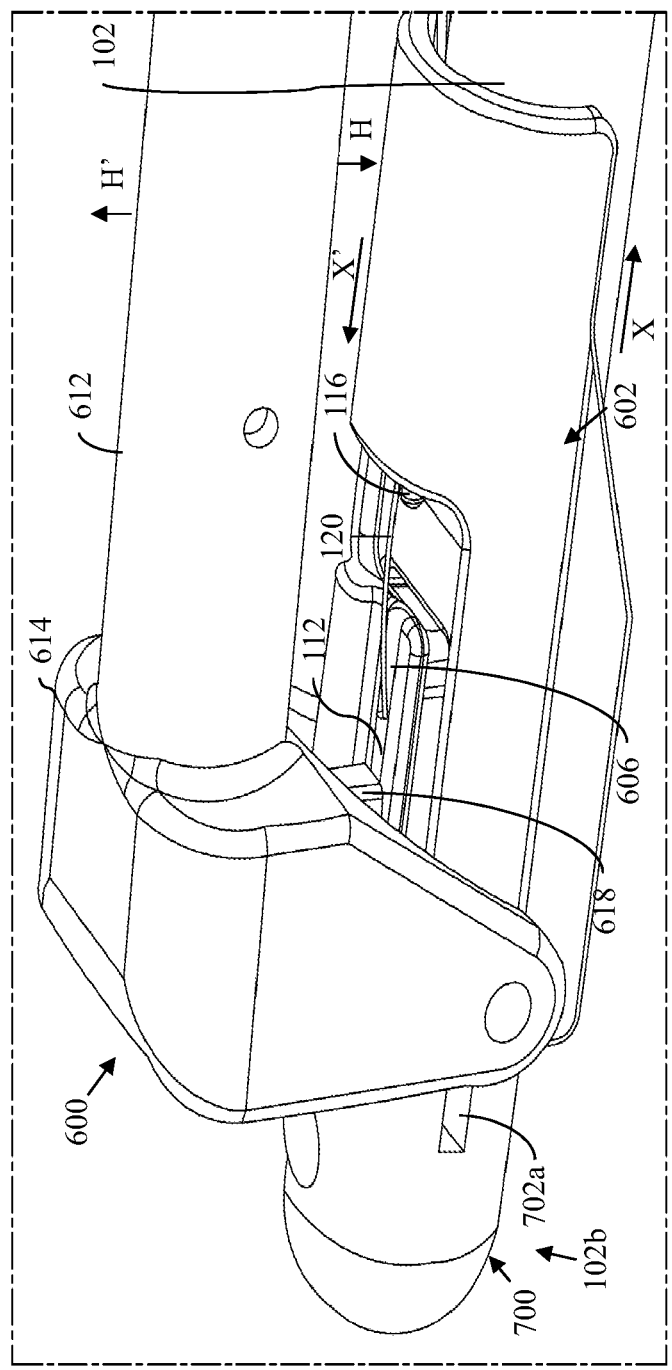
FIG. 7D illustrates an enlarged view of the apparatus at the distal end of the suturing device when the apparatus is moved away from the distal end, in accordance with an exemplary embodiment of the present disclosure.
Figure 7E:
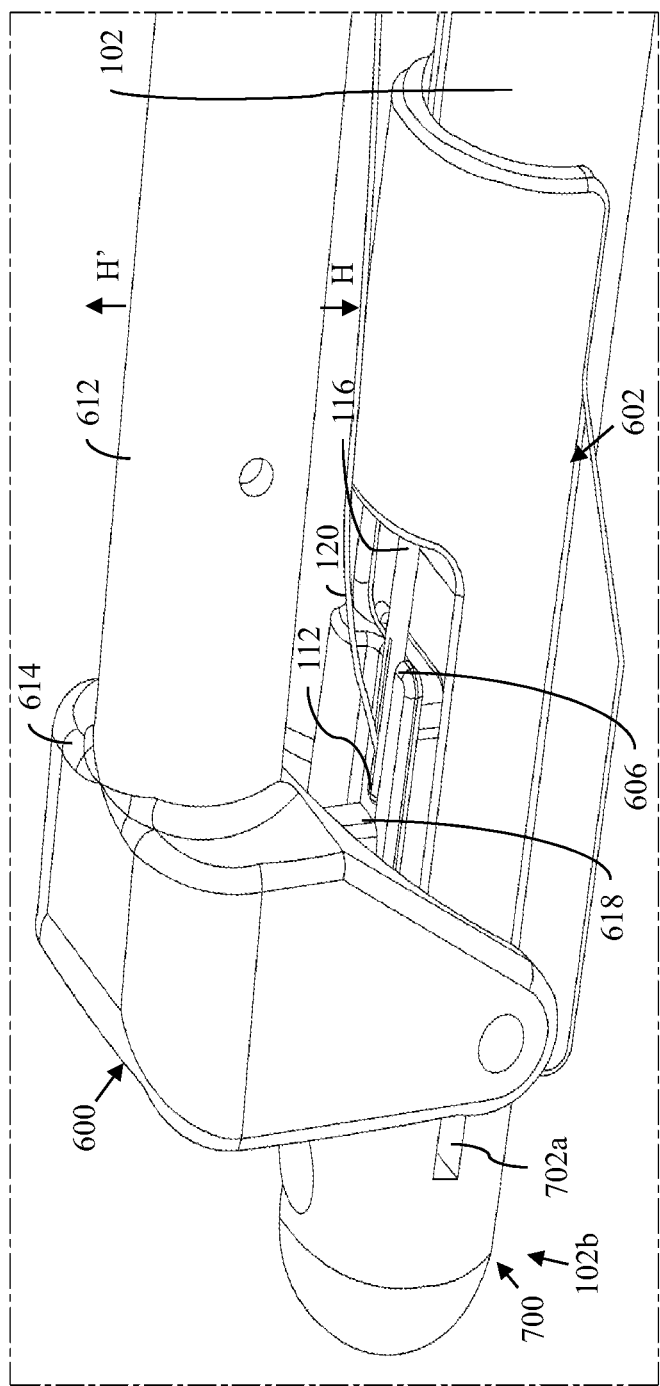
FIG. 7E illustrates an enlarged view of the apparatus and the suturing device when an operating handle is at a partially advanced position, in accordance with an exemplary embodiment of the present disclosure.

FIG. 7A illustrates a perspective view of the suturing device 700 and the apparatus 600, in accordance with an exemplary embodiment of the present disclosure. As shown in FIG. 7A, the suturing device 700 is structurally and functionally similar to the suturing device 100 of the previous embodiments. Unlike the suturing device 100, however, the suturing device 700 includes a first sliding track 702a and a second sliding track 702b (not shown) opposite the first sliding track 702a formed in the elongated member 102. As shown in FIG. 7A, the suturing device 700 has been removed from the body, the needle 112 has been captured by the needle capturing assembly 110 following the suturing of the suctioned tissue 103, the operating handle 118 has been retracted from the fully advanced position to the fully retracted position, thereby retracting the needle pusher 116 and disengaging the needle pusher 116 from the needle 112 while the needle 112 remains captured by the needle capturing assembly 110. It should be appreciated that the needle pusher 116 is sufficiently retracted so as to prevent the needle pusher 116 from interfering with the coupling between the apparatus 600 and the cavity 104 when the sliding member 602 is fitted to the suturing device 700. The first and second rails 620a and 620b of the sliding member 602 engage slidably with the first sliding track 702a and the second sliding track 702b, respectively of the suturing device 700. Further, it is assumed that the entirety of the needle 112 has passed across the second wall 104b of the cavity 104, thereby preventing the needle 112 from interfering with the fitment of the sliding member 602 to the suturing device 700.

The sliding member 602 is suitably configured to slide, in directions X and X', along the first sliding track 702a and the second sliding track 702b. The first sliding track 702a and the second sliding track 702b, in conjunction with the base 609, define a range of positions that the sliding member 602 can occupy, relative to the suturing device 700. For example, the length of the first sliding track 702a and the second sliding track 702b allows the sliding member 602 to be slid from a first position to a second position and vice-versa with respect to the elongated member 102. When the sliding member 602 is in the first position, the clamping platform 606 is positioned to receive the first end of the needle 112 extending from the needle capturing assembly 110. The user may clamp the needle 112 to the clamping platform 606 using the first protruding member 618 (as described earlier). While the needle 112 is clamped to the clamping platform 606 with sufficient clamping force, the sliding member 602 may be moved from the first position to the second position to disengage the needle 112 from the needle capturing assembly 110.

FIG. 7C illustrates an enlarged view of the suturing device 700 and the apparatus 600, in accordance with an exemplary embodiment of the present disclosure. The sliding member 602 is slid to the first position of the suturing device 700. The needle 112 is captured by the needle capturing assembly 110 and the operating handle 118 is in the fully retracted position such that the needle 112 is disengaged from the needle pusher 116. In order to extract the needle 112 from the needle capturing assembly 110 and reposition the needle 112 such that it is re-engaged by the needle pusher 116, a user of the suturing device 700 may, using the handle bar 612, move the support handle 604 downwards (i.e., along direction H) towards the clamping platform 606. As the support handle 604 is moved in this manner, the first end of the needle 112 extending from the needle capturing assembly 110 is clamped in the channel 608a in the clamping platform 606. Once the needle 112 is positioned within the channel 608a in the clamping platform 606, the user of the suturing device 700 may squeeze the handle bar 612 to hold the needle 112 within the channel 608a in the clamping platform 606. Once the needle 112 is clamped with a sufficient clamping force, the user of the suturing device 700 may slide the apparatus 600 towards the fixed handle 122, for example, by pulling the apparatus along the direction X, until the needle 112 is extracted from the needle capturing assembly 110. FIG. 7D illustrates an enlarged view of the apparatus 600 at the distal end 102b of the suturing device 700 when the apparatus 600 is retracted towards the fixed handle 122 (i.e., away from the distal end 102b) subsequent to the extraction of the needle 112 from the needle capturing assembly 110 as described above. In accordance with an exemplary embodiment of the present disclosure, once the needle 112 has been extracted from the needle capturing assembly 110, the operating handle 118 may be progressively advanced from the fully retracted position towards the fixed handle 122, thereby advancing the needle pusher 116 until the needle pusher 116 re-engages with the end of the needle 112. The needle pusher 116 is received in the channel 608b of the clamping platform 606.

FIG. 7E illustrates the needle 112 re-engaged with the needle pusher 116 following a completion of above procedure. Following the re-engagement of the needle 112 with the needle pusher 116, the apparatus 600 may be detached from the suturing device 700, for example, by pulling on the apparatus 600 such that it disengages from the first sliding track 702a and the second sliding track 702b, the operating handle 118 may be retracted towards the fully retracted position such that the needle 112 is in the position shown in FIG. 1A, and the suturing device 700 and the apparatus 600 may be operated as described above to administer one or more additional passes of the needle 112 and suture 120 through tissue 103 (or another tissue) and thereby make multiple stitches without having to replace the needle 112 or the suture 120.

Figure 8A:
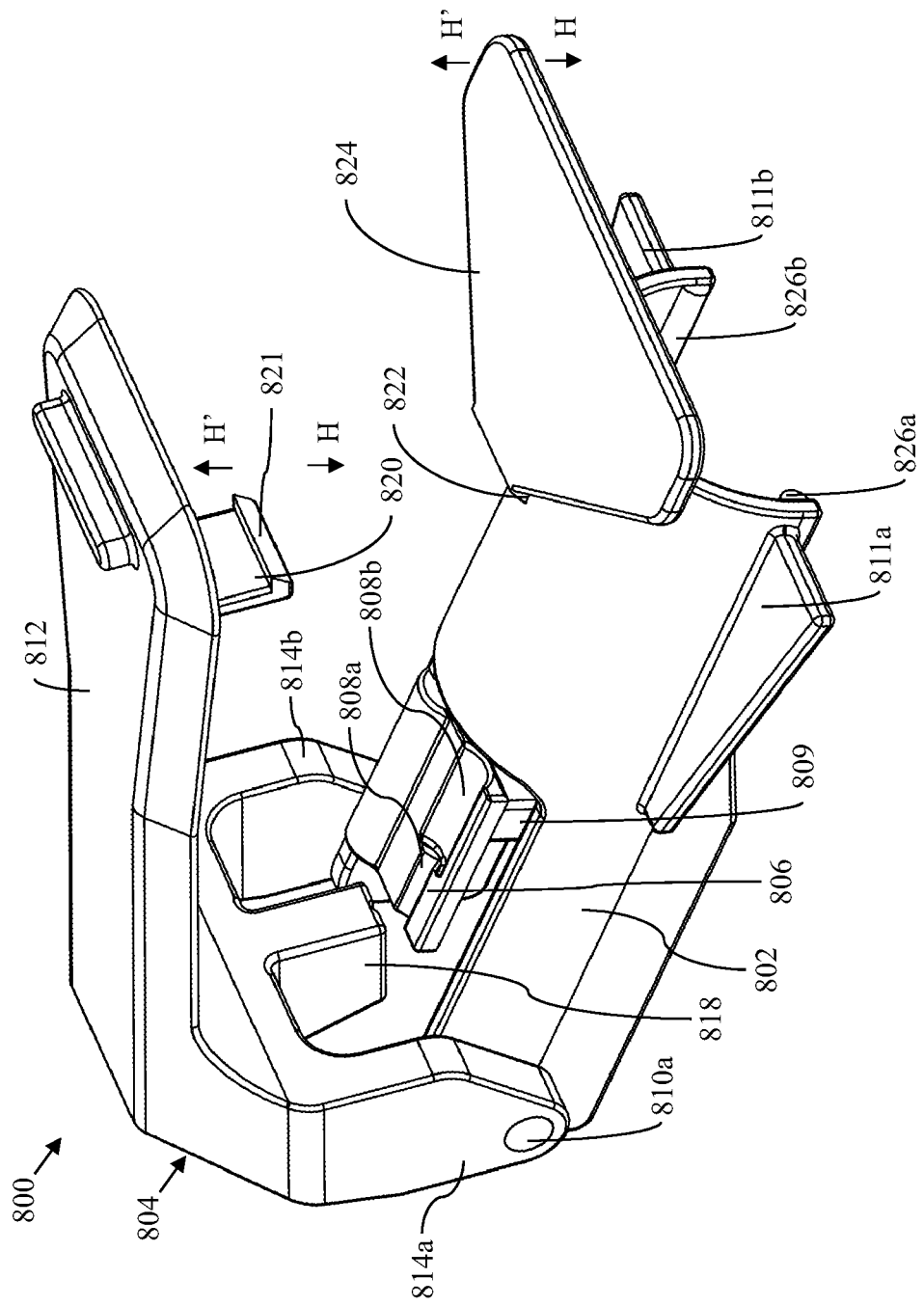
FIG. 8A illustrates a perspective view of an apparatus for use with a suturing device, in accordance with an exemplary embodiment of the present disclosure.
Figure 8B:
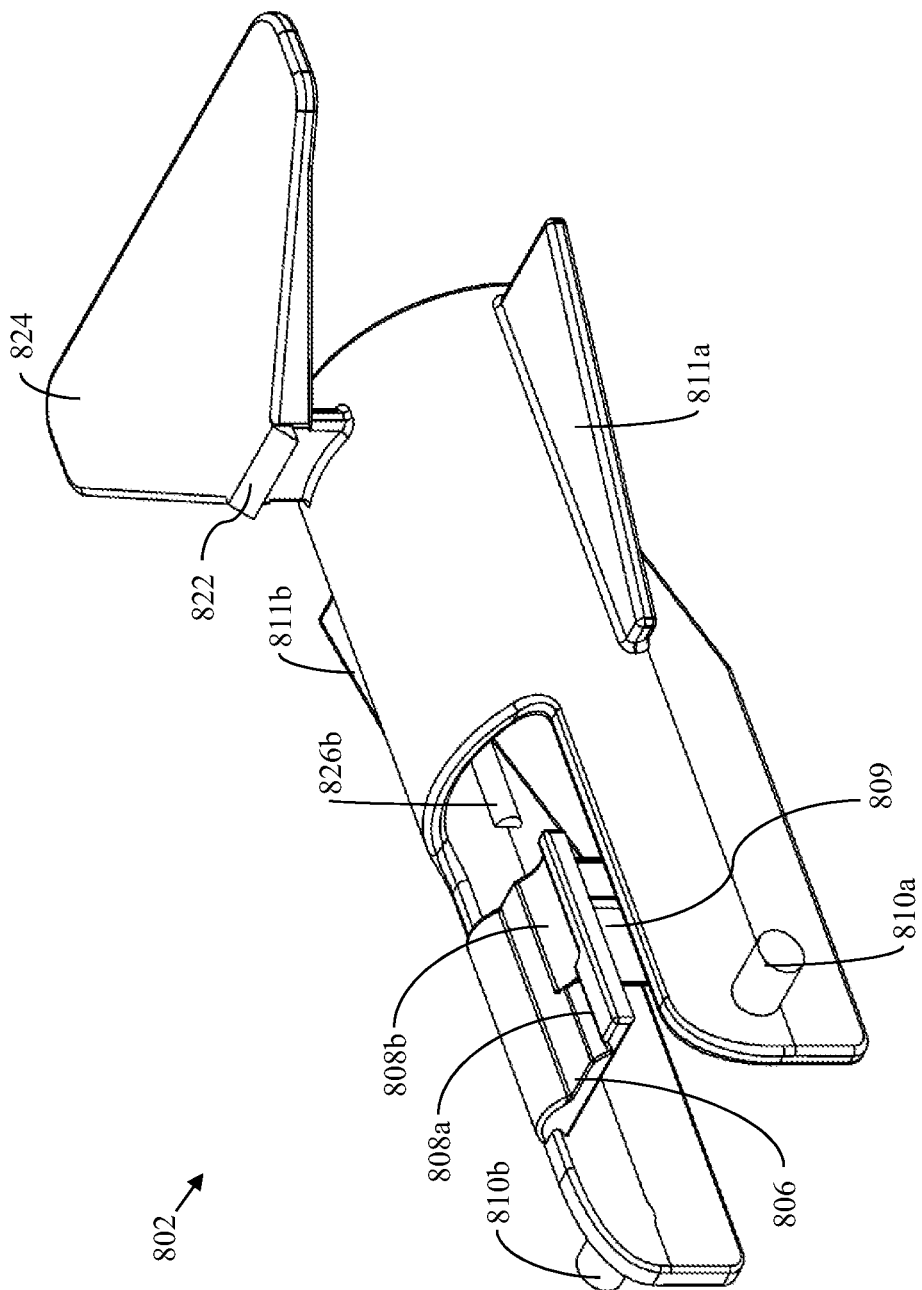
FIG. 8B illustrates a perspective view of a sliding member of the apparatus, in accordance with an exemplary embodiment of the present disclosure.
Figure 8C:
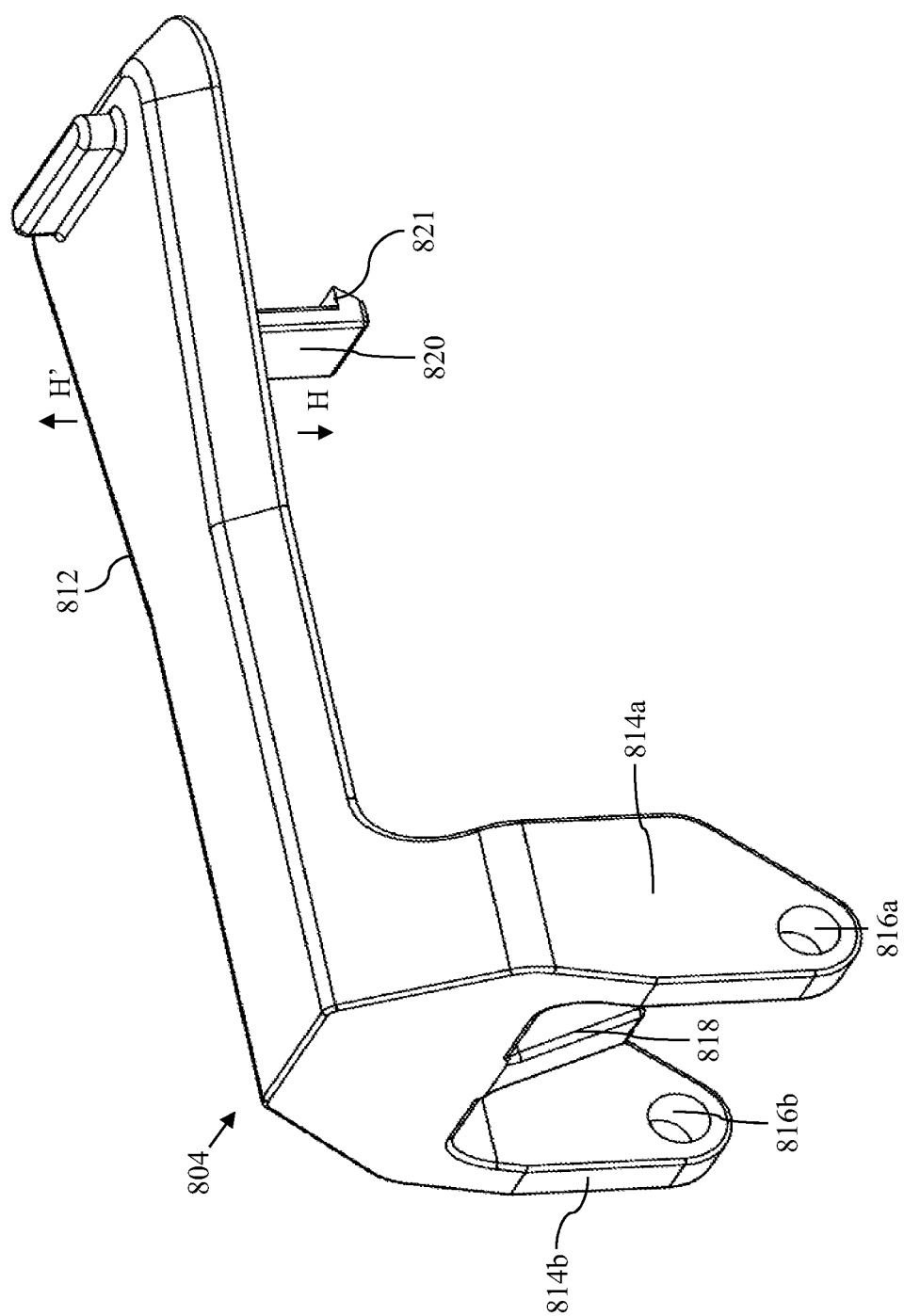
FIG. 8C illustrates a perspective view of a lever of the apparatus, in accordance with an exemplary embodiment of the present disclosure.

FIG. 8A-8C illustrate perspective and exploded views of an apparatus 800 for use with a suturing device 900 (shown in FIG. 9A), in accordance with an exemplary embodiment of the present disclosure. It should be appreciated that the suturing device 900 is structurally and functionally similar to the suturing device 100 of FIG. 1A, only modified to accommodate the apparatus 800 as described below. The apparatus 800 may be used to release the needle 112 from the needle capturing assembly 110 of the suturing device 100 and reposition the needle 112 so as to be reengaged by the needle pusher 116 of the suturing device 900.

As shown in FIG. 8A, the apparatus 800 includes a sliding member 802 and a lever 804, as shown in an accordance with an embodiment of the invention. The sliding member 802 is dimensioned to fit over the elongated member 102 of the suturing device 900. For example, the sliding member 802 is shown in FIG. 8A as an arc-shaped or semi-circular structure. In a non-limiting example, the sliding member 802 may be suitably configured to fit (as shown in FIGS. 9A-9J) over the elongated member 102 in a "press-fit" or "snap-fit" fashion. The sliding member 802 further includes, therein, a clamping platform 806 that includes, therein, a channel 808a and a channel 808b (shown in FIG. 8B). The channel 808b is preferably wider than the channel 808a and is preferably aligned and overlapped with the channel 808a. The channel 808a is sized and positioned to receive the needle 112. The channel 808b is sized and positioned to receive the needle pusher 116. The clamping platform 806 is attached to a base 809 that is dimensioned to fit into the cavity 104 of the suturing device 900. The base 809 is dimensioned such that sufficient room is allowed for the base 809 to slide from one end of the cavity 104 to the other end of the cavity 104 (i.e., from the first wall of the cavity to the second wall of the cavity), as shown in FIGS. 9B and 9F. The sliding member 802 further includes first and second pivot pins 810a and 810b (shown in FIG. 8B) that protrude from a peripheral surface of the sliding member 802. The sliding member 802 further includes first and second side support members 811a and 811b. The first and second side support members 811a and 811b are intended to provide ergonomic support to the user for moving the sliding member 802 over the elongated member 102 of the suturing device 900. For example, the user may choose to rest his thumb and index finger on the first and second side support members 811a and 811b, respectively, while moving the sliding member 802 over the elongated member 102. The lever 804 includes a handle bar 812 and first and second arms 814a and 814b that extend from the handle bar 812. As shown in FIG. 8C, the first and second arms 814a and 814b include first and second pivot holes 816a and 816b, respectively. The first and second pivot holes 816a and 816b are suitably configured to engage with the first and second pivot pins 810a and 810b, for coupling the lever 804 to the sliding member 802 as shown in FIG. 8A. The lever 804 can be rotated about the first and second pivot pins 810a and 810b. In other words, the coupling between the lever 804 and the sliding member 802 enables rotation of the lever 804 along the directions H and H', relative to the sliding member 802. In an embodiment, the lever 804 may be attached to the sliding member 802 through a living hinge. In this scenario, the apparatus 800 may be manufactured in entirety as a single unit with the use of a 3D printing machine.

Figure 8D:
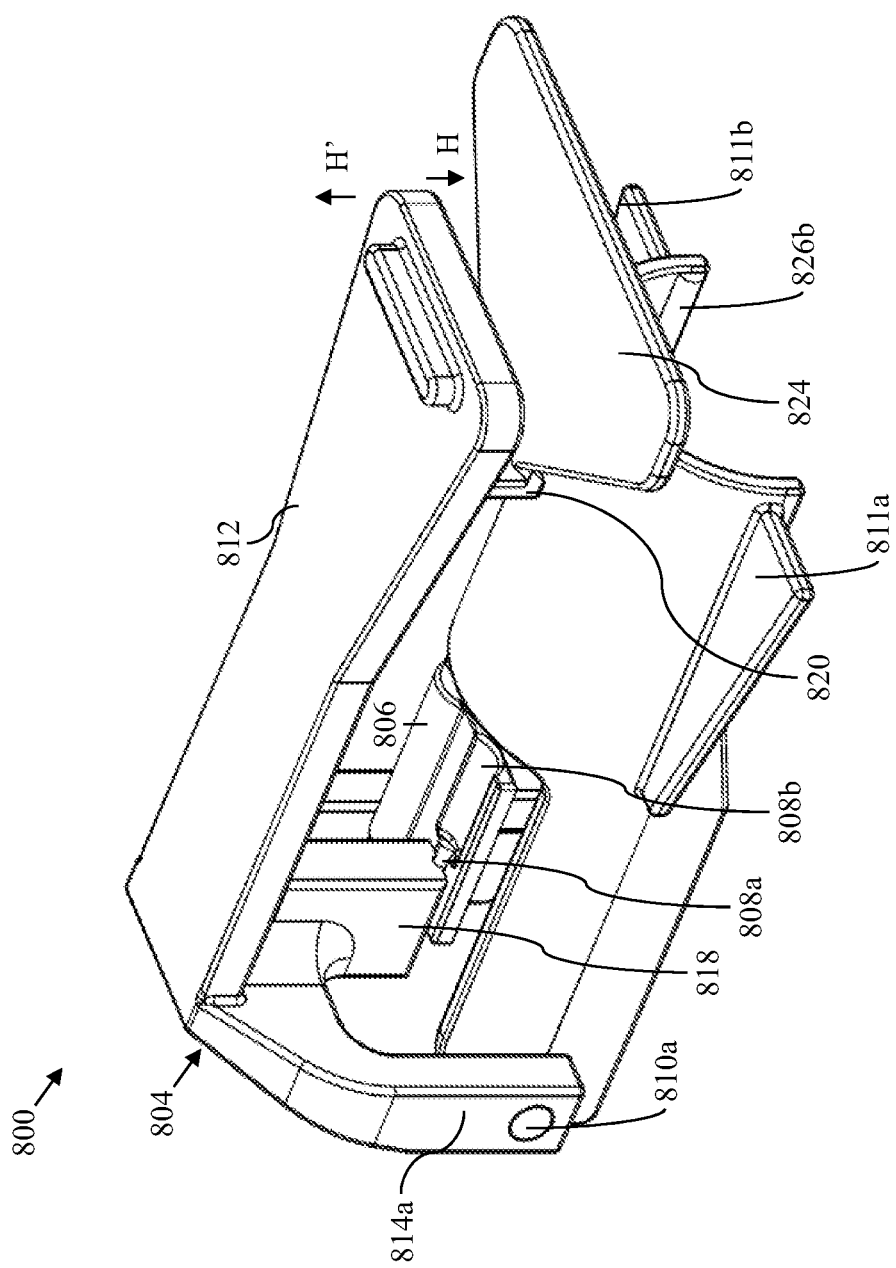
FIGS. 8D and 8E illustrate front and rear perspective views of the apparatus, in accordance with an exemplary embodiment of the present disclosure.

The lever 804 further includes a protruding member 818 that is configured to clamp the needle 112 to the clamping platform 806 when the user rotates the lever 804 along the direction H, while attempting to reposition the needle 112 in the channel 808a of the clamping platform 806. The clamping platform 806 is designed to engage with the protruding member 818 in order to clamp the needle 112 for removing the needle 112 from the needle capturing assembly 110. The lever 804 includes a snap ledge 820 that protrudes from a bottom surface thereof. The snap ledge 820 includes a mating surface 821 that is suitably configured to engage with a locking member 822. The locking member 822 protrudes outwardly from a top support member 824 that is included in the sliding member 802. The mating surface 821 of the snap ledge 820 and the locking member 822 are suitably dimensioned to enable the mating surface 821 to interlock with the locking member 822 in a snap-fit or press-fit fashion. The snap ledge 820 may be interlocked with the locking member 822 (as shown in FIG. 8D) when the user applies sufficient force on the handle bar 812 along the direction H. When the snap ledge 820 is locked to or interlock with the locking member 822, the protruding member 818 clamps the needle 112 to the clamping platform 806, and the needle 112 remains clamped to the clamping platform 806 until the user disengages the snap ledge 820 from the locking member 822. In other words, the needle 112 remains clamped to the clamping platform 806 until the user releases the snap ledge 820 from the locking member 822. This allows user to effortlessly use the apparatus 800 for easy retraction and re-engagement of the needle 112.

The user may release the snap ledge 820 from the locking member 822 by applying sufficient force on the top support member 824 along the direction H. The user is required to apply the force along an edge of the top support member 824 that is opposite to the locking member 822. Application of the force on the top support member 824 along the direction H causes an edge adjoined to the locking member to move along the direction H', releasing the snap ledge 820 from the locking member 822.

The sliding member 802 further includes a first linear guide 826a and a second linear guide 826b that are positioned parallel and opposite to each other. The first and second linear guides 826a and 826b are protruded internally from bottom edges of the sliding member 802. In one embodiment, the apparatus 800 and its various parts may be made of a material or materials designed to ensure proper functioning of the apparatus 800 and clamping of the needle 112. Such materials may include polymers, composites, metals or the like.

Figure 8E:
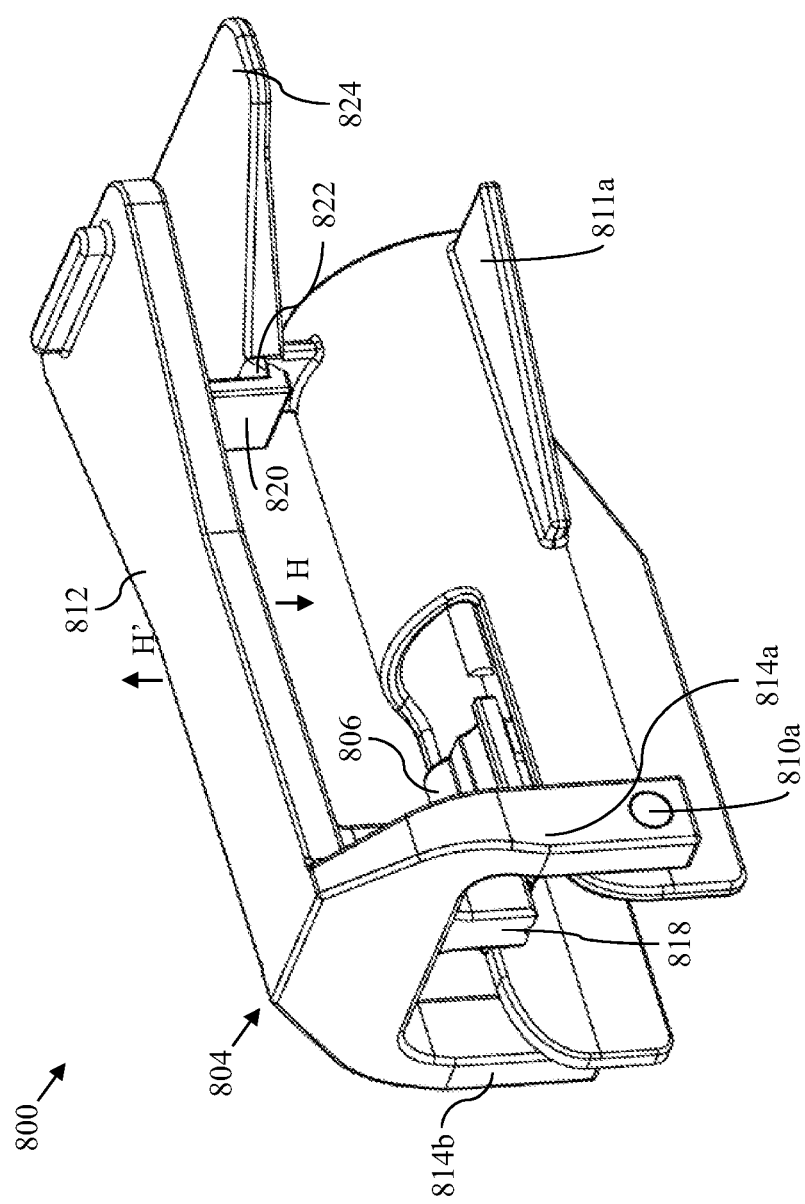
Figure 8F:
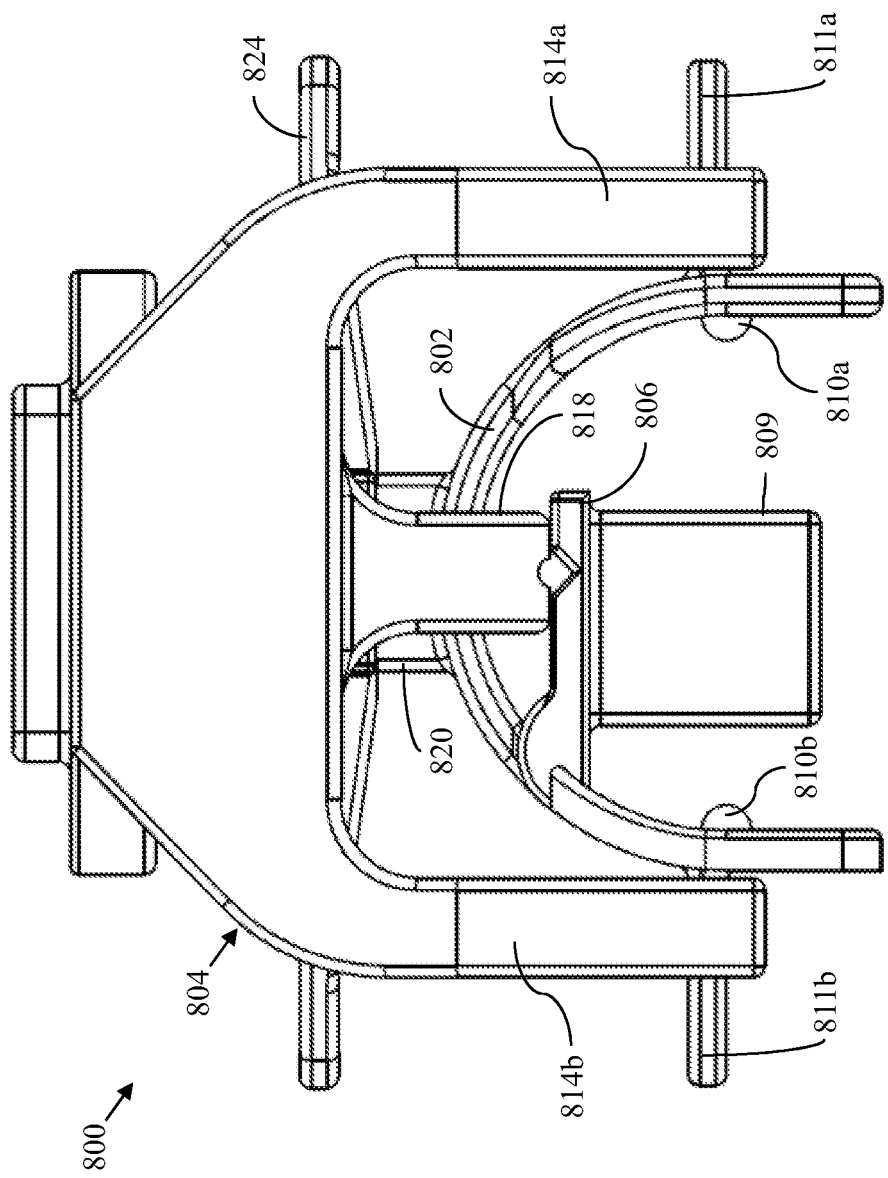
FIG. 8F illustrates a front view of the apparatus, in accordance with an exemplary embodiment of the present disclosure.

FIGS. 8D, 8E, and 8F illustrate front perspective view, rear perspective view, and front view of the apparatus 800, in accordance with an exemplary embodiment of the present disclosure. FIGS. 8E and 8D show the snap ledge 820 interlocked with (i.e., locked to) the locking member 822.

Figure 8G:
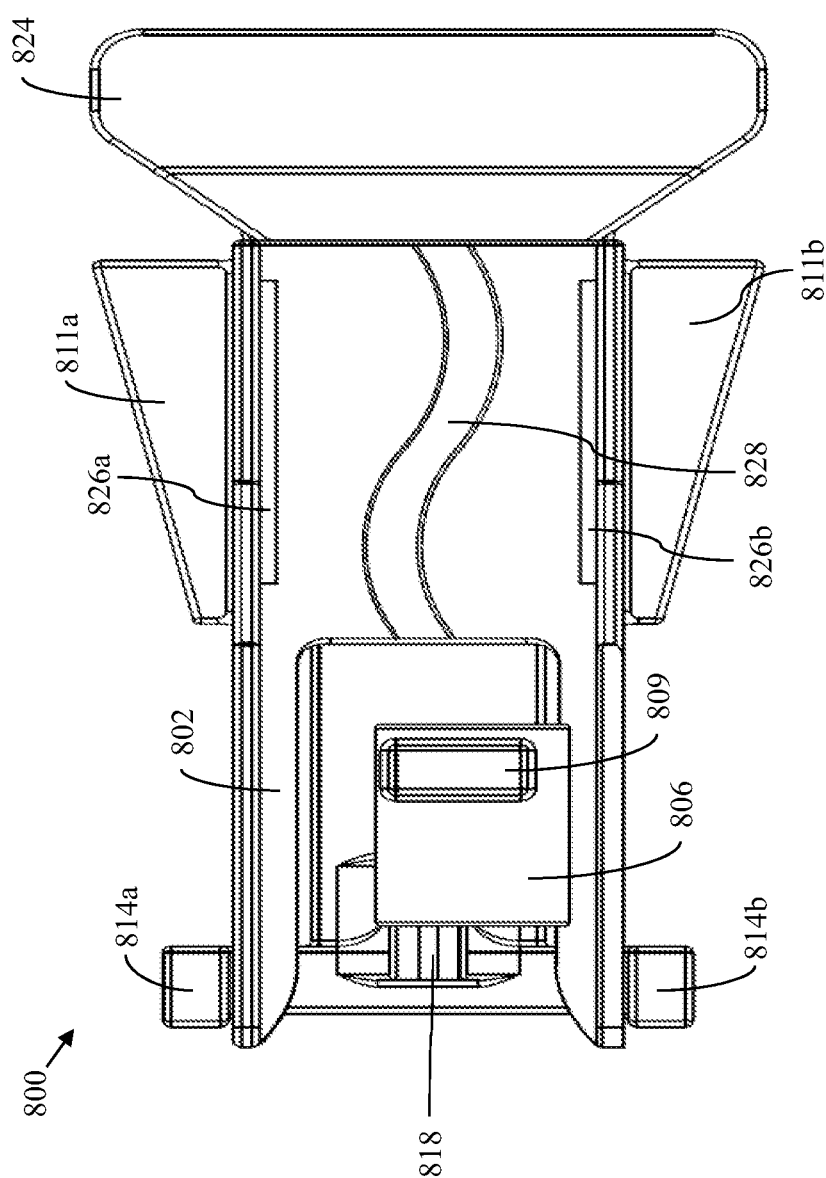
FIG. 8G illustrates a bottom view of the apparatus, in accordance with an exemplary embodiment of the present disclosure.

FIG. 8G illustrates a bottom view of the apparatus 800, in accordance with an exemplary embodiment of the present disclosure. FIG. 8F illustrates the apparatus 800 as viewed from the front of the apparatus 800. As shown in FIG. 8G, an inner surface of the sliding member 802 may include a groove 828, engraved therein, for accommodating the suture 120 when the apparatus 800 is placed atop the elongated member 102 of the suturing device 900. The groove 828 allows the suture 120 to extend out of the apparatus 800 without intervening with the operation of the apparatus 800. Moreover, the groove 828 prevents any damage to the suture 120 during the operation of the apparatus 800. The groove 828 may take various forms, including that shown in FIG. 8G as well as a straight groove.

Figure 9A:
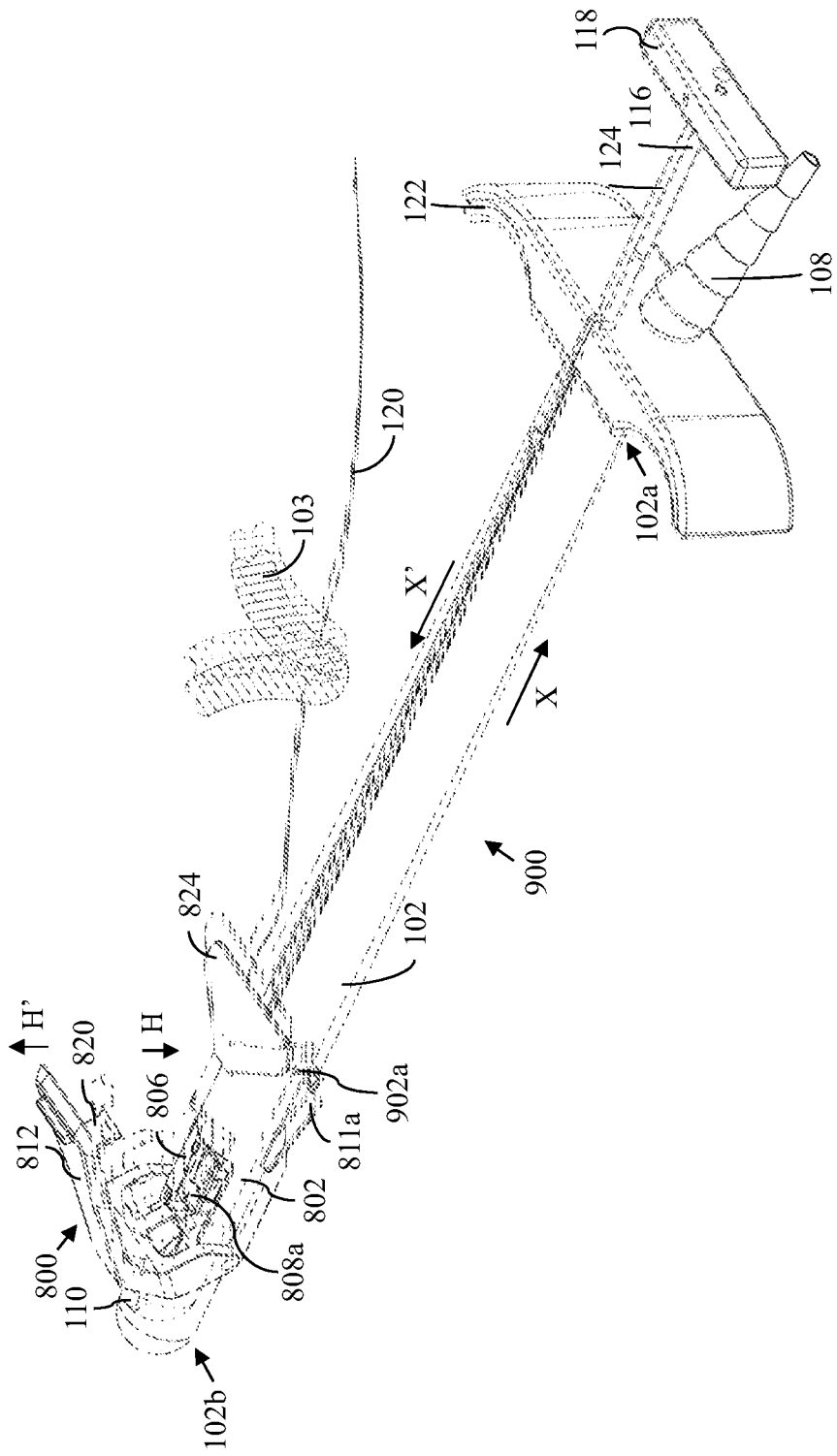
FIGS. 9A and 9B illustrate a perspective view and an enlarged view, respectively of the suturing device and the apparatus, in accordance with an exemplary embodiment of the present disclosure.
Figure 9B:
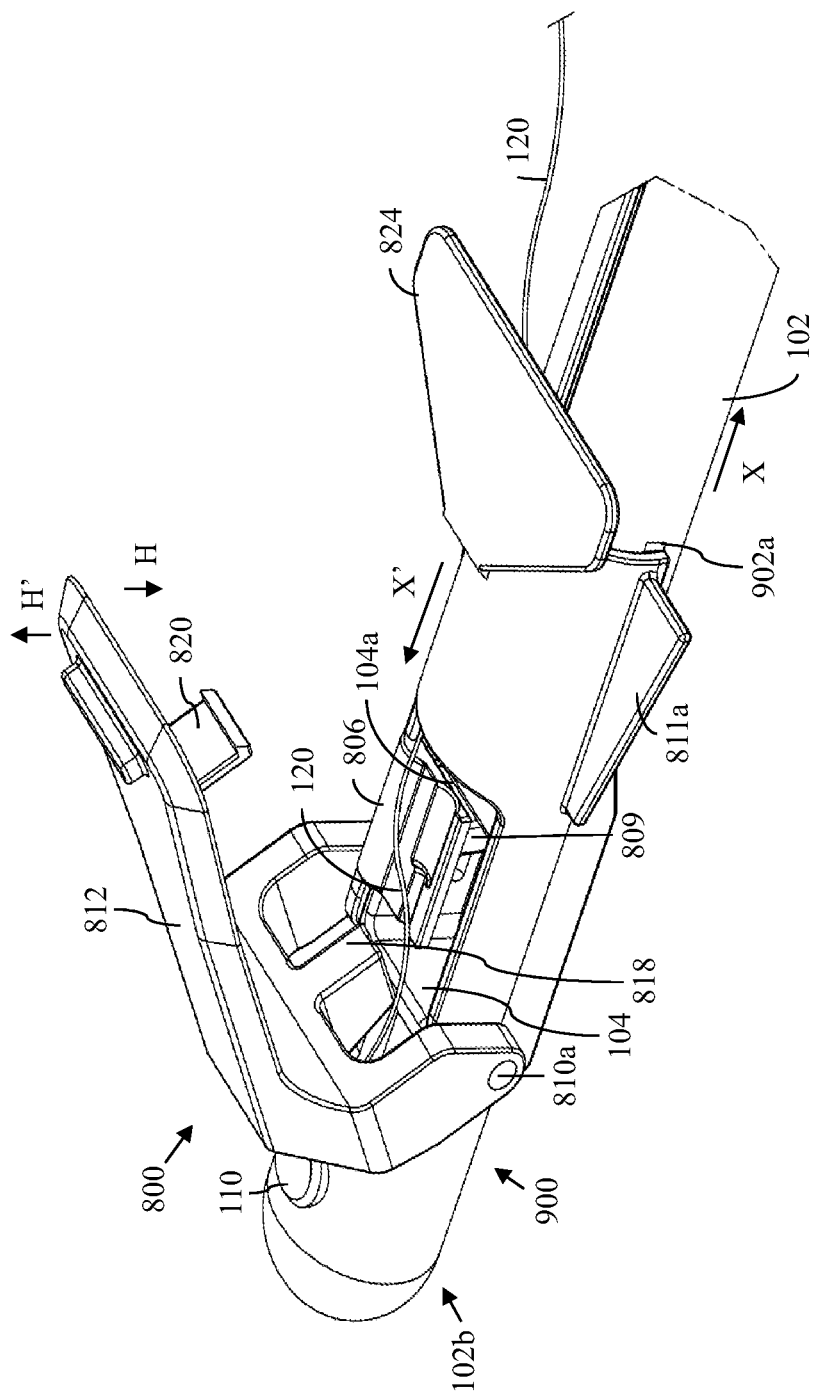

FIGS. 9A and 9B illustrate a perspective view and an enlarged view of the suturing device 900 and the apparatus 800, in accordance with an exemplary embodiment of the present disclosure. As shown in FIGS. 9A and 9B, the suturing device 900 is structurally and functionally similar to the suturing device 700 of FIG. 7A. The suturing device 900 includes a first guide slot 902a and a second guide slot 902b (not shown) opposite the first guide slot 902a formed in the elongated member 102. As shown in FIG. 9A, the suturing device 900 has been removed from the body, the needle 112 has been captured by the needle capturing assembly 110 following the suturing of the suctioned tissue 103, the operating handle 118 has been retracted from the fully advanced position to the fully retracted position, thereby retracting the needle pusher 116 and disengaging the needle pusher 116 from the needle 112 while the needle 112 remains captured by the needle capturing assembly 110, and the suctioned tissue 103 has been released from the cavity 104. It should be appreciated that the needle pusher 116 is sufficiently retracted so as to prevent the needle pusher 116 from interfering with the coupling between the apparatus 800 and the cavity 104 when the sliding member 802 is fitted to the suturing device 900. The first and second linear guides 826a and 826b of the sliding member 802 engage slidably with the first guide slot 902a and the second guide slot 902b, respectively of the suturing device 900. Further, it is assumed that the entirety of the needle 112 has passed across the second wall 104b of the cavity 104, thereby preventing the needle 112 from interfering with the fitment of the sliding member 802 to the suturing device 900. The sliding member 802 is suitably configured to slide, in the directions X and X', along the first guide slot 902a and the second guide slot 902b. The first guide slot 902a and the second guide slot 902b, in conjunction with the base 809, define a range of positions that the sliding member 802 can occupy, relative to the suturing device 900. For example, the length of the first guide slot 902a and the second guide slot 902b allows the sliding member 802 to be slid from a first position to a second position and vice-versa with respect to the elongated member 102. When the sliding member 802 is in the first position, the clamping platform 806 is positioned to receive the first end of the needle 112 extending from the needle capturing assembly 110.

Figure 9C:
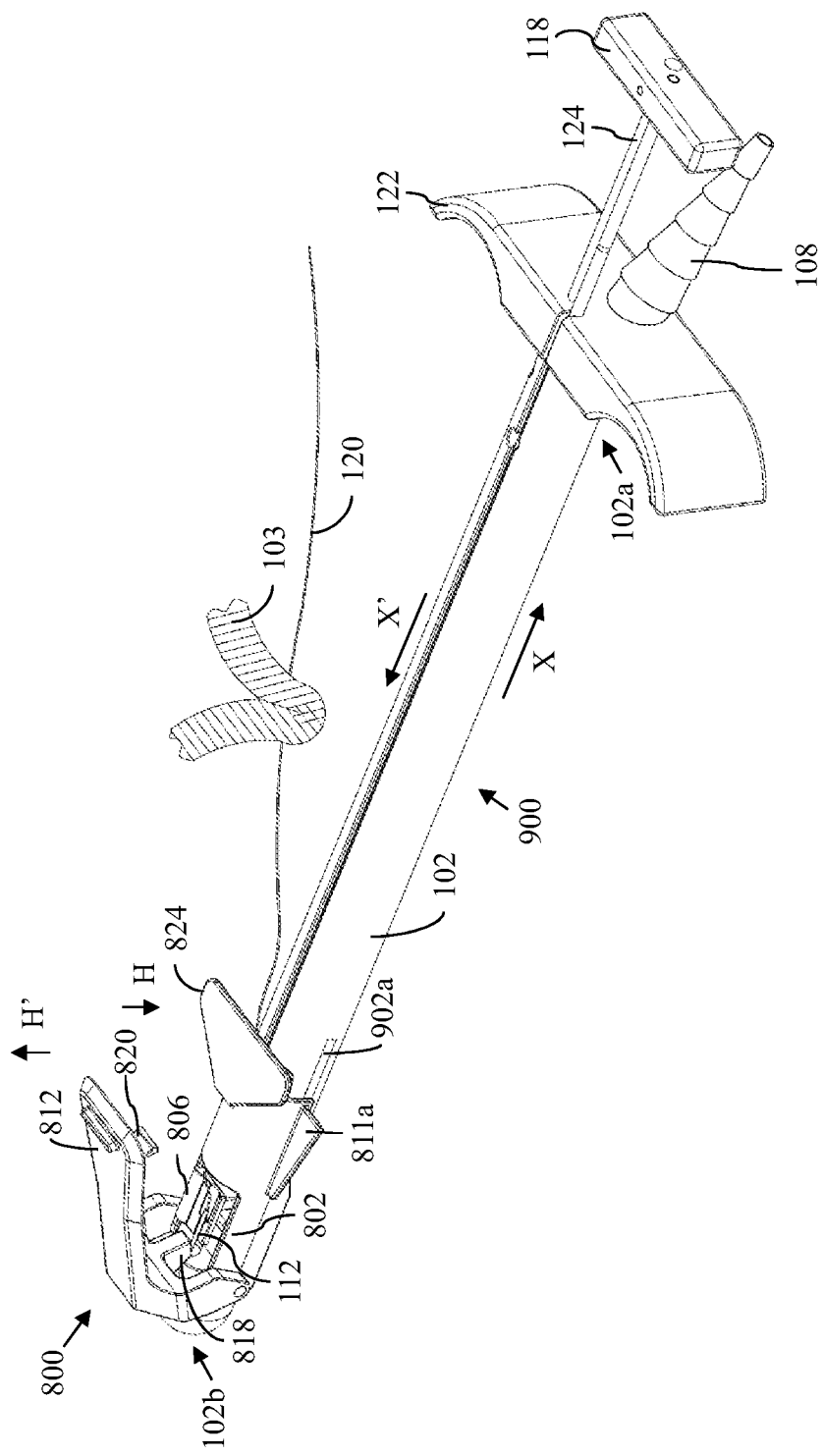
FIGS. 9C and 9D illustrate a perspective view and an enlarged view, respectively of the apparatus at a distal end of the suturing device when the apparatus is moved towards the distal end, in accordance with an exemplary embodiment of the present disclosure.
Figure 9D:
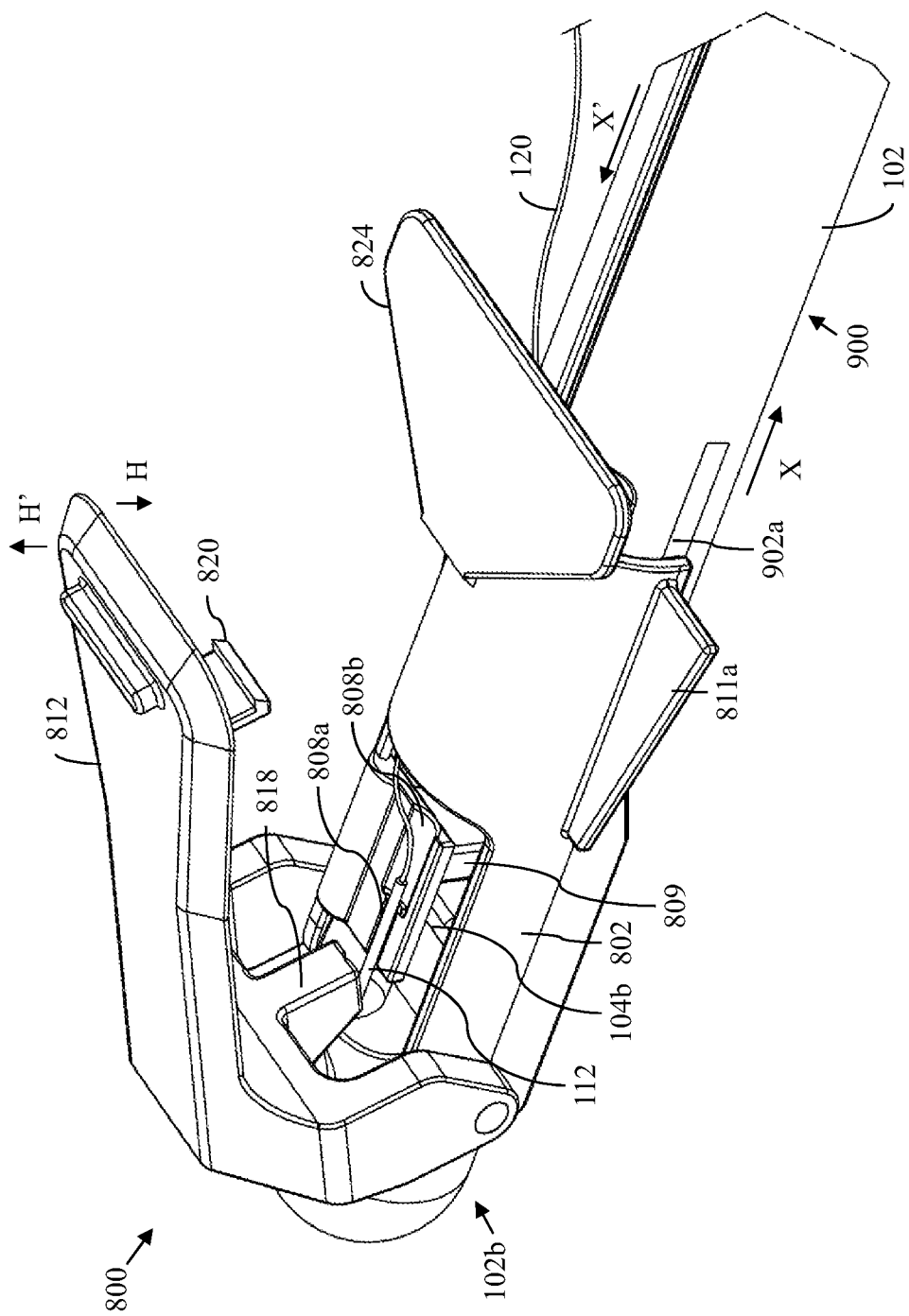

FIGS. 9C and 9D illustrate a perspective view and an enlarged view of the suturing device 900 and the apparatus 800, in accordance with an exemplary embodiment of the present disclosure. The sliding member 802 is slid to the first position of the suturing device 900. The needle 112 is captured by the needle capturing assembly 110 and the operating handle 118 is in the fully retracted position such that the needle 112 is disengaged from the needle pusher 116. FIG. 9C shows the sliding member 802 in the first position and the clamping platform 806 positioned to receive the first end of the needle 112 extending from the needle capturing assembly 110. As shown in FIG. 9D, when the sliding member 802 is in the first position, the base 809 is in contact with the second wall 104b.

Figure 9E:
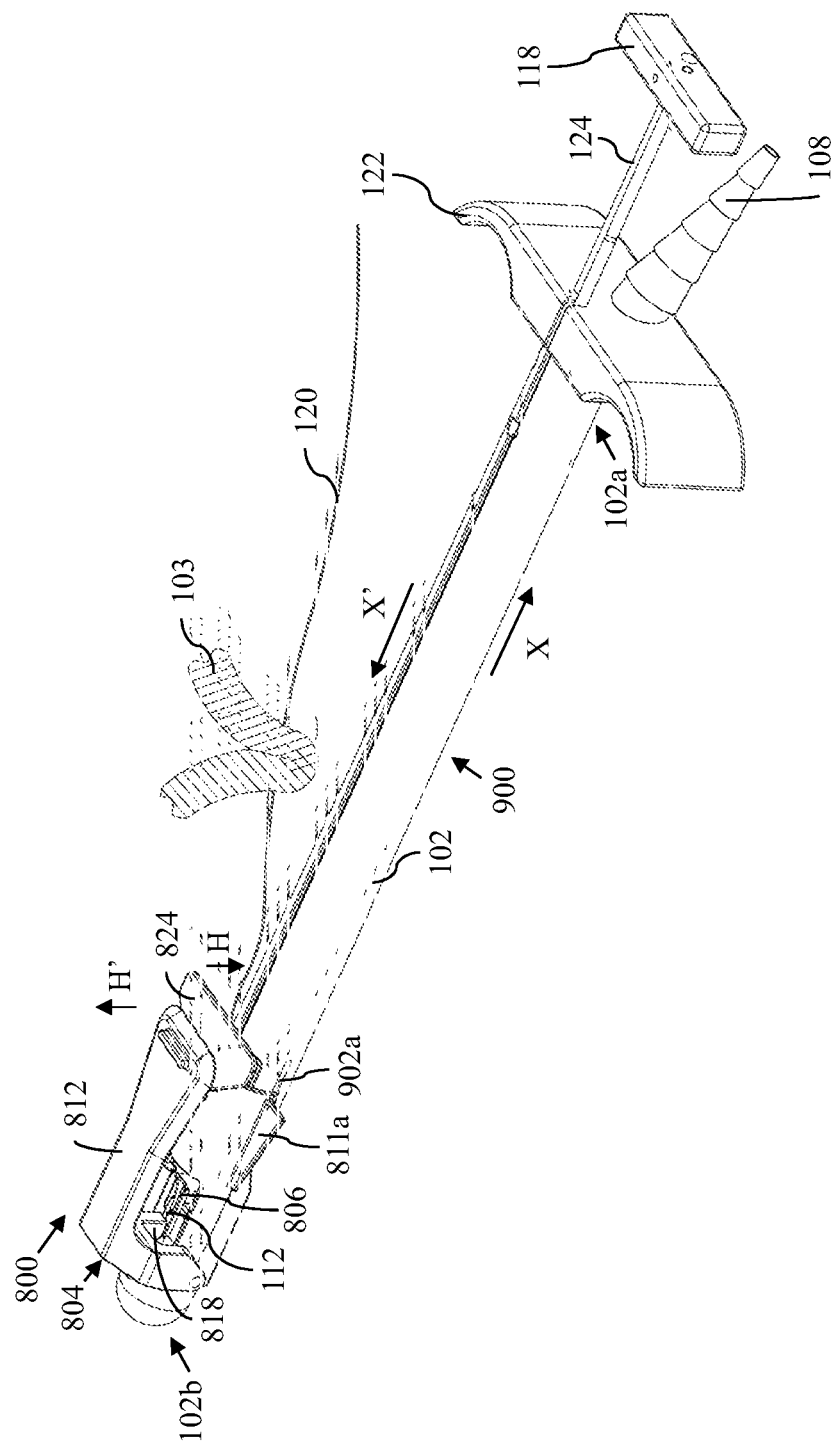
FIGS. 9E and 9F illustrate a perspective view and an enlarged view, respectively of the apparatus at the distal end of the suturing device, in accordance with an exemplary embodiment of the present disclosure.
Figure 9F:
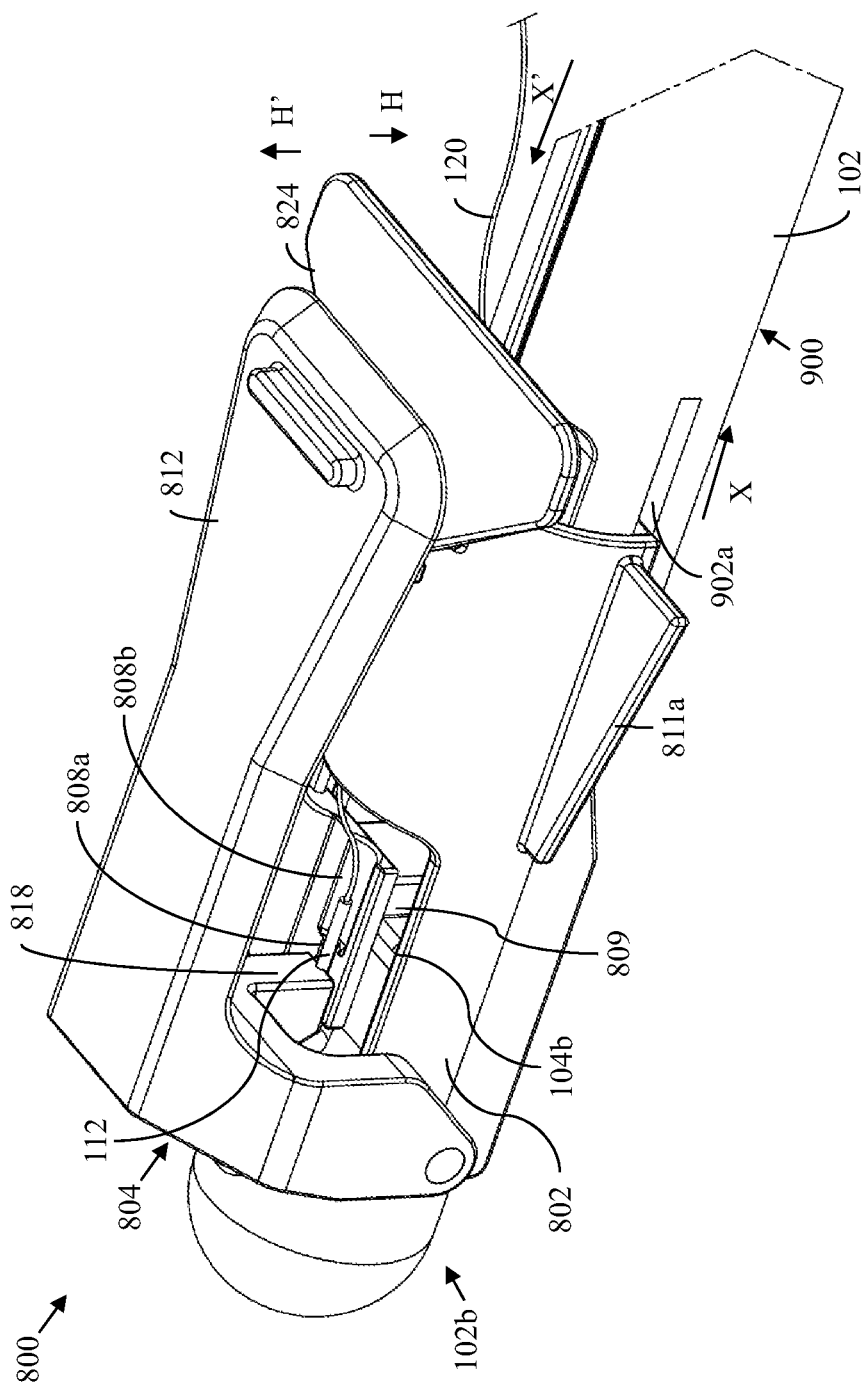

FIGS. 9E and 9F illustrate a perspective view and an enlarged view of the suturing device 900 and the apparatus 800, in accordance with an exemplary embodiment of the present disclosure. In order to extract the needle 112 from the needle capturing assembly 110 and reposition the needle 112 such that it is re-engaged by the needle pusher 116, a user of the suturing device 900 may, using the handle bar 812, move the lever 804 downwards (i.e., along the direction H) towards the clamping platform 806. As the lever 804 is moved in this manner, the first end of the needle 112 extending from the needle capturing assembly 110 is clamped, by the protruding member 818, in the channel 808a in the clamping platform 806. Once the needle 112 is positioned within the channel 808a in the clamping platform 806, the user of the suturing device 900 may lock the snap ledge 820 with the locking member 822. As shown in FIG. 9F, the sliding member 802 in the first position and the needle 112 is clamped to the clamping platform 806 by the protruding member 818.

Figure 9G:
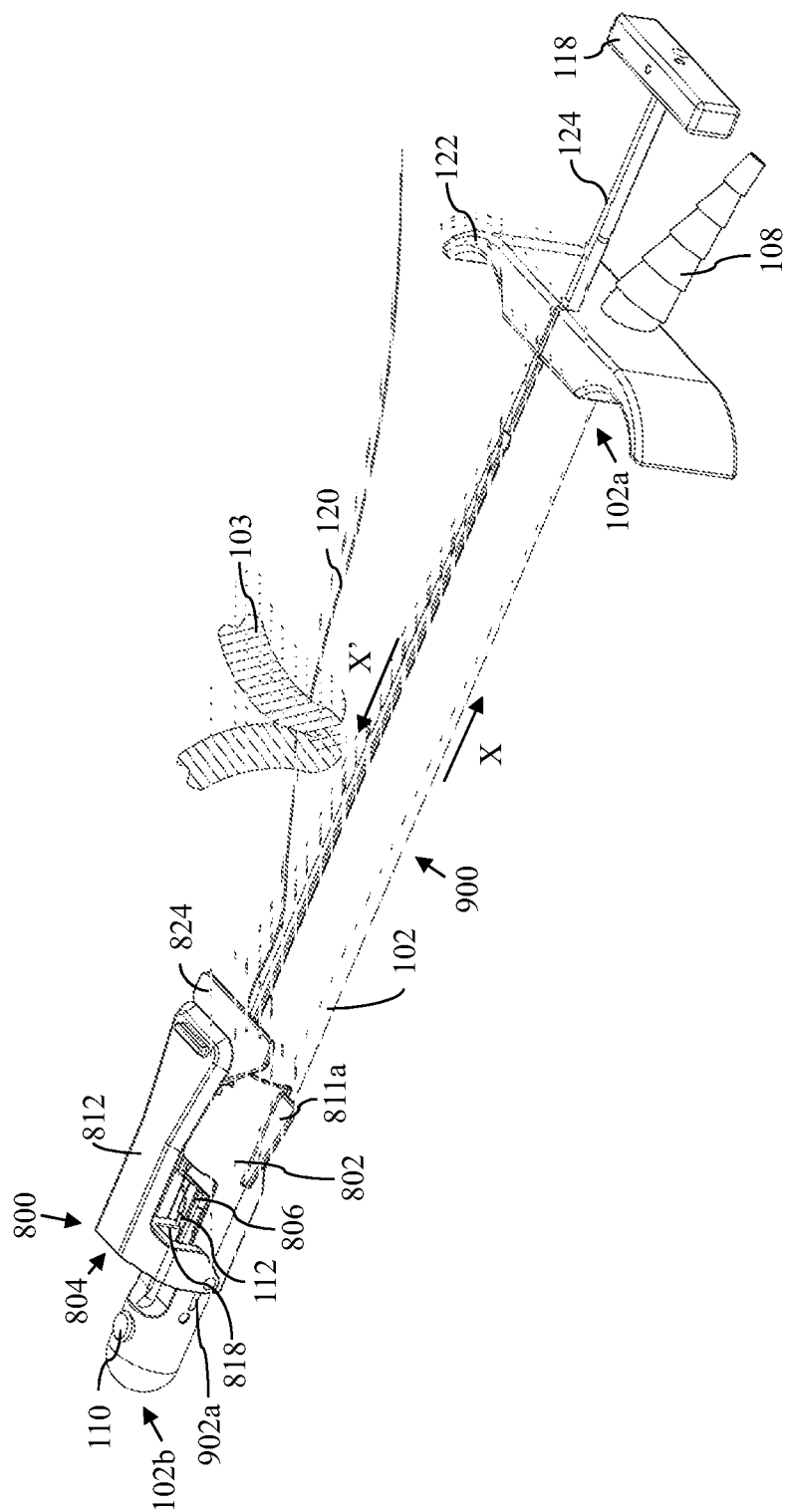
FIGS. 9G and 9H illustrate a perspective view and an enlarged view, respectively of the apparatus at the distal end of the suturing device when the apparatus is moved away from the distal end, in accordance with an exemplary embodiment of the present disclosure.
Figure 9H:
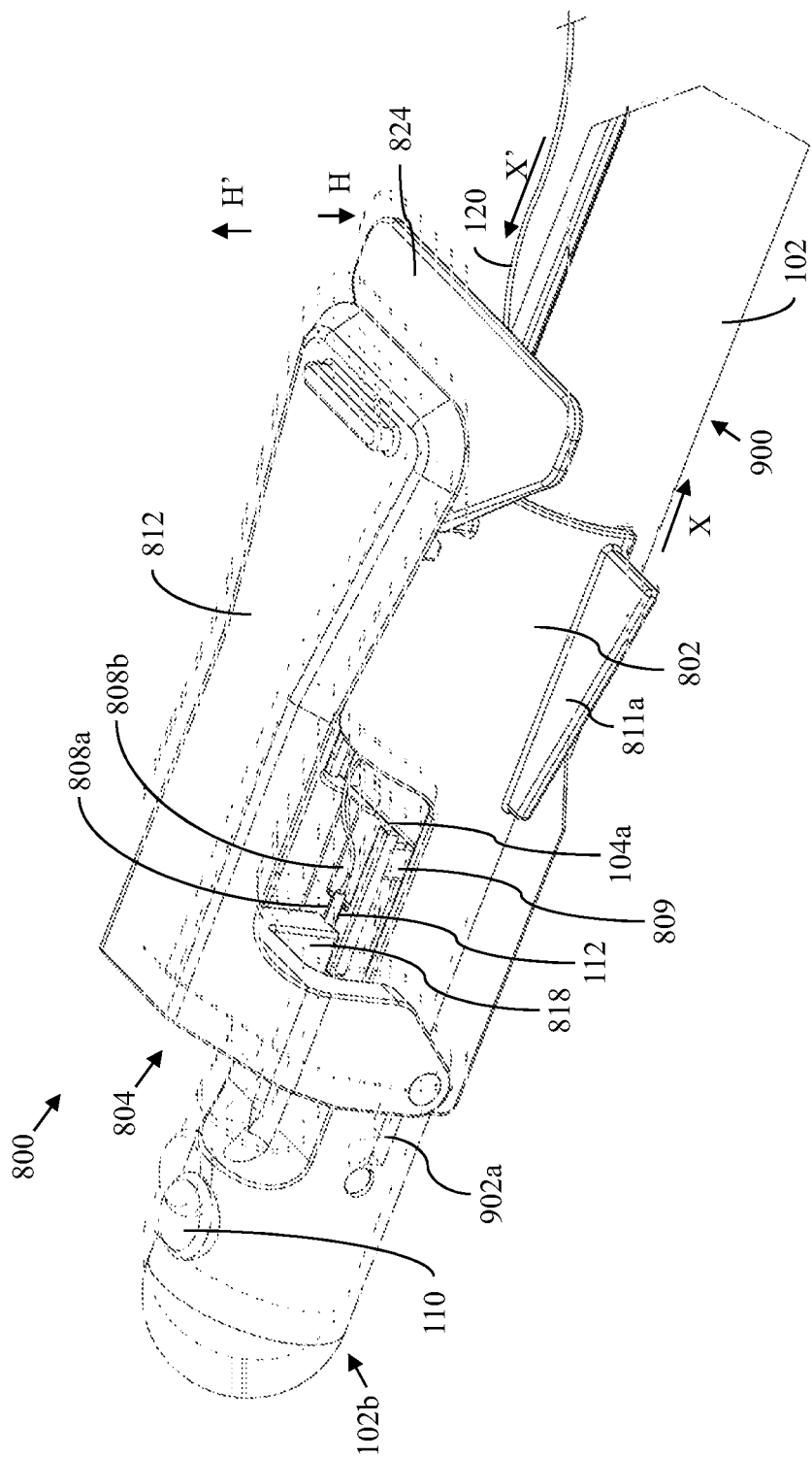

FIGS. 9G and 9H illustrate a perspective view and an enlarged view of the suturing device 900 and the apparatus 800, in accordance with an exemplary embodiment of the present disclosure. Once the needle 112 is clamped with a sufficient clamping force, the user of the suturing device 900 may slide the apparatus 800 towards the fixed handle 122, for example, by pulling the apparatus along the direction X, until the needle 112 is extracted from the needle capturing assembly 110. As shown in FIG. 9H, the sliding member 802 is in the second position and the needle 112 is clamped to the clamping platform 806 by the protruding member 818.

Figure 9I:
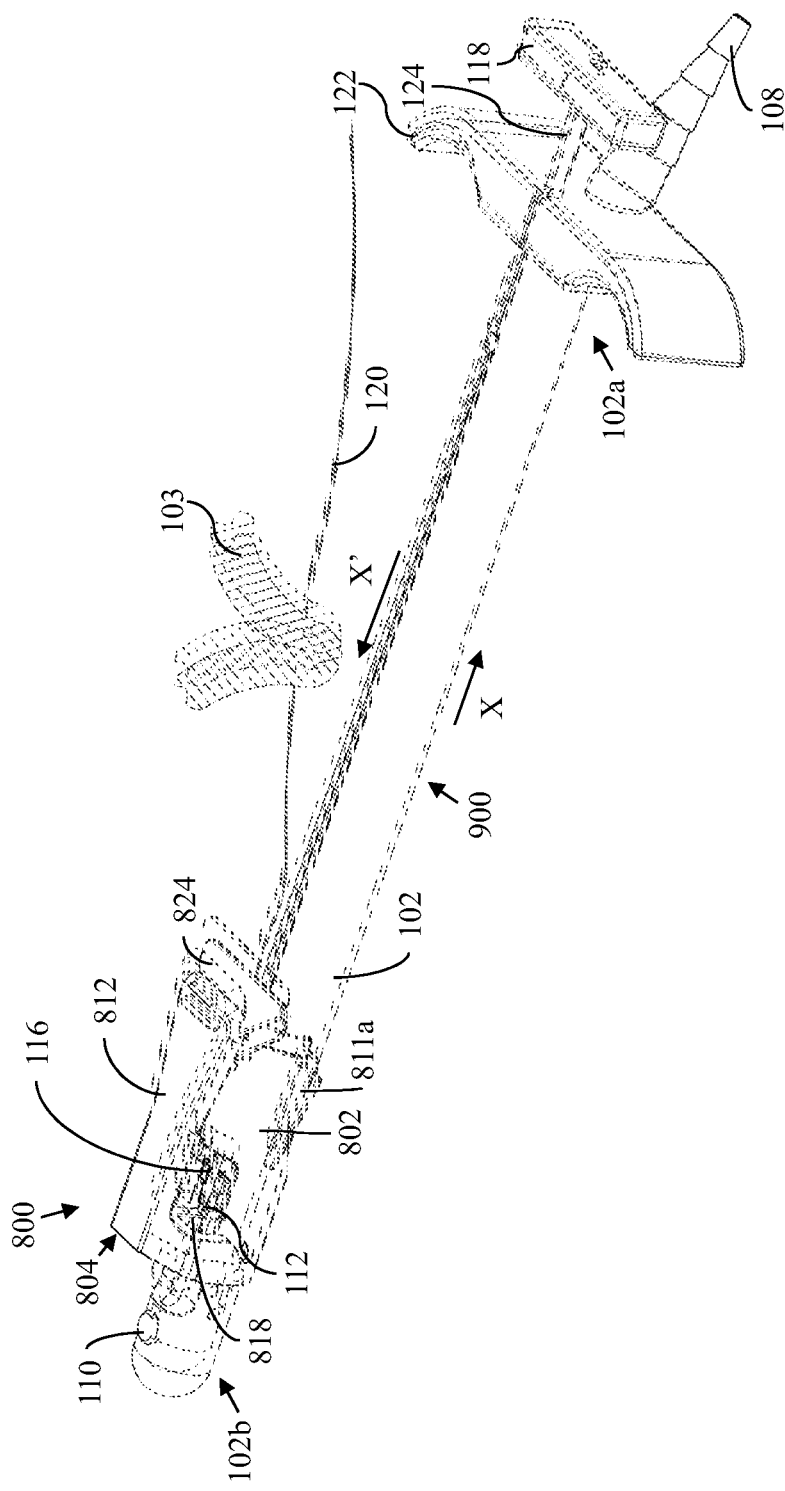
FIGS. 9I and 9J illustrate a perspective view and an enlarged view of the apparatus and the suturing device when an operating handle is at a fully advanced position, in accordance with an exemplary embodiment of the present disclosure.
Figure 9J:
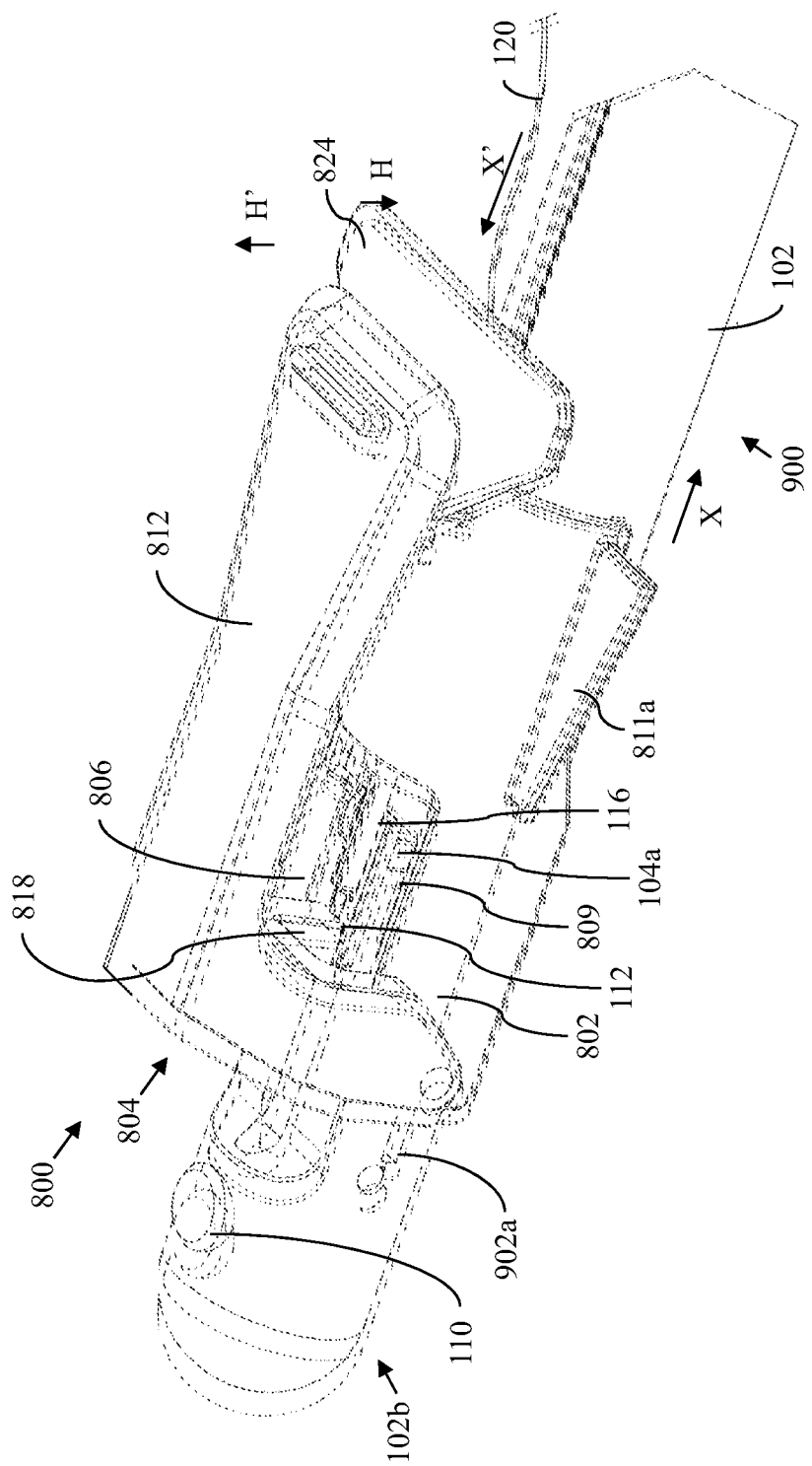

FIGS. 9I and 9J illustrate a perspective view and an enlarged view of the suturing device 900 and the apparatus 800, in accordance with an exemplary embodiment of the present disclosure. In accordance with an exemplary embodiment of the present disclosure, once the needle 112 has been extracted from the needle capturing assembly 110, the operating handle 118 may be progressively advanced from the fully retracted position towards the fixed handle 122, thereby advancing the needle pusher 116 until the needle pusher 116 re-engages with the end of the needle 112. As shown in FIGS. 9I and 9J, the needle pusher 116 is received in the channel 808b of the clamping platform 806. Following the re-engagement of the needle 112 with the needle pusher 116, the user of the suturing device 900 may disengage the snap ledge 820 from the locking member 822. In other words, the user may release the interlocking between the snap ledge 820 from the locking member 822 by moving in the direction H' the back edge of the top support member 824, that is opposite the locking member 822. Upon disengaging the snap ledge 820 from the locking member 822, the protruding member 818 no longer clamps the needle 112.

Subsequently, the operating handle 118 may be retracted towards the fully retracted position such that the needle 112 is in the position shown in FIG. 1A. Then, the apparatus 800 may be detached from the suturing device 900, and the suturing device 900 and the apparatus 800 may be operated as described above to administer one or more additional passes of the needle 112 and suture 120 through tissue 103 (or another tissue) and thereby make multiple suture passes.

Figure 10A:
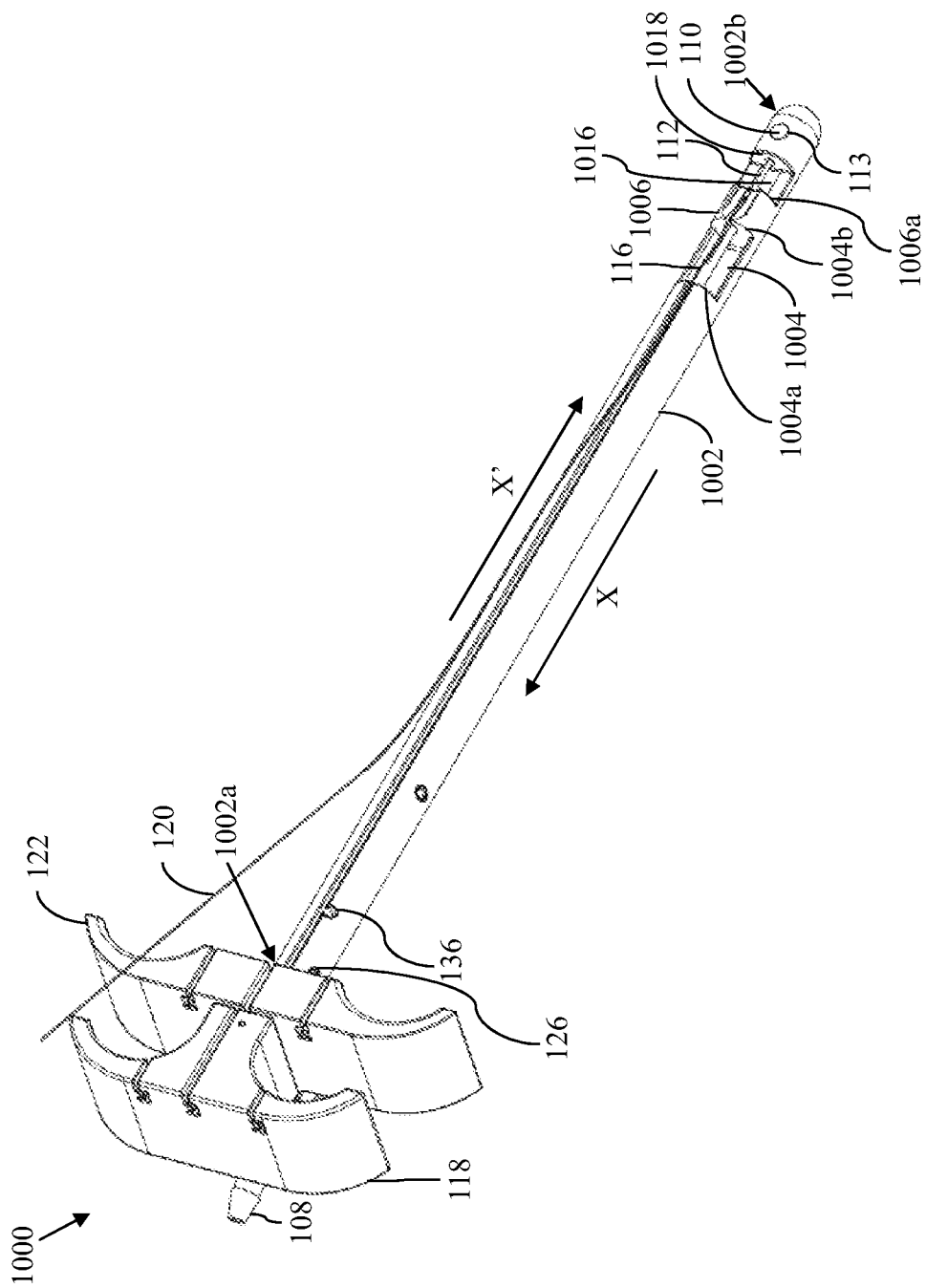
FIGS. 10A-10C illustrate a perspective side view, a perspective top view, and a cross-sectional side view, respectively, of a suturing device, in accordance with an exemplary embodiment of the present disclosure.
Figure 10B:
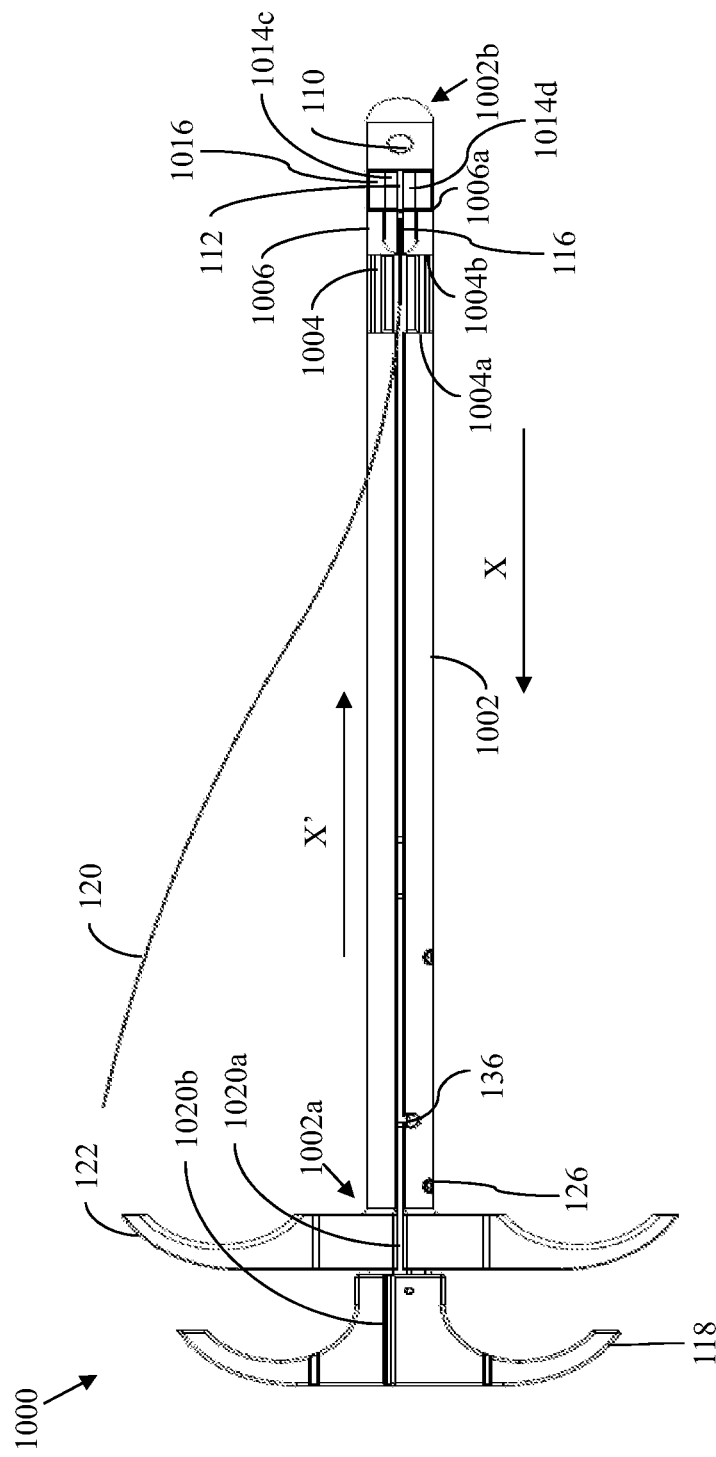
Figure 10C:
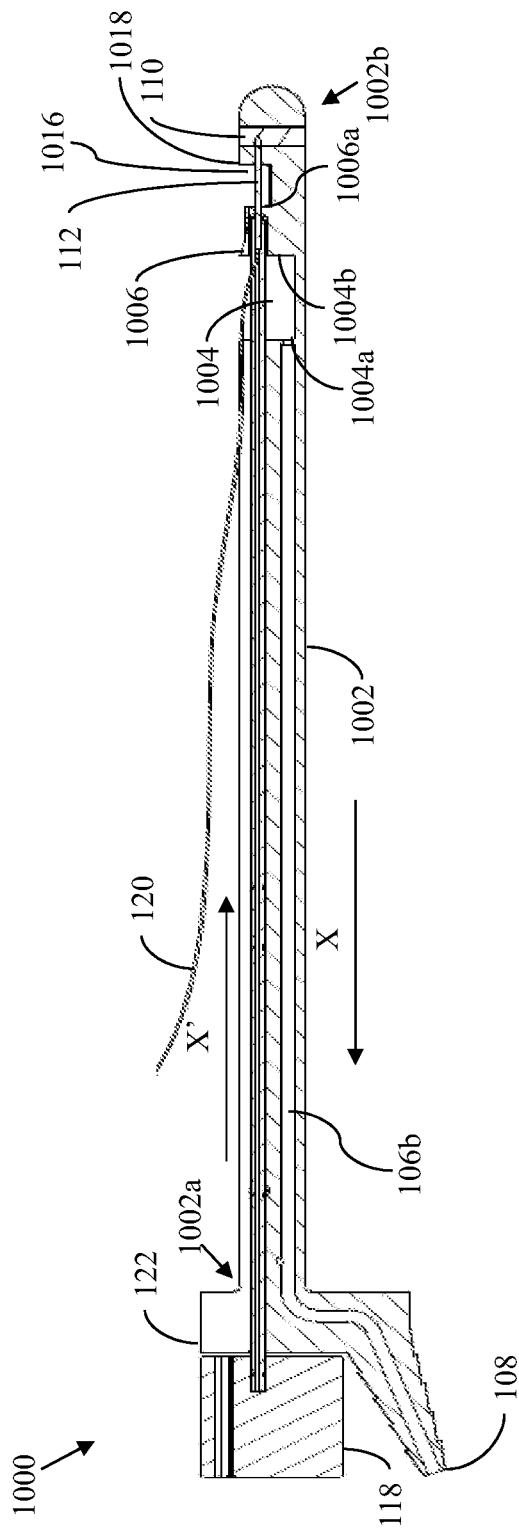

FIGS. 10A-10C illustrate a perspective side view, a perspective top view, and a cross-sectional side view, respectively, of a suturing device 1000, in accordance with an exemplary embodiment of the present disclosure. As shown in FIG. 10A, the suturing device 1000 is structurally and functionally similar to the suturing device 100 of FIG. 1. Differences between the suturing device 1000 and the suturing device 100 will be described below.

As shown in FIGS. 10A-10C, the suturing device 1000 includes an elongated member 1002 having a proximal end 1002a and a distal end 1002b ("proximal" and "distal" being from the perspective of a user of the suturing device 1000). Like to the elongated member 102 of the suturing device 100, the elongated member 1002 of the suturing device 1000 further includes a cavity 1004 for capturing tissue when a vacuum is applied to the cavity 1004. Preferably, the cavity 1004, like the cavity 104 of the suturing device 100, is dimensioned to suit a particular application and to accommodate the type and amount of tissue that is to be captured. For example, the cavity 1004 may include a first wall 1004a (i.e., a front wall from the perspective of the user of the suturing device 1000; shown in FIG. 10C) at a first end of the cavity 1004 and a second wall 1004b (i.e., a rear wall from the perspective of the user of the suturing device 1000 shown in FIG. 10C) at a second end of the cavity 1004 parallel and opposite to the first wall 1004a. As was the case with the cavity 104, the cavity 1004 may have other shapes, such as an ovoid, cylindrical, cuboid, pyramidal, parabolic, conical, or free-form shape.

However, unlike the elongated member 102 of the suturing device 100, the elongated member 1002 of the suturing device 1000 further includes a guide structure 1006 provided between the cavity 1004 and the needle capturing assembly 110. As will be explained in more detail below, the guide structure 1006 maintains alignment of the needle pusher 116 and the needle 112 as they pass through tissue captured by the cavity 1004 and as the needle 112 is captured by the needle capturing assembly 110. The guide structure 1006 also maintains alignment of the needle pusher 116 and the needle 112 as the needle 112 is extracted from the needle capturing assembly 110 and repositioned to be carried by the needle pusher 116 after the needle 112 has been captured by the needle capturing assembly 110 and the needle pusher 116 and the needle 112 have been separated. The guide structure 1006 also serves to limit the linear movement of the needle pusher 116 (and thus the needle 112 when it is carried by the needle pusher 116) in the direction of the needle capturing assembly 110.

Preferably, the guide structure 1006 is formed such that the second wall 1004b of the cavity 1004 defines a first end surface of the guide structure 1006 (shown in FIGS. 10D-10F) and a wall 1006a (shown in FIGS. 10D-10F) that is opposite to the second wall 1004b defines a second end surface of the guide structure 1006. The guide structure 1006 includes a first channel 1008a (shown in FIGS. 10D-10H) extending from the second wall 1004b of the cavity 1004 towards, but not through, the wall 1006a. The guide structure 1006 also includes a second channel 1008b (shown in FIGS. 10D-10F) extending from the wall 1006a towards the second wall 1004b until it meets with the first channel 1008a. Preferably, the first channel 1008a and the second channel 1008b are concentric (e.g., coaxial) and a path defined by the first channel 1008a and the second channel 1008b forms an extension of the working channel 106a.

The first channel 1008a is preferably dimensioned such that the needle pusher 116 can be moved axially through the first channel 1008a with minimal friction with walls of the first channel 1008a while maintaining a desired amount of concentric alignment with the first channel 1008a, taking into account tolerances of materials used in the design of the suturing device 1000. Further, the first channel 1008a is preferably wider at the second wall 1004b than it is at a point where the first channel 1008a meets the second channel 1008b. To accommodate this change in the diameter of the first channel 1008a, a portion of the first channel 1008a proximate the second wall 1004b may be shaped in a form of a frustum of a cone. Alternatively, the first channel 1008a, for its entire length, may be shaped in the form of a frustum of a cone. By increasing the diameter of the first channel 1008a at the second wall 1004b with respect to the diameter of the first channel 1008a at the point where it meets the second channel 1008b, one can minimize the chance that the distal tip of the needle pusher 116 (or the distal tip of the needle 112, when carried by the needle pusher 116), when being moved in the direction X', strikes the second wall 1004b, and facilities the unobstructed movement of both the needle pusher 116 and the needle 112 through the first channel 1008a in the direction X'.

The second channel 1008b is preferably dimensioned such that the needle 112 can be moved axially through the second channel 1008b with minimal friction with walls of the second channel 1008b while maintaining a desired amount of concentric alignment with the second channel 1008b, taking into account tolerances of materials used in the design of the suturing device 1000. Further, preferably the diameter of the second channel 1008b is less than the diameter of the needle pusher 116. It should be appreciated that when the diameter of the second channel 1008b is less than the diameter of the needle pusher 116, a junction 1010 between the first channel 1008a and the second channel 1008b (shown in FIGS. 10D and 10G) acts as a stop for the needle pusher 116 when the needle pusher 116 is moved towards the distal end 1002b of the elongated member 1002. In other words, the needle pusher 116 may pass through the first channel 1008a until it reaches the second channel 1008b. As a result, only the needle 112 may pass through the second channel 1008b.

Preferably, the first channel 1008a includes an opening 1012 (shown in FIGS. 10D, 10E, and 10I) that extends along a length of the first channel 1008a to allow the suture 120 to exit the first channel 1008a as the needle pusher 116 and the needle 112 move through the first channel 1008a and the second channel 1008b. In another embodiment, the opening 1012 may also extend along a length of the second channel 1008b.

In addition, a top surface 1006b of the guide structure 1006 further includes a first recessed portion 1014a and a second recessed portion 1014b that are dimensioned to facilitate the use of an apparatus (e.g., a hemostat, forceps, needle holder, or the like) for extracting the needle 112 from the needle capturing assembly 110 as will be described in more detail below. Preferably, each of the first recessed portion 1014a and the second recessed portion 1014b is an angular recess formed on either side of the opening 1012 as shown. Also, the elongated member 1002 preferably includes an opening 1016 formed between the guide structure 1006 and the needle capturing assembly 110 to further facilitate the use of an apparatus (e.g., a hemostat, forceps, needle holder, or the like) for extracting the needle 112 from the needle capturing assembly 110 and positioning the needle 112 into the needle pusher 116 during operation of the suturing device 1000. A bottom surface of the opening 1016 may also include a third recessed portion 1014c and a fourth recessed portion 1014d (shown in FIGS. 10B, 10D, and 10G-10I) to accommodate such an apparatus.

Figure 10D:
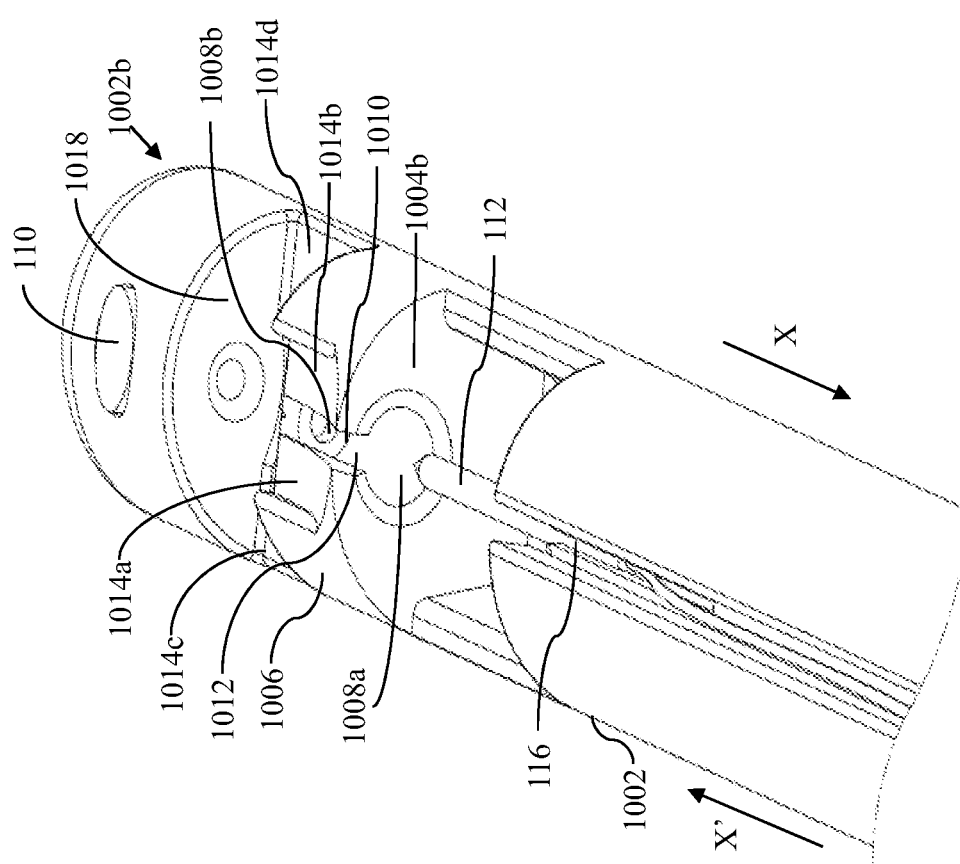
FIG. 10D illustrates an enlarged view of a distal end of the suturing device when an operating handle of the suturing device is in a partially advanced position, in accordance with an exemplary embodiment of the present disclosure.
Figure 10E:
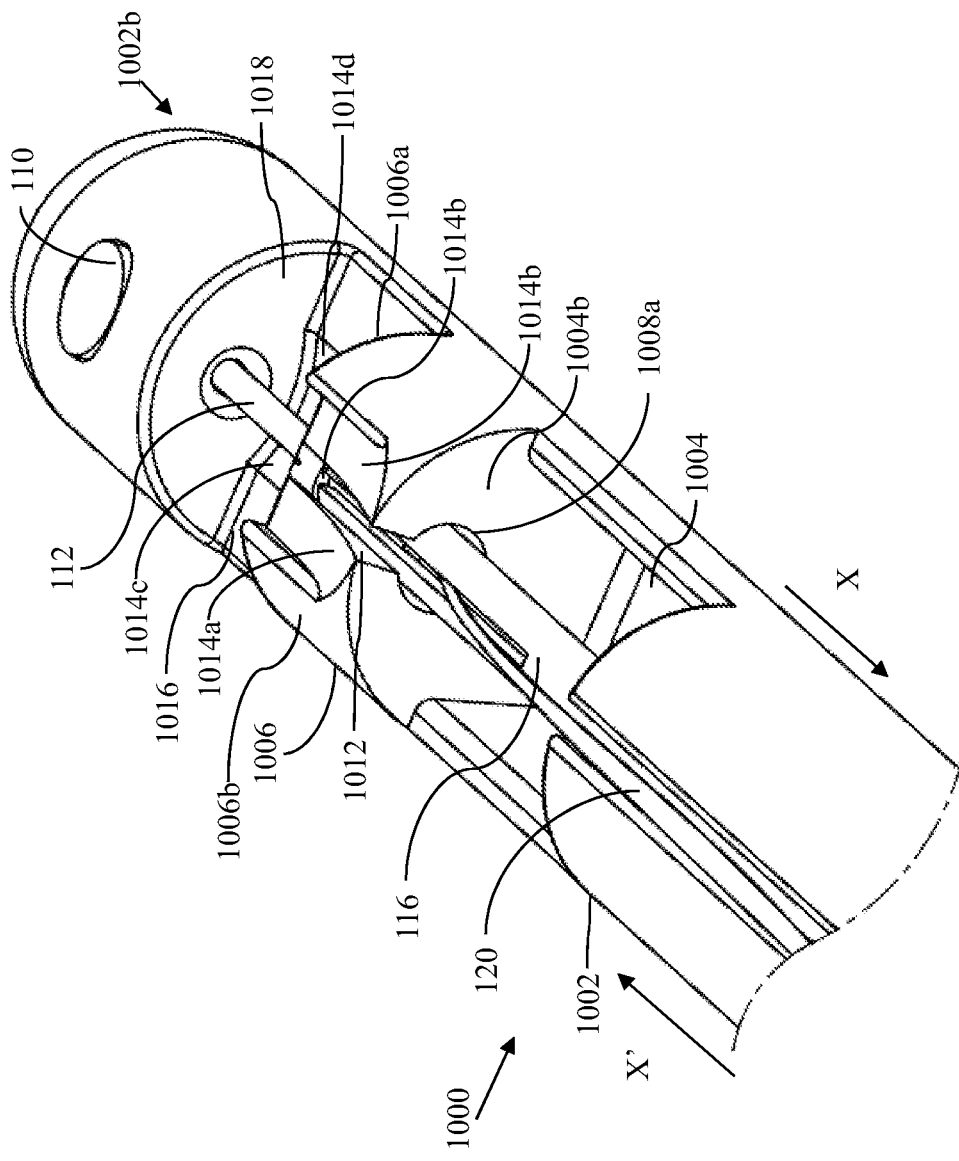
FIG. 10E illustrates an enlarged view of the distal end of the suturing device of when the operating handle is in a fully advanced position, in accordance with an exemplary embodiment of the present disclosure.
Figure 10F:
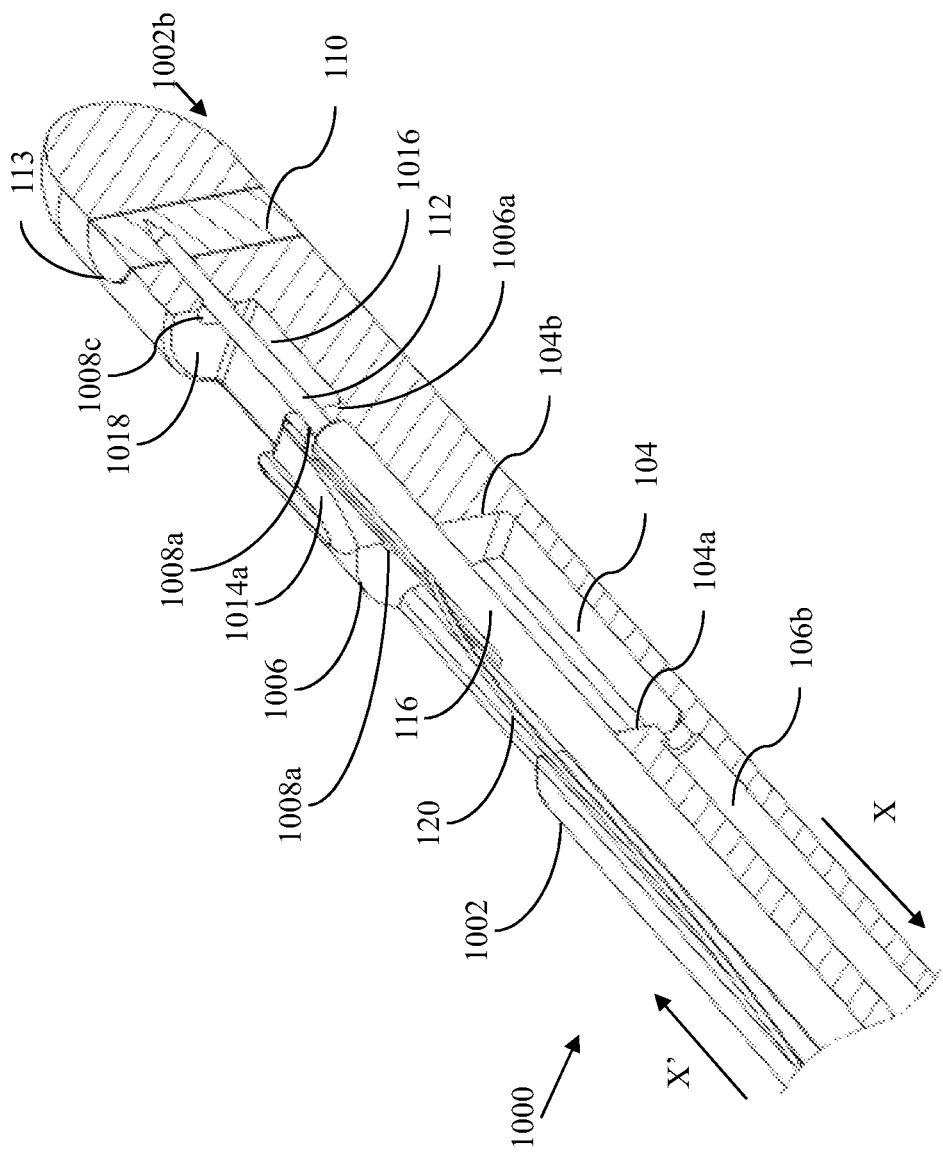
FIG. 10F illustrates an enlarged cross sectional side view of the distal end of the suturing device when the operating handle is moved to the fully advanced position.
Figure 10G:
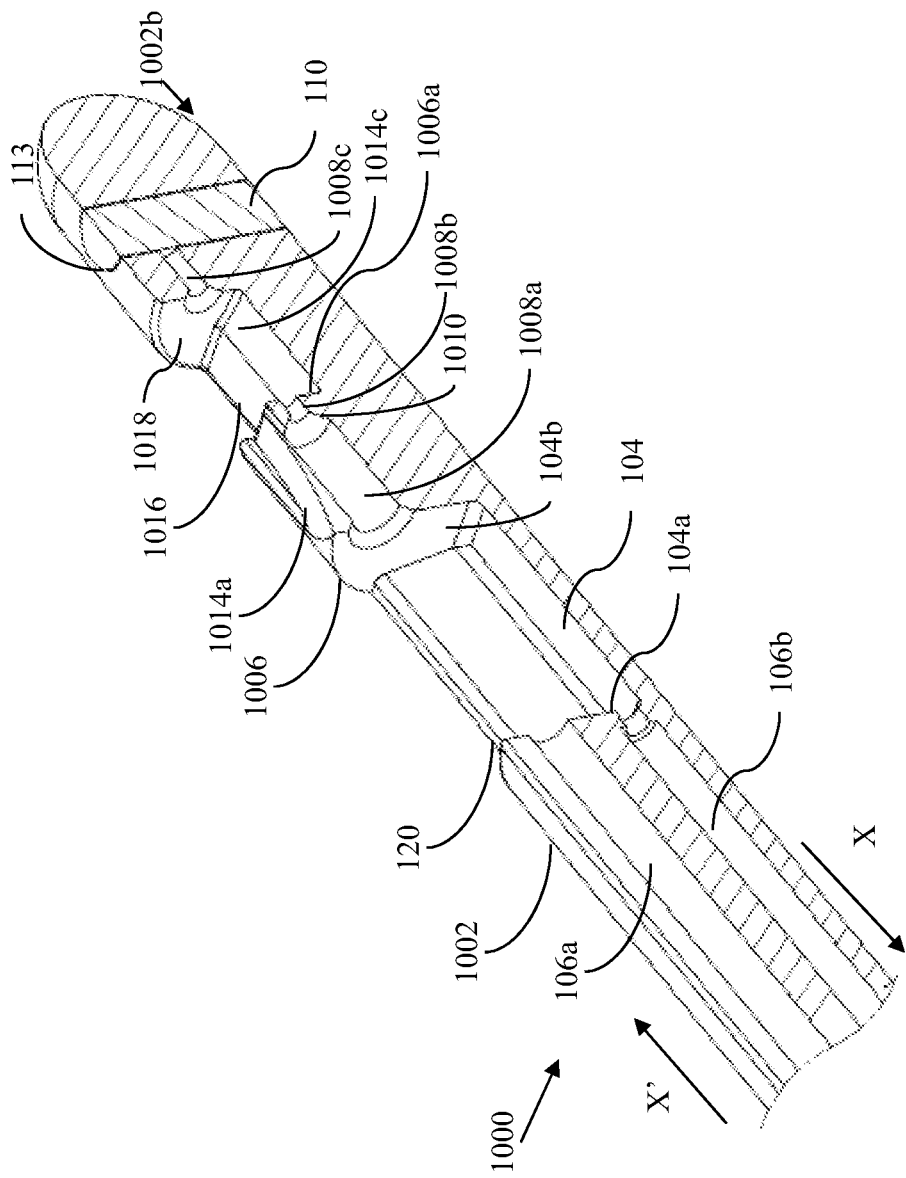
FIG. 10G illustrates an enlarged cross sectional side view of the distal end of the suturing device, in accordance with an exemplary embodiment of the present disclosure.

The elongated member 1002 further includes a third channel 1008c extending from a third wall 1018 towards the needle capturing assembly 110 (shown in FIG. 10G). Preferably, the first channel 1008a, the second channel 1008b, and the third channel 1008c are concentric (e.g., coaxial) with respect to the working channel 106 such that the first channel 1008a, the second channel 1008b, and the third channel 1008c form an extension of the working channel 106a.

The third channel 1008c is preferably dimensioned such that the needle 112 can be moved axially through the third channel 1008c with minimal friction with walls of the third channel 1008c while maintaining a desired amount of concentric alignment with the third channel 1008c, taking into account tolerances of materials used in the design of the suturing device 1000. Further, the third channel 1008c is preferably wider at the third wall 1018 than it is at a point where the third channel 1008c meets the opening 113 housing the needle capturing assembly 110. To accommodate this change in the diameter of the third channel 1008c, the third channel 1008c may, for part of its length proximate the third wall 1018, be shaped in a form of a frustum of a cone as was the case with the embodiment of the first channel 1008a described above. Alternatively, the third channel 1008c may, for its entire length, be shaped in the form of a frustum of a cone as was the case with the embodiment of the first channel 1008a. By increasing the diameter of the third channel 1008c at the third wall 1018 with respect to the diameter of the third channel 1008c at the point where it meets the opening 113, one can minimize the chance that the distal tip of the needle 112 when being moved in the direction X', strikes the third wall 1018 and facilities the unobstructed movement of the needle 112 through the third channel 1008c in the direction X'.

During operation of the suturing device 1000, the user may push and/or pull the operating handle 118, using the fixed handle 122 as leverage, to control the movement of the needle pusher 116 within the working channel 106a. Prior to such movement, the user may position the suture 120 in one or more of a set of cutouts including a first cutout 1020a and a second cutout 1020b (labelled in FIG. 10B) formed in the fixed handle 122 and the operating handle 118, respectively, to avoid entanglement of the suture 120 during operation of the suturing device 1000. As was the case with the other embodiments described above, the user operating the suturing device 1000 may move the operating handle 118 from the fully retracted position towards the fixed handle 122 of the suturing device 1000, until the operating handle 118 reaches its fully advanced position. FIGS. 10A-10C illustrate the suturing device 1000 when the operating handle 118 is at the fully advanced position. When the operating handle 118 is in the fully advanced position, the operating handle 118 is preferably in contact with the fixed handle 122. The longitudinal advancement of the operating handle 118 towards the fixed handle 122 forces the needle pusher 116, and, consequently, the needle 112 and the suture 120, to advance longitudinally from a current position towards the distal end 1002b of the elongated member 1002. As the needle pusher 116, the needle 112, and the suture 120 are advanced, the needle 112, the suture 120, and the needle pusher 116 pass over the cavity 1004. In doing so, the needle pusher 116, the needle 112 and the suture 120 may penetrate the tissue 103 that has been suctioned into the cavity 1004 by the vacuum applied to the suction channel 106b as described above in connection with the other embodiments.

Eventually, the needle pusher 116, the needle 112 and the suture 120 will pass through the first channel 1008a until the needle pusher 116 reaches the junction 1010 between the first channel 1008a and the second channel 1008b. At this point, only the needle 112 and the suture 120 (but not the needle pusher 116) have passed through the second channel 1008b and the third channel 1008c, and needle 112 has been captured by the needle capturing assembly 110. Preferably, once the needle 112 is captured by the needle capturing assembly 110, the needle 112 extends from the needle capturing assembly 110 through the entirely of the third channel 1008c, the entirety of the second channel 1008b, and at least part way into the first channel 1008a.

Once the needle 112 has been captured by the needle capturing assembly 110, the operating handle 118 is retracted in the direction X such that the needle pusher 116 moves from the fully advanced position to the intermediate position while the needle 112 remains captured by the needle capturing assembly 110 and the tissue 103 remains captured in the cavity 1004. As a result, the needle 112 disengages from the needle pusher 116. Full retraction of the operating handle 118, such that the needle pusher 116 moves from the intermediate position to the fully retracted position, causes the blocking member 124 to also retract such that it no longer blocks the first aperture 126. As a result, the vacuum is no longer applied to the cavity 1004 and the suctioned tissue 103 is released from the cavity 1004 while the suture 120 remains passed through the tissue 103. The user may then remove the suturing device 1000 from the patient's body.

Once the suturing device 1000 has been removed from the patient's body, the operating handle 118 may be progressively advanced from the fully retracted position towards the fixed handle 122 in the direction X', thereby advancing the needle pusher 116 until the needle pusher 116 is positioned within the first channel 1008*a* and re-engages with the portion of the needle 112 that was left to extend into the first channel 1008*a* as described above. Preferably, the needle pusher 116 is advanced until the second detent 132*b* of the needle pusher 116 engages with the ball 138*b* of the ball-spring detent mechanism 130 to create the audible and/or tactile feedback described above, such that the user is made aware that the needle pusher 116 has re-engaged the needle 112.

Once the needle pusher 116 has reengaged the needle 112, the operating handle 118 may be retracted in the direction X so as to disengage the needle 112 from the needle capturing assembly 110. And, when the operating handle 118 is in the fully retracted position, the needle pusher 116 and the needle 112 are in position to repeat the foregoing operation and create another stitch. However, if the user of the suturing device 1000 is unable to release the needle 112 from the needle capturing assembly 110 simply by retracting the operating handle 118 in the direction X, for example, in the event that the gripping force exerted by the needle pusher 116 on the needle 112 after the needle pusher 116 has reengaged the needle 112 is not sufficient to maintain engagement of the needle by the needle pusher 116 while the needle 112 is still captured by the needle capturing assembly 110, the user of the suturing device 1000 may employ an apparatus, such as a hemostat, forceps, needle holder, or the like, to release the needle 112 from the needle capturing assembly 110. Preferably, the needle 112 is released from the needle capturing assembly 110 while the end of the needle 112 remains engaged with the needle pusher 116 such that the as the needle 112 is moved in the direction X, the needle pusher 116 also moves in the direction X. Once the needle 112 is released from the needle capturing assembly 110, the apparatus should no longer be needed and both the needle pusher 116 and the needle 112 may be fully retracted by simply retracting the operating handle 118 in the direction X.

Various types of apparatus may be used by the user for extracting the needle 112 from the needle capturing assembly 110. For example, a needle holder with a first jaw and a second jaw may be used to extract the needle 112 from the needle capturing assembly 110. The first jaw and the second jaw of the needle holder may include, respectively, a first angled portion and a second angled portion. The first angled portion of the first jaw may be inclined at an angle with respect to a remaining portion of the first jaw. Similarly, the second angled portion of the second jaw may be inclined at an angle with respect to a remaining portion of the second jaw. The first angled portion and the second angled portion may include, respectively, a first tip of the first jaw and a second tip of the second jaw. The needle holder may be held by the user in a manner such that the first angled portion and the second angled portion rest on the first recessed portion 1014*a* and the second recessed portion 1014*b*, respectively, and the needle 112 is held between the first jaw and the second jaw. In other words, the needle 112 is gripped or clamped between the first jaw and the second jaw of the needle holder. When the needle 112 is clamped between the first jaw and the second jaw with sufficient clamping force, the needle holder may be moved in a direction X (away from the distal end 1002*b*) so that the first angled portion and the second angled portion move or slide with respect to the first recessed portion 1014*a* and the second recessed portion 1014*b*. In this manner, the needle 112 may be extracted from the needle capturing assembly 110.

Once the needle pusher 116 and the needle 112 are in position to repeat the foregoing operation and create another stitch, the user may reposition the suturing device 1000 within the subject's body and re-pass the needle 112 and the suture 120 through the tissue 103 previously sutured or pass the needle 112 and the suture 120 through another tissue. It should be appreciated that by repeating the foregoing procedure, the suturing device 1000 may be operated to make multiple passes of the needle 112 and the suture 120 through tissue 103 (or another tissue) and thereby make multiple stitches without having to utilize a second needle or suture.

It should be appreciated that relative dimensions and arrangement of the working channel 106, the first channel 1008*a*, the second channel 1008*b*, the third channel 1008*c*, the needle pusher 116 and the needle 112, as described above, ensure that the needle pusher 116 and the needle 112 remain axially aligned throughout the entire operation of the suturing device 1000.

FIG. 10D illustrates an enlarged view of the distal end 1002*b* of the suturing device 1000 when the operating handle 118 is in a partially advanced position, in accordance with an exemplary embodiment of the present disclosure. In FIG. 10D, the needle 112 is shown to pass over the cavity 1004.

FIG. 10E illustrates an enlarged view of the distal end 1002*b* of the suturing device 1000 when the operating handle 118 is in the fully advanced position, in accordance with an exemplary embodiment of the present disclosure. Further, the needle pusher 116 is shown to have passed through the first channel 1008*a*, and the needle 112 is shown to have passed through the second channel 1008*b* so as to be captured by the needle capturing assembly 110.

FIG. 10F illustrates an enlarged cross sectional side view of the distal end 1002*b* of the suturing device 1000 when the operating handle 118 is moved to the fully advanced position, in accordance with an exemplary embodiment of the present disclosure. In FIG. 10F, the needle pusher 116 is shown to have passed through the first channel 1008*a* and the needle 112 is shown to have been captured by the needle capturing assembly 110.

FIG. 10G illustrates an enlarged cross sectional side view of the distal end 1002*b* of the suturing device 1000, in accordance with an exemplary embodiment of the present disclosure. In FIG. 10G, the first channel 1008*a*, the second channel 1008*b*, and the third channel 1008*c* are shown.

Figure 10H:
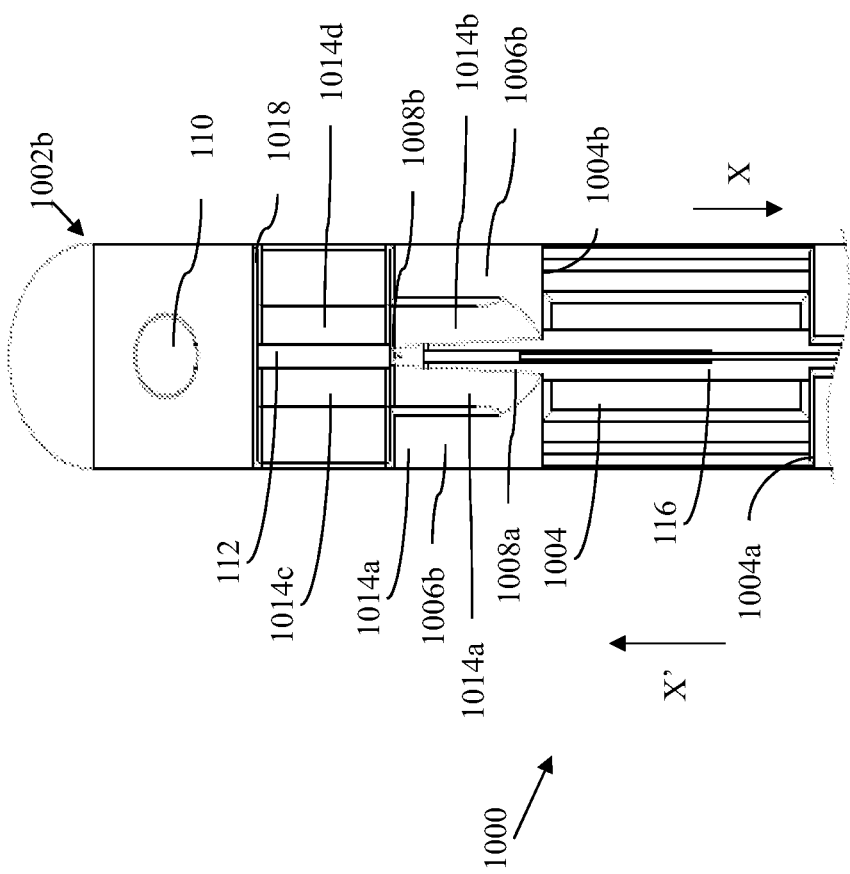
FIG. 10H illustrates an enlarged top view of the distal end of the suturing device when the operating handle is moved to the fully advanced position, in accordance with an exemplary embodiment of the present disclosure.

FIG. 10H illustrates an enlarged top view of the distal end 1002*b* of the suturing device 1000 when the operating handle 118 is moved to the fully advanced position, in accordance with an exemplary embodiment of the present disclosure. In FIG. 10H, the needle pusher 116 is shown to have passed through the first channel 1008*a* and the needle 112 is shown to have been captured by the needle capturing assembly 110.

Figure 10I:
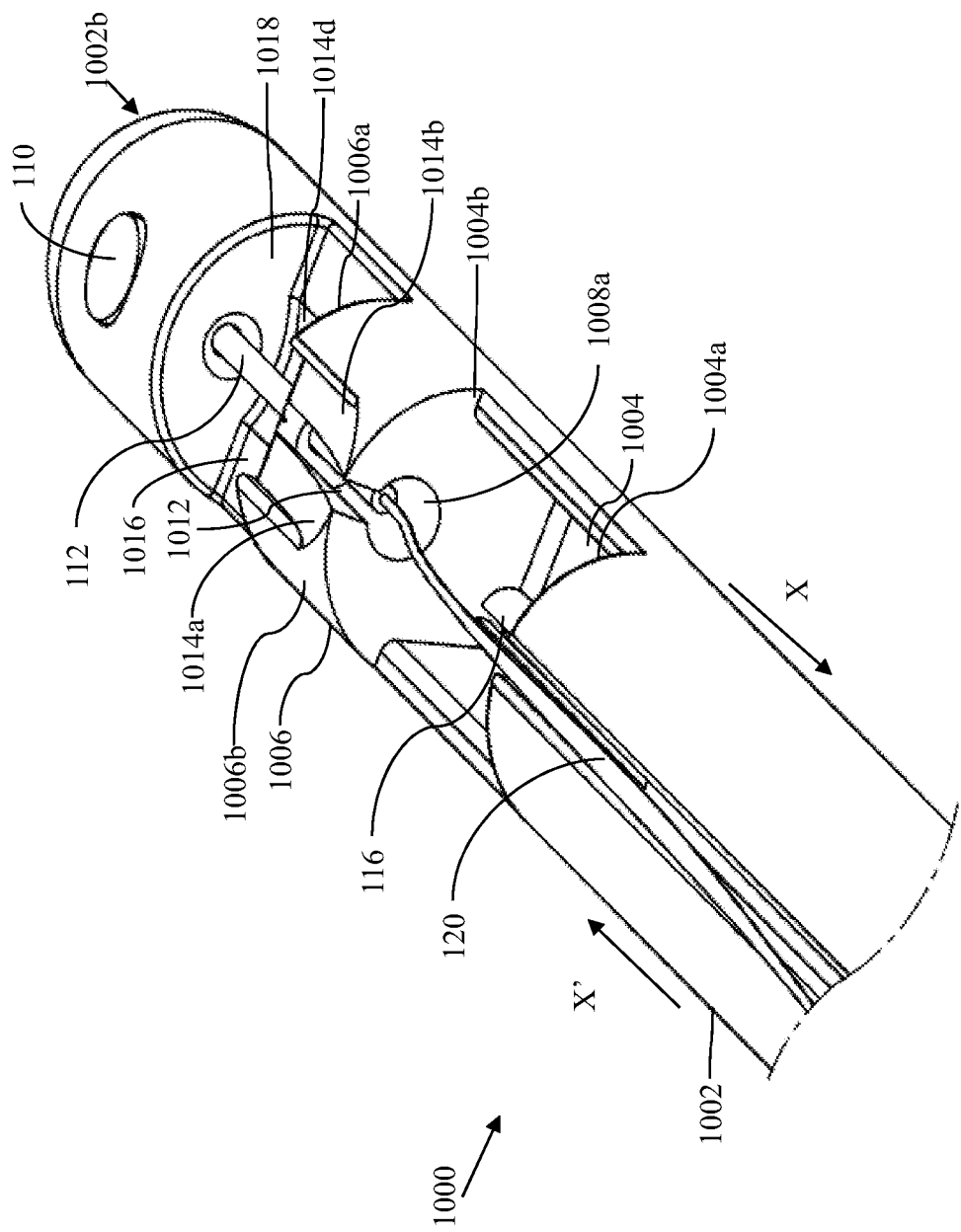
FIG. 10I illustrates an enlarged view of the distal end of the suturing device when the operating handle is moved from the fully advanced position to an intermediate position, in accordance with an embodiment of the disclosure.

FIG. 10I illustrates an enlarged view of the distal end 1002*b* of the suturing device 1000 when the operating handle 118 is moved from the fully advanced position to the intermediate position, in accordance with an exemplary embodiment of the present disclosure. In FIG. 10I, the needle 112 is shown to have been captured by the needle capturing assembly 110. Further, in FIG. 10I, the needle 112 is shown to have disengaged from the needle pusher 116 while a portion of the needle 112 extends into the first channel 1008*a*.

Figure 11A:
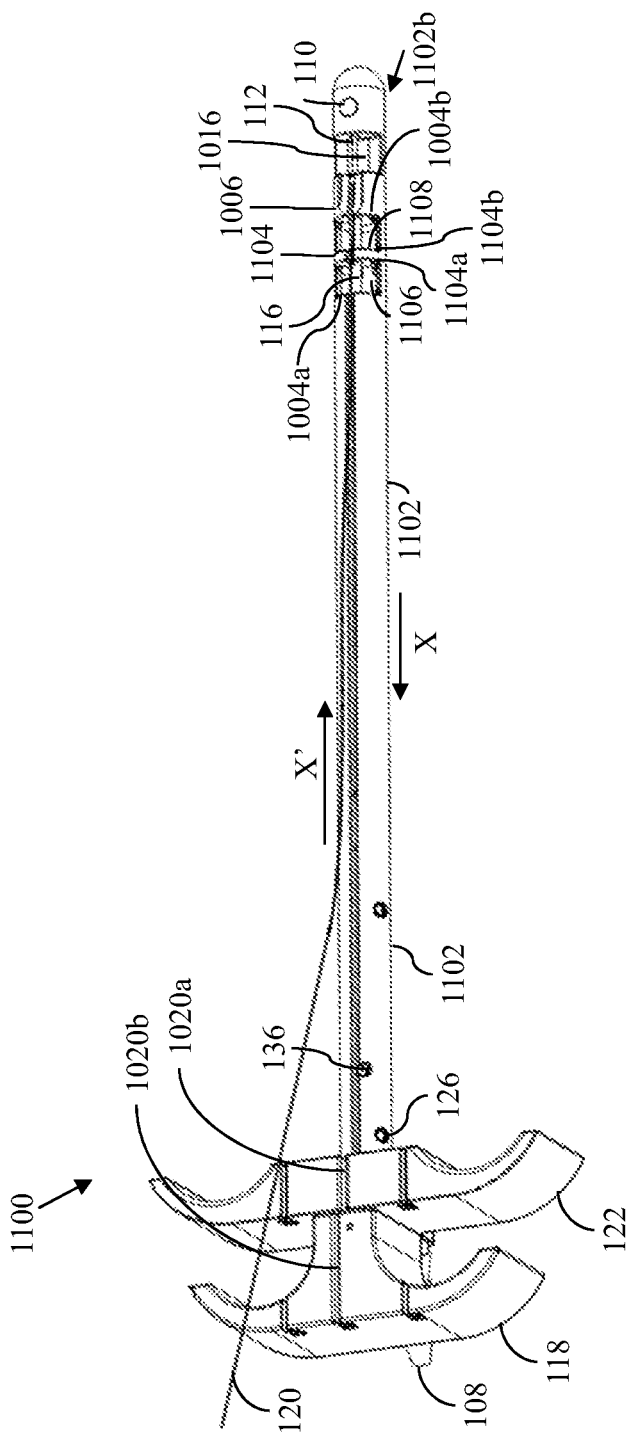
FIGS. 11A-11C illustrate a perspective view, an enlarged view, and a cross-sectional side view, respectively, of a suturing device, in accordance with an exemplary embodiment of the present disclosure.
Figure 11B:
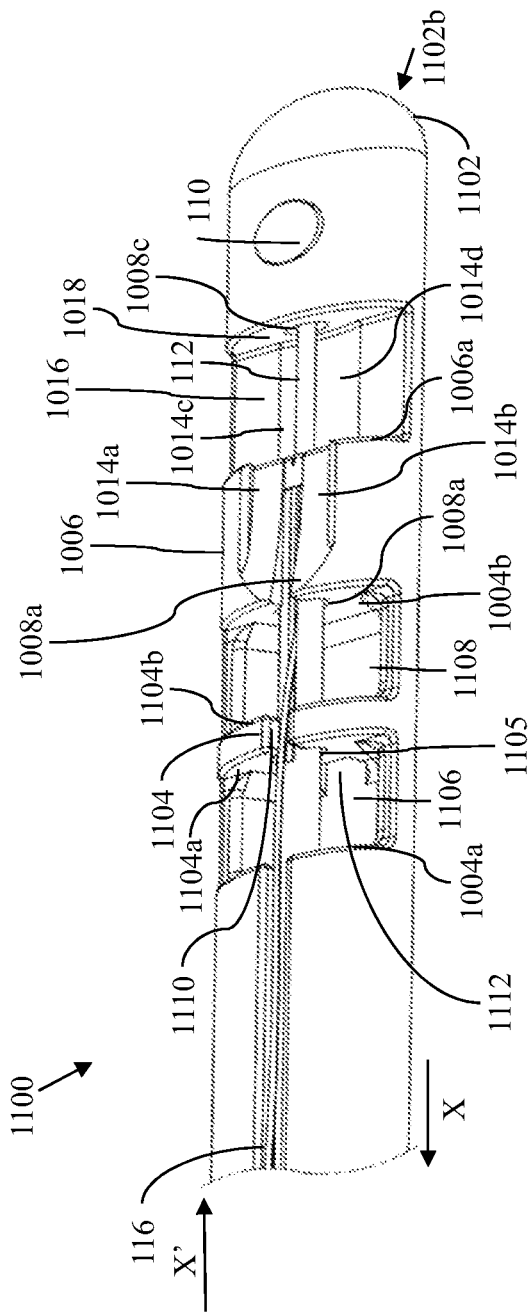
Figure 11C:
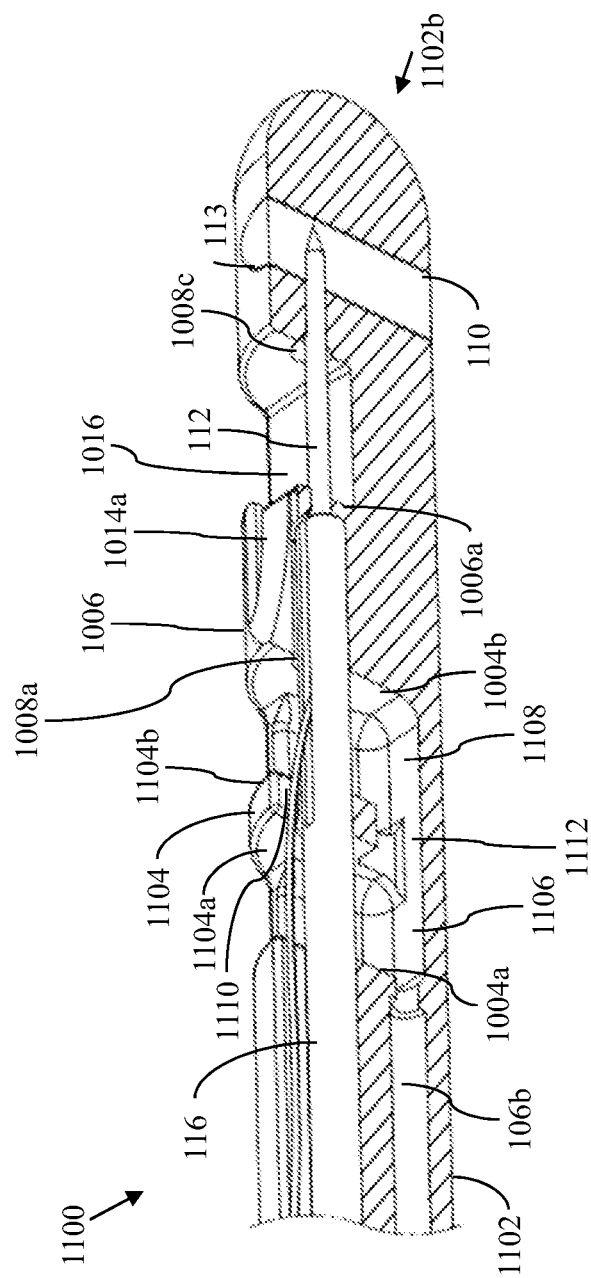

FIGS. 11A-11C illustrate a perspective view, an enlarged view, and a cross-sectional side view, respectively, of a suturing device 1100, in accordance with an exemplary embodiment of the present disclosure. The suturing device 1100 is structurally and functionally similar to the suturing device 1000. However, in contrast to the elongated member 1002 of the suturing device 1000, an elongated member 1102 of the suturing device 1100 additionally includes a dividing structure 1104 in the cavity 1004. The dividing structure 1104 divides the cavity 1004 into a first cavity portion 1106 and a second cavity portion 1108. Preferably, the dividing structure 1104 includes a fourth channel 1105 (shown in FIGS. 11B and 11D) that extends through the entirety of the dividing structure 1104 as shown.

The fourth channel 1105 is preferably dimensioned such that the needle pusher 116 can be moved axially through the fourth channel 1105 with minimal friction with walls of the fourth channel 1105 while maintaining a desired amount of concentric alignment with the fourth channel 1105, taking into account tolerances of materials used in the design of the suturing device 1100. Further, the fourth channel 1105 is preferably wider at a wall 1104a of the dividing structure 1104 than it is at a point where the fourth channel 1105 meets the wall 1104b of the dividing structure 1104. To accommodate this change in diameter, the fourth channel 1105, for a portion of its length proximate the wall 1104a, may be shaped in a form of a frustum of a cone as was the case with the embodiment of the first channel 1008a. Alternatively, the fourth channel 1105 may, for its entire length, be shaped in the form of a frustum of a cone as was the case with the embodiment of the first channel 1008a.

By increasing the diameter of the fourth channel 1105 at the wall 1104b as compared to the diameter of the fourth channel 1105 at the wall 1104b, one can minimize a chance that the distal tip of the needle pusher 116 (or the distal tip of the needle 112, when carried by the needle pusher 116), when being moved in the direction X', strikes the wall 1104a, and facilites the unobstructed movement of both the needle pusher 116 and the needle 112 through the fourth channel 1105 in the direction X'. Preferably, the fourth channel 1105 includes an opening 1110 (shown in FIGS. 11B-11D) that extends along its length to allow the suture 120 to exit the fourth channel 1105 as the needle pusher 116 and the needle 112 move through the fourth channel 1105.

Figure 11D:
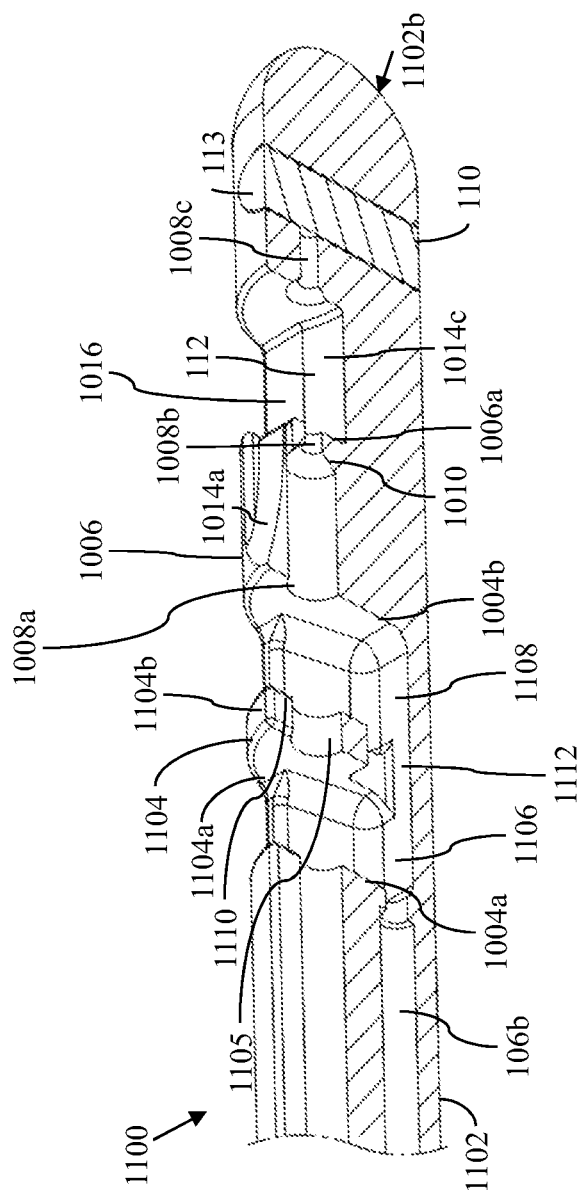
FIG. 11D illustrates an enlarged cross-sectional side view of a distal end of the suturing device, in accordance with an exemplary embodiment of the present disclosure.

In a non-limiting example, during operation of the suturing device 1100, a vacuum is always simultaneously applied to both the first cavity portion 1106 and the second cavity portion 1108. This may be accomplished, for example, by providing an opening 1112 at the base of dividing structure 1104 as shown in FIGS. 11B-11D. With this configuration, when a vacuum is applied to the first cavity portion 1106 via the suction channel 106b, it is also applied to the second cavity portion 1108 through the opening 1112. Alternatively, the first cavity portion 1106 and the second cavity portion 1108 may be independently connected to the suction channel 106b. In such a scenario, vacuum may be simultaneously applied at the first cavity portion 1106 and the second cavity portion 1108 when the blocking member 124 blocks the second aperture 136.

In another non-limiting example, during operation of the suturing device 1100, application of a vacuum to the first cavity portion 1106 and application of a vacuum to the second cavity portion 1108 may be independently controlled such that a vacuum may be applied to only one of the first cavity portion 1106 and the second cavity portion 1108 or a vacuum may be simultaneously applied to both the first cavity portion 1106 and the second cavity portion 1108. This may be accomplished, for example, by connecting the first cavity portion 1106 and the second cavity portion 1108 to separate, independently operated vacuum sources.

It should be appreciated that by providing the elongated member 1102 with the first cavity portion 1106 and the second cavity portion 1108, multiple (in this case, two) portions of contiguous portions of the tissue 103 may be suctioned into and captured by the first cavity portion 1106 and the second cavity portion 1108 such that a single pass of the needle pusher 116 and needle 112 (and, thereby, the suture 120) over the first cavity portion 1106 and the second cavity portion 1108 results in a suturing of both the first portion and the second portion of the tissue 103. Furthermore, additional (i.e., more than one) dividing structures may be provided in order to create additional (i.e., more than two) cavity portions. Also, the distances between cavity portions may be selected so as to ensure that the desired portions of the tissue 103 are suctioned into the cavities and sutured.

An operation of the suturing device 1100 may be substantially similar to the operation of the suturing device 1000 explained in the foregoing description of FIGS. 10A-10F. The operation of the suturing device 1100 is not explained to avoid a repetition of the foregoing descriptions of FIGS. 10A-10F.

FIG. 11D illustrates an enlarged cross-sectional side view of the distal end 1100b of the suturing device 1100, in accordance with an exemplary embodiment of the present disclosure. In FIG. 11D, the suction channel 106b, the first channel 1008a, the second channel 1008b, the third channel 1008c, and the fourth channel 1105 are shown. Further, in FIG. 11D, the first cavity portion 1106, the second cavity portion 1108, and the opening 1112 at the base of the dividing structure 1104 are shown.

Figure 12A:
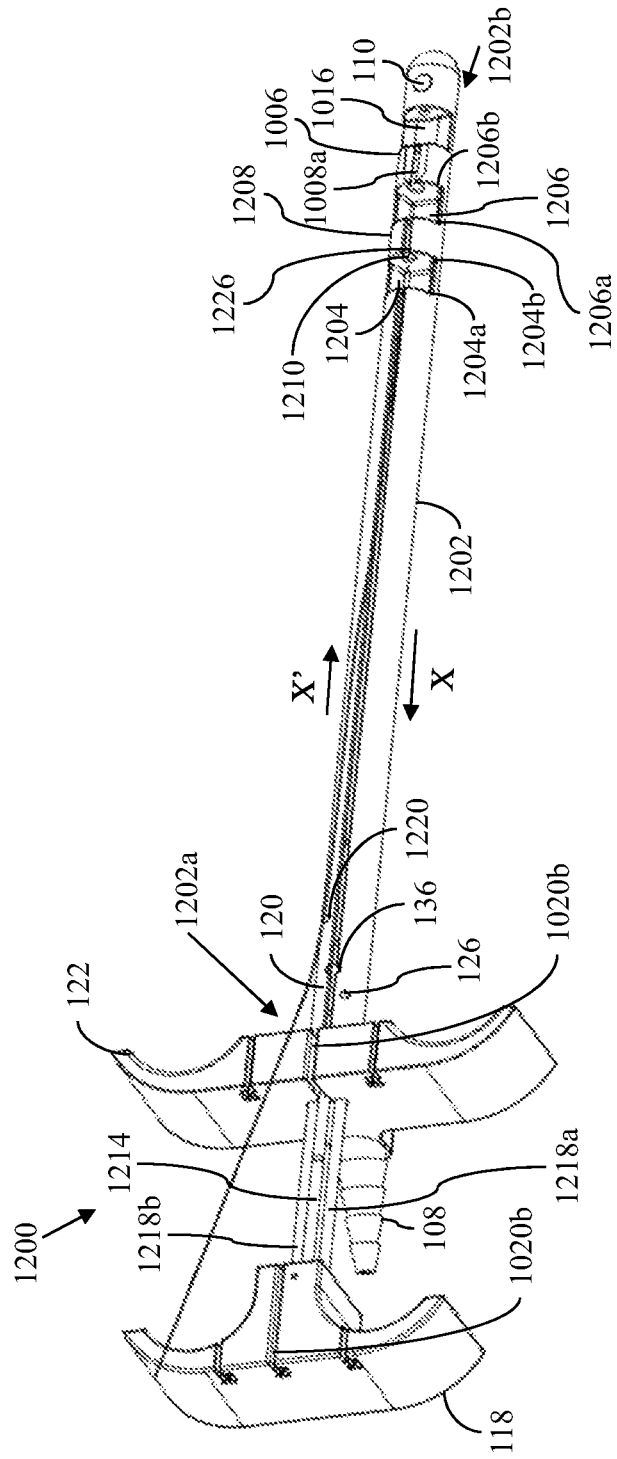
FIGS. 12A-12D illustrate a perspective side view, another perspective side view, an enlarged view, and a cross-sectional side view, respectively, of a suturing device, in accordance with an exemplary embodiment of the present disclosure.
Figure 12B:
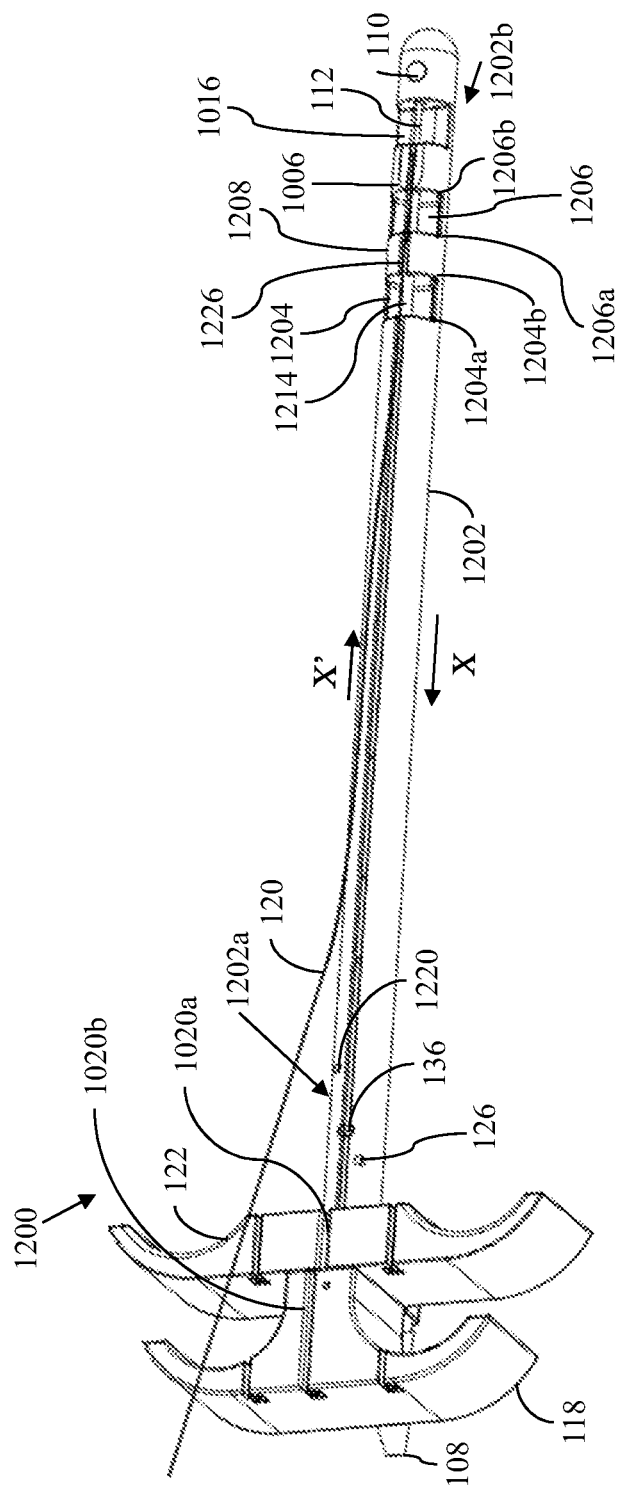
Figure 12C:
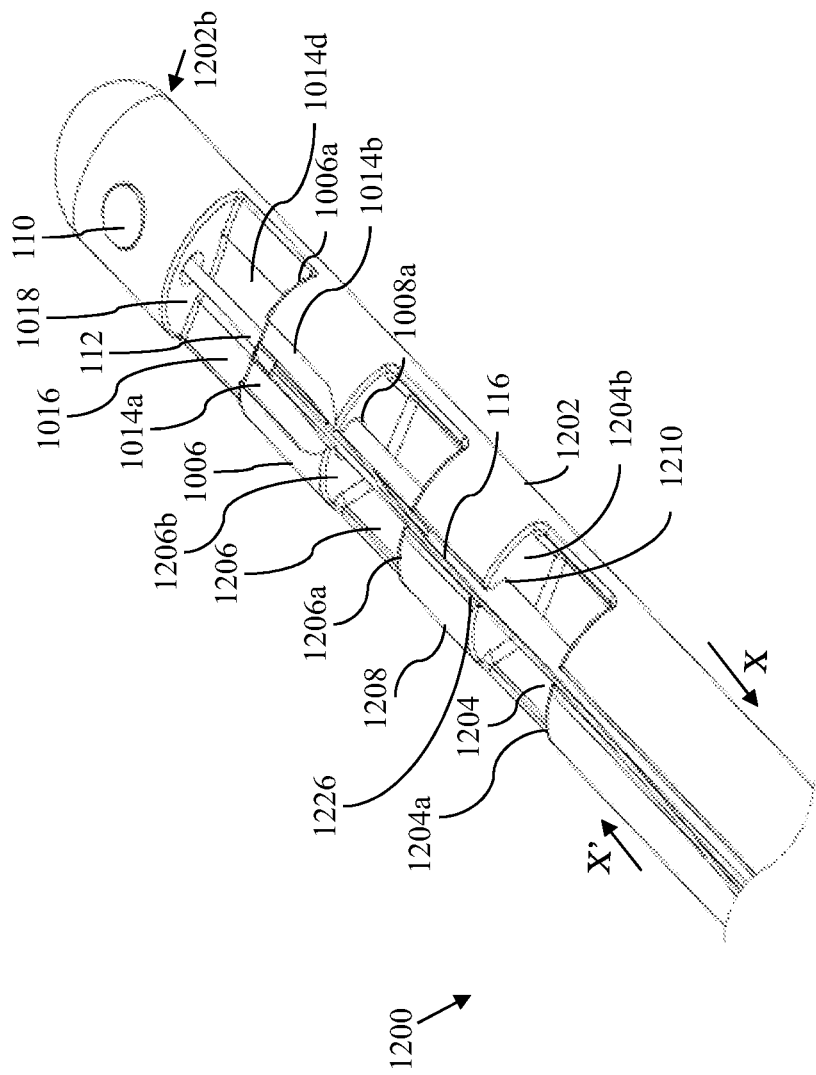
Figure 12D:
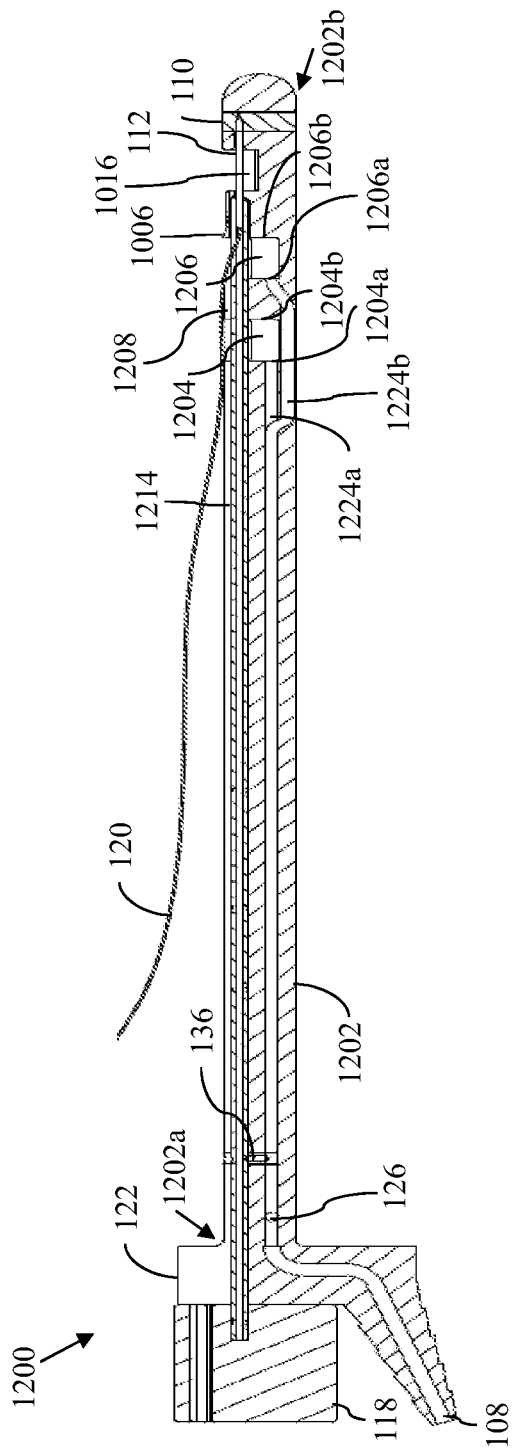

FIGS. 12A-12D illustrate a perspective side view, another perspective side view, an enlarged view, and a cross-sectional side view, respectively, of a suturing device 1200, in accordance with an exemplary embodiment of the present disclosure. As shown in FIG. 12A, the suturing device 1200 is structurally and functionally similar to the suturing device 1100 of FIGS. 11A-11C. Differences between the suturing device 1200 and the suturing device 1100 will be explained below. FIG. 12A illustrates the suturing device 1200 when the operating handle 118 is partially advanced. FIGS. 12C-12D illustrate the suturing device 1200 when the operating handle 118 is at the fully advanced position.

As shown in FIGS. 12A-12D, the suturing device 1200 includes an elongated member 1202 having a proximal end 1202a and a distal end 1202b ("proximal" and "distal" being from the perspective of a user of the suturing device 1200). Like the elongated member 1102 of the suturing device 1100, the elongated member 1202 of the suturing device 1200 includes a first cavity 1204 and a second cavity 1206 for capturing a first portion and a second portion, respectively, of the tissue 103 (e.g., portions of contiguous tissue) when a vacuum is applied to the first cavity 1204 and the second cavity 1206.

Preferably, the first cavity 1204 and the second cavity 1206, like the cavity 104 of the suturing device 100, are dimensioned to suit a particular application and to accommodate the type and amount of tissue that is to be captured. For example, the first cavity 1204 may include a fourth wall 1204a (i.e., a front wall of the first cavity 1204 from the perspective of the user of the suturing device 1200; shown in FIG. 12B) at a first end of the first cavity 1204 and a fifth wall 1204b (i.e., a rear wall from the perspective of the user of the suturing device 1200 shown in FIG. 12B) at a second end of the first cavity 1204 parallel and opposite to the fourth wall 1204*a*. The second cavity 1206 may include a sixth wall 1206*a* (i.e., a front wall of the second cavity 1206 from the perspective of the user of the suturing device 1200; shown in FIG. 12B) at a first end of the second cavity 1206 and a seventh wall 1206*b* (i.e., a rear wall from the perspective of the user of the suturing device 1200 shown in FIG. 12B) at a second end of the second cavity 1206 parallel and opposite to the sixth wall 1206*a*.

The elongated member 1202 further includes a dividing structure 1208 that separates the first cavity 1204 and the second cavity 1206. The dividing structure 1208 is formed in between (i.e., formed by the) the fifth wall 1204*b* and the sixth wall 1206*a*. In other words, the dividing structure 1208 extends from the fifth wall 1204*b* of the first cavity 1204 to the sixth wall 1206*a* of the second cavity 1206. Therefore, the fifth wall 1204*b* and the sixth wall 1206*a* form a first end surface and a second end surface of the dividing structure 1208, respectively. Preferably, the dividing structure 1208 includes a fifth channel 1210 (shown in FIGS. 12A, 12C, and 12E-12F) that extends through the entirety of the dividing structure 1208. The fifth channel 1210 is concentric (e.g., coaxial) with respect to the first channel 1008*a*, the second channel 1008*b*, and the third channel 1008*c*. A path defined by the fifth channel 1210 forms an extension of the working channel 106*a*.

In contrast to the needle pusher assembly 114 of the suturing device 1100, the suturing device 1200 includes a needle pusher assembly 1212. The needle pusher assembly 1212 is structurally and functionally similar to the needle pusher assembly 114 of the suturing device 1100. Differences between the needle pusher assembly 1212 of the suturing device 1200 and the needle pusher assembly 114 of the suturing device 1100 are explained below.

The needle pusher assembly 1212 (shown in FIG. 12G) includes the operating handle 118 and a needle pusher 1214. The needle pusher 1214 is structurally and functionally similar to the needle pusher 116 of the suturing device 100. Like the first through third detents 132*a*-132*c* included in the needle pusher 116 (shown in FIG. 1E) of the suturing device 100, the needle pusher 1214 preferably includes the first through fourth detents 1216*a*-1216*d*. The first through fourth detents 1216*a*-1216*d* of the suturing device 1200 are structurally and functionally similar to the first through third detents 132*a*-132*c* included in the needle pusher 116 of the suturing device 100. Significance of the first through fourth detents 1216*a*-1216*d* is explained below.

Figure 12E:
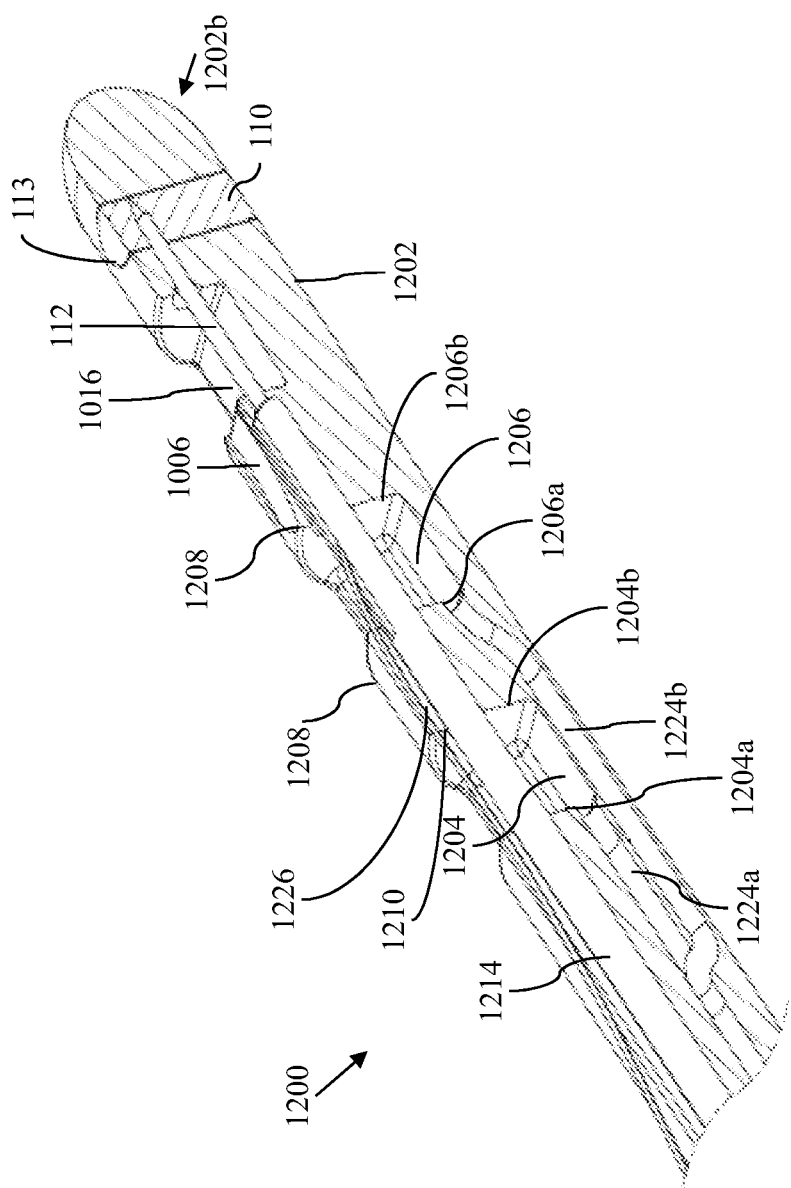
FIG. 12E illustrates an enlarged cross-sectional view of a distal end of the suturing device when an operating handle of the suturing device is moved to a fully advanced position, in accordance with an exemplary embodiment of the present disclosure.
Figure 12F:
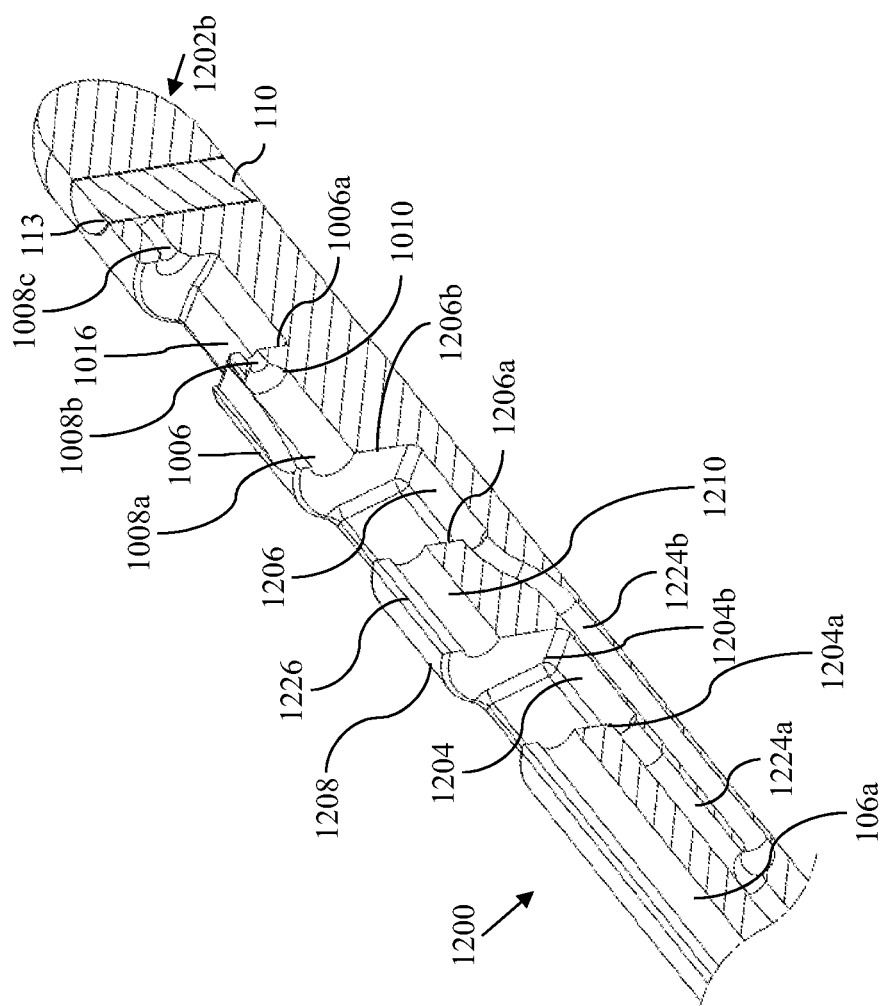
FIG. 12F illustrates an enlarged cross-sectional view of the distal end of the suturing device, in accordance with another exemplary embodiment of the present disclosure.
Figure 12G:
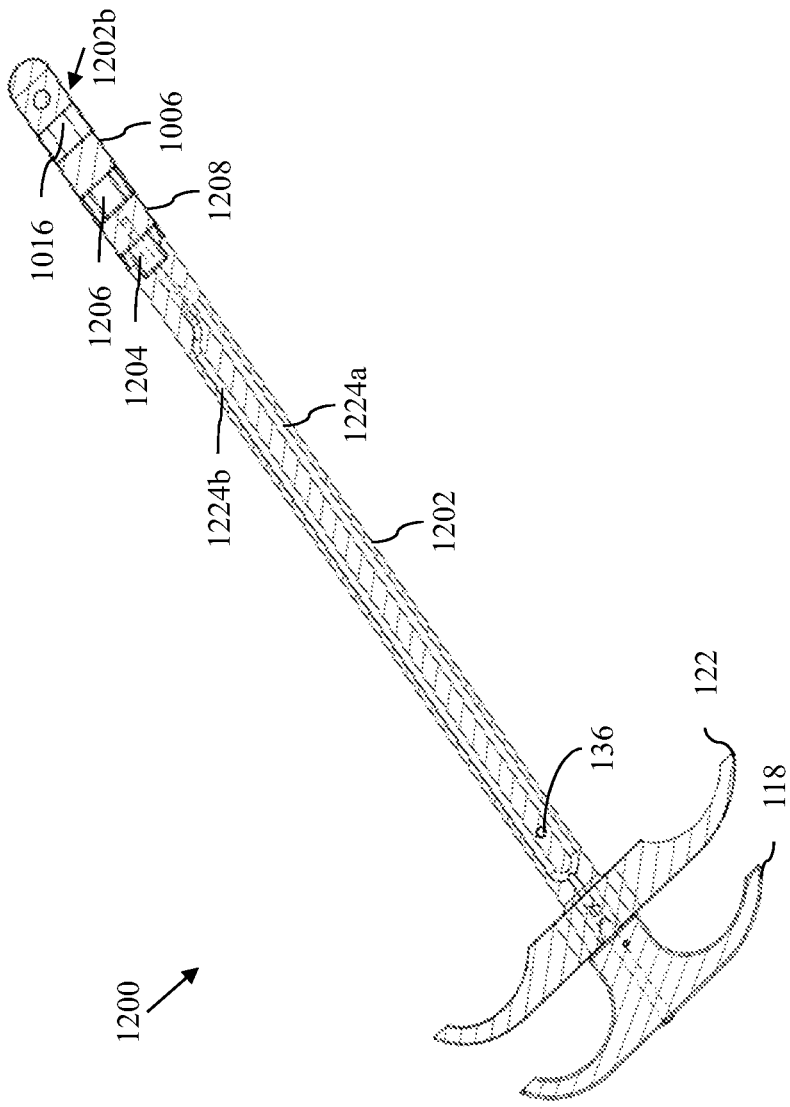
FIG. 12G illustrates a cross-sectional top view of the suturing device, in accordance with an exemplary embodiment of the present disclosure.
Figure 12H:
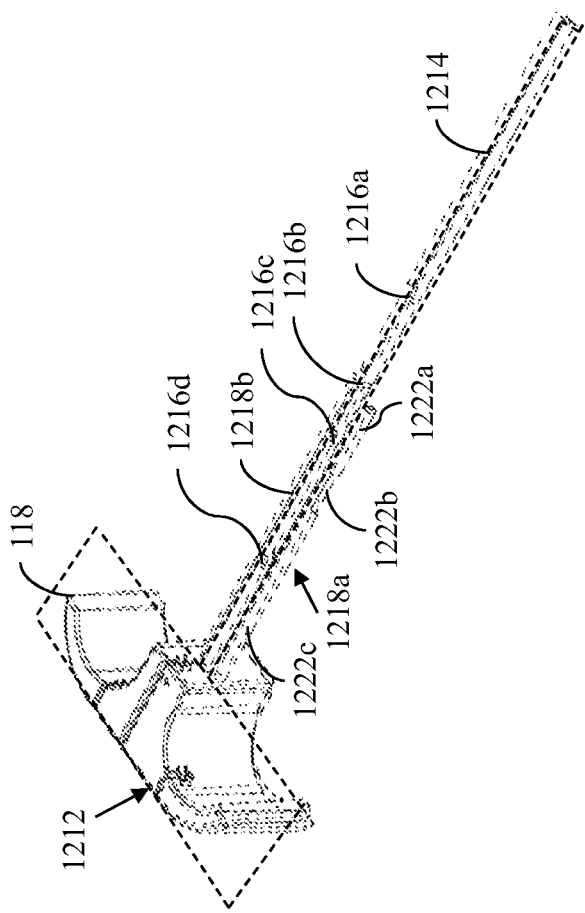
FIG. 12H illustrates a perspective view of a needle pusher assembly of the suturing device, in accordance with an exemplary embodiment of the present disclosure.

A first blocking member 1218*a* and a second blocking member 1218*b* are attached to the needle pusher assembly 1212 as shown in FIGS. 12A and 12H. The first blocking member 1218*a* and the second blocking member 1218*b* of the suturing device 1200 are structurally and functionally similar to the blocking member 124 of the suturing device 100 (shown in FIG. 1A). The first blocking member 1218*a* attached to the needle pusher assembly 1212, in combination with the first aperture 126 and the vacuum control channel 106*c* (hereinafter, designated and referred to as "the first vacuum control channel 106*c*") formed in the elongated member 1202, may be provided to control application of the vacuum to the first cavity 1204 just through normal operation of the suturing device 1200 without having to manually turn the vacuum source on and off. The first blocking member 1218*a* comprises an elongated member coupled to the operating handle 118 and arranged parallel and adjacent to the needle pusher 1214. The second blocking member 1218*b* attached to the needle pusher assembly 1212, in combination with a third aperture 1220 and a second vacuum control channel (not shown) formed in the elongated member 1202, may be provided to control application of the vacuum to the second cavity 1206 through normal operation of the suturing device 1200 without having to manually turn the vacuum source on and off.

The second blocking member 1218*b* comprises an elongated member coupled to the operating handle 118 and arranged parallel and adjacent to the needle pusher 1214. Preferably, the second blocking member 1218*b* and the first blocking member 1218*a* are placed on either side of the needle pusher 1214 (as shown in FIGS. 12A and 12B). In a non-limiting example, the third aperture 1220 that is included in the elongated member 1202 is offset in the direction X', with respect to the first aperture 126. In other words, the third aperture 1220 is located farther away from the proximal end 1202*a* in the X' direction with respect to the first aperture 126.

In one embodiment, the diameter of the first blocking member 1218*a* may vary across a length of the first blocking member 1218*a*. Preferably, the first blocking member 1218*a* includes a first portion 1222*a* with a first diameter, a second portion 1222*b* with a second diameter, and a third portion 1222*c* with the first diameter (as shown in FIG. 12H). The second portion 1222*b* of the first blocking member 1218*a* includes a step-down in diameter in comparison to the first portion 1222*a* and the third portion 1222*c* of the first blocking member 1218*a* (as shown in FIG. 12H). In other words, the second diameter of the second portion 1222*b* is less than the first diameter of the first portion 1222*a* and the second portion 1222*b* of the first blocking member 1218*a*. Preferably, a diameter of the second blocking member 1218*b* is consistent throughout a length of the second blocking member 1218*b*.

The elongated member 1202 is provided with a first suction channel 1224*a* and a second suction channel 1224*b* (as shown in FIGS. 12D-12G). The first suction channel 1224*a* and the second suction channel 1224*b* are structurally and functionally similar to the suction channel 106*b* of the suturing device 1000 (shown in FIG. 11C). A first end of the first suction channel 1224*a* has the vacuum port 108 that may be coupled to the vacuum source (not shown). A second end of the first suction channel 1224*a* is coupled to the first cavity 1204 such that the first cavity 1204, the first suction channel 1224*a*, and the vacuum source are in fluidic communication. A first end of the second suction channel 1224*b* has the vacuum port 108 that may be coupled to the vacuum source (not shown). A second end of the second suction channel 1224*b* is coupled to the second cavity 1206 such that the second cavity 1206, the second suction channel 1224*b*, and the vacuum source are in fluidic communication.

Preferably, the fifth channel 1210 includes an opening 1226 (shown in FIGS. 12B, 12C, 12E, and 12F) that extends along a length of the fifth channel 1210 to allow the suture 120 to exit the fifth channel 1210 as the needle pusher 1214 and the needle 112 move through the fifth channel 1210.

The fifth channel 1210 is preferably dimensioned such that the needle pusher 1214 and the needle 112 can be moved axially through the fifth channel 1210 with minimal friction with walls of the fifth channel 1210 while maintaining a desired amount of concentric alignment with the fifth channel 1210, taking into account tolerances of materials used in the design of the suturing device 1200. Further, the fifth channel 1210 is preferably wider at the fifth wall 1204*b* than it is at a point where the fifth channel 1210 meets the sixth wall 1206*a*. To accommodate this change in the diameter of the fifth channel 1210, the fifth channel 1210 may, for part of its length proximate the fifth wall 1204*b*, be shaped in a form of a frustum of a cone as was the case with the embodiment of the first channel 1008a. Alternatively, the fifth channel 1210 may, for its entire length, be shaped in the form of a frustum of a cone as was the case with the embodiment of the first channel 1008a. By increasing the diameter of the fifth channel 1210, one can minimize the chance that a distal tip of the needle pusher 1214 (or the distal tip of the needle 112, when carried by the needle pusher 1214), when being moved in the direction X', strikes the seventh wall 1206b and facilities the unobstructed movement of both the needle pusher 1214 and the needle 112 through the fifth channel 1210 in the direction X'.

During the operation of the suturing device 1200, advancement or retraction of the operating handle 118 translates to a corresponding movement of the first blocking member 1218a through the first vacuum control channel 106c and a corresponding movement of the second blocking member 1218b through the second vacuum control channel (not shown) included in the elongated member 1202. The length of the second vacuum control channel is preferably shorter than the length of the working channel 106a. Such movement of the first blocking member 1218a within the first vacuum control channel 106c, in turn, opens or blocks the first aperture 126. Similarly, such movement of the second blocking member 1218b within the second vacuum control channel, in turn, opens or blocks the third aperture 1220. Because the first aperture 126 is in fluidic communication with the first vacuum control channel 106c, which is further in fluidic communication with the first suction channel 1224a, opening of the first aperture 126 releases any vacuum pressure created within the first cavity 1204. Similarly, blocking the first aperture 126 maintains any vacuum pressure created within the first cavity 1204. Similarly, since the third aperture 1220 is in fluidic communication with the second vacuum control channel, which is further in fluidic communication with the second suction channel 1224b, opening of the third aperture 1220 releases any vacuum pressure created within the second cavity 1206. Blocking the third aperture 1220 maintains any vacuum pressure created within the second cavity 1206.

Advancing the operating handle 118 (from the fully retracted position) results in advancement of the first blocking member 1218a such that the first portion 1222a of the first blocking member 1218a blocks the first aperture 126, thereby maintaining a vacuum at the first cavity 1204 such that the first portion of the tissue 103 may be captured. Preferably, the first blocking member 1218a and the second blocking member 1218b are dimensioned in a manner that when the first portion 1222a of the first blocking member 1218a blocks the first aperture 126, the third aperture 1220 is not yet blocked by the second blocking member 1218b. In other words, when the operating handle 118 is partially advanced in the direction X' and the first portion 1222a of the first blocking member 1218a has blocked the first aperture 126, the second blocking member 1218b has not yet reached or blocked the third aperture 1220 that is offset in the direction X' with respect to the first aperture 126. In such a scenario, it will be appreciated that vacuum is created or maintained at the first cavity 1204, suctioning the first portion of the tissue into the first cavity 1204. However, vacuum is not yet created at the second cavity 1206. Preferably, when the operating handle 118 is advanced further in the direction X' towards the fixed handle 122, the second portion 1222b of the first blocking member 1218a reaches the first aperture 126 and the second blocking member 1218b reaches the third aperture 1220 and blocks the third aperture 1220.

It will be appreciated that since the second diameter of the second portion 1222b of the first blocking member 1218a is less than the first diameter of the first portion 1222a of the first blocking member 1218a, the second portion 1222b does not block the first aperture 126, resulting in a release of the vacuum created in the first cavity 1204. The second blocking member 1218b blocks the third aperture 1220, creating a vacuum at the second cavity 1206, causing the second portion of the tissue to be suctioned into the second cavity 1206. Further advancement of the operating handle 118 in the direction X' will result in corresponding advancement of the first blocking member 1218a and the second blocking member 1218b (and the needle pusher 1214). Based on further advancement of the operating handle 118 in the direction X', an entirety of the second portion 1222b of the first blocking member 1218a may advance past the first aperture 126, and the third portion 1222c with the first diameter may reach and block the first aperture 126. This may cause generation of vacuum in the first cavity 1204, and the first portion of the tissue 103 may be captured (i.e., recaptured) or suctioned into the first cavity 1204. It will be appreciated that the third aperture 1220 remains blocked by the second blocking member 1218b, and, therefore, the vacuum at the second cavity 1206 is maintained. It will be appreciated that any further advancement of the operating handle 118 towards the fully advanced position will result in continual blocking of the first aperture 126 and the third aperture 1220 by the third portion 1222c of the first blocking member 1218a and the second blocking member 1218b, respectively. Therefore, the vacuum at the first cavity 1204 and the second cavity 1206 is maintained.

It should be appreciated that provision of the first blocking member 1218a, the second blocking member 1218b, the first aperture 126, the third aperture 1220, the first vacuum control channel 106c, the second vacuum control channel, the first suction channel 1224a, and the second suction channel 1224b avoids the need to manually turn the vacuum source on/off. It also enables synchronization of the application of the vacuum to the first cavity 1204 and the second cavity 1206 with the passage of the needle 112 and the suture 120 through the first portion and the second portion of the tissue during normal operation of the suturing device 1200. As an alternative to the first blocking member 1218a and the second blocking member 1218b, the user of the suturing device 1200 may manually cover/uncover the first aperture 126 and/or the third aperture 1220, for example, with his/her finger, to control the application of the vacuum to the first cavity 1204 and/or the second cavity 1206. However, in that situation, the user must be aware of the timing of covering/uncovering the first aperture 126 and/or the third aperture 1220 such that application of the vacuum to the first cavity 1204 and/or the second cavity 1206 is properly synchronized with the movement of the needle 112 and the suture 120.

Like the suturing device 100 of FIGS. 1A and 1F, the suturing device 1200 may include the ball-spring detent mechanism 130. However, in contrast to the suturing device 100, the suturing device 1200 may include the first through fourth detents 1216a-126d. As described in the foregoing, the first through fourth detents 1216a-126d of the suturing device 1200 are structurally and functionally similar to the first through third detents 132a-132c of the suturing device 100. In order to prepare the suturing device 1200 for use, the needle pusher 1214 (with the needle 112 and the suture 120 engaged) is inserted into the proximal end 1202a of the elongated member 1202 and pushed towards the fixed handle 122 until the first detent 1216a aligns with the second aperture 136, causing the ball 138b to engage with the first detent 1216*a*. When the ball 138*b* is engaged with the first detent 1216*a*, the ball-spring detent mechanism 130 generates a first audible click sound and holds the needle pusher 1214 in position. Preferably, the first audible click and/or tactile feedback caused by the engagement of the ball 138*b* with the first detent 1216*a* indicates that the needle pusher 1214 is in the fully retracted position and that the suturing device 1200 is ready for use. Moreover, because the first blocking member 1218*a* does not block the first aperture 126 when the needle pusher 1214 is in a fully retracted position, the first audible click and/or the tactile feedback caused by the engagement of the ball 138*b* with the first detent 1216*a* also indicate that no vacuum is being applied to the first cavity 1204 or the second cavity 1206.

Upon application of a requisite force to the operating handle 118 pushing it towards the fixed handle 122, the ball 138*b* is disengaged from the first detent 1216*a* and pushed back into the bore 134 towards the spring 138*a*. If the user continues to push on the operating handle 118, the needle pusher 1214 continues to advance through the working channel 106*a* until the second detent 1216*b* aligns with the second aperture 136 and engages with the ball 138*b* generating a second audible click sound and holding the needle pusher 1214 in an intermediate position. The second audible click and/or a tactile feedback caused by the engagement of the ball 138*b* with the second detent 1216*b* indicates that the needle pusher 1214 is in a first intermediate position and that needle 112 is in a preparatory position to be passed through the first portion of the tissue 103. Moreover, because the first portion 1222*a* of the first blocking member 1218*a* blocks the first aperture 126 when the needle pusher 1214 is in the first intermediate position, the second audible click and/or the tactile feedback caused by the engagement of the ball 138*b* with the second detent 1216*b* also indicates that the vacuum is being applied to the first cavity 1204 (via the first suction channel 1224*a*).

When the operating handle 118 is further advanced by the user in the direction X' to a second intermediate position, the third detent 1216*c* eventually becomes aligned with the second aperture 136 and engaged with the ball 138*b*, generating a third audible click sound and holding the needle pusher 1214 in position. The third audible click and/or the tactile feedback caused by the engagement of the ball 138*b* with the third detent 1216*c* indicates that the first portion 1222*a* of the first blocking member 1218*a* has advanced past the first aperture 126 and that the second portion 1222*b* of the first blocking member 1218*a* has reached the first aperture 126, thereby, releasing the vacuum at the first cavity 1204. Further, the third audible click and/or the tactile feedback caused by the engagement of the ball 138*b* with the third detent 1216*c* indicates that the second blocking member 1218*b* is blocking the third aperture 1220 and that vacuum is created at the second cavity 1206. Further, the third audible click and/or the tactile feedback caused by the engagement of the ball 138*b* with the third detent 1216*c* indicates that the needle pusher 1214 has advanced past the fifth wall 1204*b* of the first cavity 1204.

When the operating handle 118 is further advanced by the user to the fully advanced position, the fourth detent 1216*d* eventually becomes aligned with the second aperture 136 and engaged with the ball 138*b*, generating a fourth audible click sound and holding the needle pusher 1214 in position. The fourth audible click and/or the tactile feedback caused by the engagement of the ball 138*b* with the fourth detent 1216*d* indicate that the needle pusher 116 is in the fully advanced position, i.e., that the needle pusher 1214 has advanced past the seventh wall 1206*b* of the second cavity 1206 towards the distal end 1202*b* such that the entirety of the needle 112 has passed through the first portion and the second portion of the tissue, the suture 120 has passed through first portion and the second portion of the tissue, and the needle 112 has been captured by the needle capturing assembly 110.

An operation of the suturing device 1200 may be substantially similar to the operation of the suturing device 1000 explained in the foregoing description of FIGS. 10A-10F. The operation of the suturing device 1200 is not explained to avoid a repetition of the foregoing descriptions of FIGS. 10A-10F.

FIG. 12E illustrates an enlarged cross-sectional view of the distal end 1202*b* of the suturing device 1200 when the operating handle 118 is moved to the fully advanced position, in accordance with an exemplary embodiment of the present disclosure. In FIG. 12E, the first cavity 1204, the second cavity 1206, the dividing structure 1208, the first suction channel 1224*a*, and the second suction channel 1224*b*, the needle pusher 1214, and the needle 112 are shown.

FIG. 12F illustrates an enlarged cross-sectional view of the distal end 1202*b* of the suturing device 1200, in accordance with another exemplary embodiment of the present disclosure. In FIG. 12F, the first cavity 1204, the second cavity 1206, the dividing structure 1208, the fifth channel 1210, the first suction channel 1224*a*, and the second suction channel 1224*b* are shown. The needle pusher 1214, the needle 112, and the suture 120 are not shown in FIG. 12F in order to clearly illustrate the first channel 1008*a*, the second channel 1008*b*, the third channel 1008*c*, and the fifth channel 1210.

FIG. 12G illustrates a cross-sectional top view of the suturing device 1200, in accordance with an exemplary embodiment of the present disclosure. In FIG. 12G, the first suction channel 1224*a* and the second suction channel 1224*b* are shown.

FIG. 12H illustrates a perspective view of the needle pusher assembly 1212 of the suturing device 1200, in accordance with an exemplary embodiment of the present disclosure. In FIG. 12H, shown are the operating handle 118 and the needle pusher 1214 that includes the first through fourth detents 1216*a*-1216*d*. In FIG. 12H, also shown are the second blocking member 1218*b* and the first blocking member 1218*a* that includes the first portion 1222*a*, the second portion 1222*b*, and the third portion 1222*c*.

It should be appreciated that by providing the elongated member 1202 with the first cavity 1204 and the second cavity 1206, multiple (in this case, two) portions of contiguous portions of the tissue 103 may be suctioned into and captured by the first cavity 1204 and the second cavity 1206 such that a single pass of the needle pusher 1214 and needle 112 (and, thereby, the suture 120) over the first cavity 1204 and the second cavity 1206 results in a suturing of both the first portion and the second portion of the tissue 103. Furthermore, additional (i.e., more than one) dividing structures may be provided in order to create additional (i.e., more than two) cavities. Also, the distances between cavities may be selected so as to ensure that the desired portions of the tissue 103 are suctioned into the cavities and sutured.

In another embodiment, a vacuum applied to each of the first cavity 1204 and the second cavity 1206 may be individually controlled. In other words, the vacuum applied to each of the first cavity 1204 and the second cavity 1206 may be switched on or off individually. The suturing device 1200 to facilitate such a scenario may include a separate vacuum port for each suction channel (e.g., the first suction channel 1224a and the second suction channel 1224b). Therefore, the first suction channel 1224a and the second suction channel 1224b may each have a different vacuum port (not shown). Preferably, at least one of the first blocking member 1218a and the second blocking member 1218b may be adjustable in length. Preferably, a length of the first blocking member 1218a and the second blocking member 1218b may be adjusted before the needle pusher assembly 1212 is inserted in the proximal end 1202a of the suturing device 1200. Further, the third aperture 1220 may not be offset with respect to the first aperture 126 in the direction X'. In other words, the first aperture 126 and the third aperture 1220 may be equidistant from the proximal end 1202a of the elongated member 1202. Based on the length of the first blocking member 1218a and the length of the second blocking member 1218b, the user of the suturing device 1200 may control or select an order in which vacuum is applied to the first cavity 1204 and the second cavity 1206. For example, if the length of the first blocking member 1218a is greater than the length of the second blocking member 1218b, when the operating handle 118 is advanced from the fully retracted position, the first blocking member 1218a may block the first aperture 126 before the second blocking member 1218b blocks the third aperture 1220. Therefore, vacuum is applied to the first cavity 1204 and no vacuum is applied to the second cavity 1206 unless the operating handle 118 is advanced further and the second blocking member 1218b blocks the third aperture 1220. Similarly, if the length of the first blocking member 1218a is less than the length of the second blocking member 1218b, when the operating handle 118 is advanced from the fully retracted position, the second blocking member 1218b may block the third aperture 1220 before the first blocking member 1218a blocks the first aperture 126. Therefore, vacuum is applied to the second cavity 1206 and no vacuum is applied to the first cavity 1204 unless the operating handle 118 is advanced further and the first blocking member 1218a blocks the first aperture 126.

Similarly, if the length of the first blocking member 1218a is equal to the length of the second blocking member 1218b, when the operating handle 118 is advanced from the fully retracted position, the first blocking member 1218a and the second blocking member 1218b may simultaneously block the first aperture 126 and the third aperture 1220, respectively. Therefore, vacuum is applied to the first cavity 1204 and the second cavity 1206 simultaneously.

It should be appreciated that the embodiments disclosed herein allow for easy retraction of the needle 112 from the needle capturing assembly 110 and re-engagement of the needle 112 with the needle pusher 116 following each pass of the needle 112 through the tissue 103. This translates into more seamless administration of multiple stiches, enhancing speed and convenience of medical personnel conducting medical procedures (e.g., cosmetic surgery, bariatric surgery, orthopedic, general surgical, gynecologic, urologic, or the like). The embodiments disclosed herein also allow existing suturing devices to be optimized for multiple suturing at minimal cost. Thus, the disclosure also allows for easy enhancement of existing suturing devices, in addition to offering an improved design for manufacturing of new suturing devices.

While various exemplary embodiments of the disclosed suturing devices, apparatus, and clamps have been described above it should be understood that they have been presented for purposes of example only, not limitations. It is not exhaustive and does not limit the disclosure to the precise form disclosed. Modifications and variations are possible in view of the above teachings or may be acquired from practicing of the disclosure, without departing from the breadth or scope of the present disclosure.

In the claims, the words 'comprising', 'including' and 'having' do not exclude the presence of other elements or steps then those listed in a claim. The terms "a" or "an," as used herein, are defined as one or more than one. Unless stated otherwise, terms such as "first" and "second" are used to arbitrarily distinguish between the elements such terms describe. Thus, these terms are not necessarily intended to indicate temporal or other prioritization of such elements. The fact that certain measures are recited in mutually different claims does not indicate that a combination of these measures cannot be used to advantage.

While various embodiments of the present disclosure have been illustrated and described, it will be clear that the present disclosure is not limited to these embodiments only. Numerous modifications, changes, variations, substitutions, and equivalents will be apparent to those skilled in the art, without departing from the spirit and scope of the present disclosure. For example, one or more features of each of the various embodiments described herein may be used with the other embodiments to provide the benefits of those features to the other embodiments.

What is claimed is:

1. A suturing device comprising:
    an elongated member dimensioned for insertion into a body including tissue, the elongated member including a first end and a second end opposite the first end, a cavity formed in a surface of the elongated member, a needle passage, and a vacuum port, wherein the cavity includes a first end and a second end opposite the first end of the cavity and wherein when the elongated member is inserted into the body and a vacuum is applied to the cavity by a vacuum source through the vacuum port, the tissue is captured by the cavity;
    a needle capturing assembly disposed between the second end of the cavity and the second end of the elongated member;
    a needle pusher including a first end for engaging a needle, wherein when the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly; and
    a clamp,
    wherein the elongated member includes a first recess and a second recess, each of the first recess and the second recess extending longitudinally along a peripheral surface of the elongated member,
    wherein the clamp includes a first protuberance configured to slideably engage the first recess of the elongated member and a second protuberance configured to slideably engage the second recess of the elongated member, and
    wherein when the first protuberance is slideably engaged with the first recess of the elongated member and the second protuberance is slideably engaged with the second recess of the elongated member, the clamp is slideably coupled to the elongated member such that the clamp is moveable in the second direction from a first position to a second position.

2. The suturing device of claim 1, wherein the clamp is further moveable in the first direction from the second position to the first position while coupled to the elongated member.

3. The suturing device of claim 1, wherein when the clamp is in the first position with respect to the elongated member, the clamp is positioned to clamp a second end of the needle, and wherein when the clamp is in the second position with respect to the elongated member, the clamp is positioned to reposition the needle to be engaged by the first end of the needle pusher.

4. The suturing device of claim 1, wherein at least a portion of the elongated member forming a bottom surface of the cavity comprises a light transmissive material and wherein the suturing device further comprises a light source configured such that light from the light source is directed through the bottom surface of the cavity towards an open side of the cavity.

5. A suturing device comprising:
- an elongated member dimensioned for insertion into a body including tissue, the elongated member including a first end and a second end opposite the first end, a cavity formed in a surface of the elongated member, a needle passage, and a vacuum port, wherein the cavity includes a first end and a second end opposite the first end of the cavity and wherein when the elongated member is inserted into the body and a vacuum is applied to the cavity by a vacuum source through the vacuum port, the tissue is captured by the cavity;
- a needle capturing assembly disposed between the second end of the cavity and the second end of the elongated member;
- a needle pusher including a first end for engaging a needle, wherein when the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly;
- a base dimensioned to fit within the cavity; and
- a clamp coupled to the base and to the elongated member and moveable in the second direction such that when the clamp clamps a second end of the needle and is moved in the second direction, the first end of the needle is extracted from the needle capturing assembly and the needle is repositioned to be engaged by the first end of the needle pusher.

6. The suturing device of claim 5, wherein the clamp includes first and second levers, wherein at least one of the first and second levers is pivotally mounted to the base.

7. The suturing device of claim 6, wherein each of the first and second levers comprises a handle portion and a jaw portion.

8. The suturing device of claim 7, wherein at least the jaw portion of the second lever has a profile that facilitates clamping of the needle between the first and second levers.

9. An apparatus for use with a suturing device, the suturing device including an elongated member dimensioned for insertion into a body including tissue, the elongated member including a first end and a second end opposite the first end, a cavity formed in a surface thereof, a needle passage, and a vacuum port, wherein the cavity includes a first end and a second end opposite the first end of the cavity and wherein when the elongated member is inserted into the body and a vacuum is applied to the cavity by a vacuum source through the vacuum port the tissue is captured by the cavity, a needle capturing assembly disposed between the second end of the cavity and the second end of the elongated member, and a needle pusher including a first end for engaging a needle, wherein when the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly, the apparatus comprising:
- a base dimensioned to fit within the cavity; and
- a clamp coupled to the base so as to be moveable in the second direction with respect to the base, wherein the clamp is operable to clamp a second end of the needle opposite the first end of the needle and wherein when the clamp clamps the second end of the needle when the first end of the needle is captured by the needle capturing assembly and the clamp is moved in the second direction, the first end of the needle is extracted from the needle capturing assembly and the needle is repositioned to be engaged by the first end of the needle pusher.

10. The apparatus of claim 9, wherein the clamp includes first and second levers, wherein at least one of the first and second levers is pivotally mounted to the base.

11. The apparatus of claim 10, wherein each of the first and second levers comprises a handle portion and a jaw portion.

12. The apparatus of claim 11, wherein at least the jaw portion of the second lever has a profile that facilitates clamping of the needle between the first and second levers.

13. The apparatus of claim 9, wherein the clamp is coupled to the base so as to be further moveable in the first direction with respect to the base.

14. The apparatus of claim 9, wherein, when the clamp is in a first position with respect to the elongated member, the clamp is positioned to clamp the second end of the needle, and wherein when the clamp is a second position with respect to the elongated member, the clamp is positioned to reposition the needle to be engaged by the first end of the needle pusher.

15. A suturing device comprising:
- a needle pusher having a first end configured to releasably engage a needle;
- an elongated member dimensioned for insertion into a body including tissue, the elongated member including a proximal end and a distal end opposite the proximal end;
- a cavity formed in a surface of the elongated member between the proximal end and the distal end of the elongated member;
- a working channel within the elongated member, the working channel extending from the proximal end of the elongated member to the cavity and dimensioned to allow the needle pusher to move axially through the working channel;

a guide structure disposed between the cavity and the distal end of the elongated member, the guide structure including at least a first channel coaxially aligned with the working channel;

an opening formed in the surface of the elongated member between the guide structure and the distal end of the elongated member;

a needle capturing assembly disposed between the opening and the distal end of the elongated member; and a suction channel in fluid communication with the cavity;

wherein the suction channel and the cavity are configured such that when the elongated member is inserted into the body adjacent to the tissue and a vacuum is applied to the suction channel by a vacuum source, the tissue is captured by the cavity;

wherein the working channel, the guide structure, the needle pusher, the cavity and the needle capturing assembly are configured such that (i) when the needle is engaged by the needle pusher and the tissue is captured by the cavity, the needle pusher is moveable through the working channel in a first direction towards the distal end of the elongated member to move the needle through the working channel in the first direction such that entirety of the needle passes through the tissue, at least a portion of the needle remains within the first channel of the guide structure and a first end of the needle is captured by the needle capturing assembly and (ii) when the needle is engaged by the needle pusher and the first end of the needle is captured by the needle capturing assembly, the needle pusher is further moveable through the working channel in a second direction towards the proximal end of the elongated member such that the needle is disengaged from the needle pusher and the first end of the needle remains captured by the needle capturing assembly, and wherein the opening is dimensioned to receive an apparatus for extracting the needle from the needle capturing assembly when the needle is captured by the needle capturing assembly.

16. The suturing device of claim 15, wherein at least a portion of the elongated member forming a bottom surface of the cavity comprises a light transmissive material and wherein the suturing device further comprises a light source configured such that light from the light source is directed through the bottom surface of the cavity towards an open side of the cavity.

17. The suturing device of claim 15, further comprising:
a dividing structure within the cavity, the dividing structure dividing the cavity into a first cavity portion and a second cavity portion;

wherein the first cavity portion and the second cavity portion are in fluidic communication with the vacuum source such that when the vacuum is applied to the first cavity portion, a first portion of the tissue is captured by the first cavity portion, and when the vacuum is applied to the second cavity portion, a second portion of the tissue is captured by the second cavity portion;

wherein when the needle is engaged by the needle pusher and the first portion of the tissue is captured by the first cavity portion, the needle pusher is moveable in the first direction to move the needle through the working channel in the first direction such that the entirety of the needle passes through the first portion of the tissue; and wherein when the needle is engaged by the needle pusher and the second portion of the tissue is captured by the second cavity portion, the needle pusher is moveable in the first direction to move the needle through the working channel in the first direction such that entirety of the needle passes through the second portion of the tissue after passing through the first portion of the tissue and until the first end of the needle is captured by the needle capturing assembly while the at least a portion of the needle remains within the first channel of the guide structure.

18. The suturing device of claim 15, wherein:
the guide structure includes a second channel adjacent to the first channel;
the first channel and the second channel are coaxially aligned; and
the first channel and the second channel are dimensioned such that the needle pusher and the needle can be moved axially through the first channel, the needle can move axially through the second channel, and the needle pusher cannot move axially through the second channel.

19. The suturing device of claim 15, further comprising:
a fixed handle coupled to the proximal end of the elongated member; and
an operating handle coupled to a second end of the needle pusher opposite the first end of the needle pusher,
wherein the fixed handle and the operating handle are configured for a user of the suturing device to push or pull the operating handle using the fixed handle as leverage to control the movement of the needle pusher within the working channel.

20. A suturing device comprising:
an elongated member dimensioned for insertion into a body including tissue, the elongated member including a first end and a second end opposite the first end, a cavity formed in a surface thereof, a needle passage, and a vacuum port, wherein the cavity includes a first end and a second end opposite the first end of the cavity and wherein when the elongated member is inserted into the body and a vacuum is applied to the cavity by a vacuum source through the vacuum port, the tissue is captured by the cavity;

a needle capturing assembly disposed between the second end of the cavity and the second end of the elongated member; and a needle pusher including a first end for engaging a needle, wherein when the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly, wherein application of the vacuum to the cavity is controlled by the movement of the needle pusher, and wherein the suturing device further comprises a needle pusher assembly, the needle pusher assembly including the needle pusher and an operating handle coupled to a second end of the needle pusher opposite the first end of the needle pusher.

21. A suturing device comprising:
an elongated member dimensioned for insertion into a body including tissue, the elongated member including a first end and a second end opposite the first end, a cavity formed in a surface thereof, a needle passage, and a vacuum port, wherein the cavity includes a first end and a second end opposite the first end of the cavity and wherein when the elongated member is inserted into the body and a vacuum is applied to the cavity by a vacuum source through the vacuum port, the tissue is captured by the cavity;

a needle capturing assembly disposed between the second end of the cavity and the second end of the elongated member; and a needle pusher including a first end for engaging a needle, wherein when the needle is engaged by the needle pusher and the tissue is captured by the cavity, the needle pusher is moveable in a first direction to move the needle through the needle passage in the first direction such that entirety of the needle passes through the tissue and a first end of the needle is captured by the needle capturing assembly and the needle pusher is further moveable in a second direction such that the needle is disengaged from the needle pusher while the first end of the needle remains captured by the needle capturing assembly, wherein:

application of the vacuum to the cavity is controlled by the movement of the needle pusher, the elongated member further includes an aperture formed in the surface of the elongated member, the suturing device further includes a blocking member coupled to the needle pusher, and a first movement of the needle pusher causes a corresponding first movement of the blocking member to block the aperture and a second movement of the needle pusher causes a corresponding second movement of the blocking member to unblock the aperture, to thereby control the application of the vacuum to the cavity.

22. The suturing device of claim 21, wherein the needle pusher comprises a first cylinder having an opening at the first end of the needle pusher, the opening dimensioned to engage the needle, and wherein the blocking member comprises a second cylinder arranged parallel to the first cylinder.

* * * * *